US008975262B2

(12) United States Patent
DeGrado et al.

(10) Patent No.: US 8,975,262 B2
(45) Date of Patent: *Mar. 10, 2015

(54) SYNTHETIC MIMETICS OF HOST DEFENSE AND USES THEREOF

(75) Inventors: William F. DeGrado, Media, PA (US); Haizhong Tang, Lawrenceville, NJ (US); Bozena Korczak, Wayne, PA (US); Dahui Liu, Wynnewood, PA (US); Richard W. Scott, Rador, PA (US); Yongjiang Xu, Wayne, PA (US)

(73) Assignee: Cellceutix Corporation, Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/563,928

(22) Filed: Aug. 1, 2012

(65) Prior Publication Data

US 2013/0090345 A1    Apr. 11, 2013

Related U.S. Application Data

(63) Continuation of application No. 12/605,584, filed on Oct. 26, 2009, now Pat. No. 8,278,309.

(60) Provisional application No. 61/108,595, filed on Oct. 27, 2008.

(51) Int. Cl.
*C07D 403/14*    (2006.01)

(52) U.S. Cl.
CPC .................................. *C07D 403/14* (2013.01)
USPC ........................................................ 514/256

(58) Field of Classification Search
CPC .................................................... C07D 403/14
USPC ........................................... 514/256; 544/335
See application file for complete search history.

(56) References Cited

U.S. PATENT DOCUMENTS

| | | | |
|---|---|---|---|
| 3,496,179 | A | 2/1970 | Hans-Jurgen et al. |
| 5,656,591 | A | 8/1997 | Tomita |
| 6,172,104 | B1 | 1/2001 | Tidwell et al. |
| 6,482,799 | B1 | 11/2002 | Tuse et al. |
| 6,835,808 | B2 | 12/2004 | Quentin et al. |
| 7,590,517 | B2 | 9/2009 | Doerksen et al. |
| 8,278,309 | B2 * | 10/2012 | DeGrado et al. .............. 514/256 |
| 2003/0109570 | A1 | 6/2003 | Tsunoda et al. |
| 2004/0102941 | A1 | 5/2004 | Lopez et al. |
| 2004/0185257 | A1 | 9/2004 | DeGrado et al. |
| 2004/0202639 | A1 | 10/2004 | DeGrado et al. |
| 2005/0065091 | A1 | 3/2005 | Peyman |
| 2005/0287108 | A1 | 12/2005 | DeGrado et al. |
| 2006/0024264 | A1 | 2/2006 | Kuroda et al. |
| 2006/0041023 | A1 | 2/2006 | DeGrado et al. |
| 2006/0078626 | A1 | 4/2006 | Smith |
| 2008/0131731 | A1 | 6/2008 | Igawa et al. |
| 2008/0176807 | A1 | 7/2008 | DeGrado et al. |
| 2010/0081665 | A1 | 4/2010 | Scott et al. |

FOREIGN PATENT DOCUMENTS

| | | | |
|---|---|---|---|
| WO | 02/100295 | 12/2002 | |
| WO | 02/100295 A2 | 12/2002 | |
| WO | 03/045307 | 5/2003 | |
| WO | 2004/082634 A2 | 3/2004 | |
| WO | 2004/082643 | 9/2004 | |
| WO | 2005/072246 A2 | 8/2005 | |
| WO | 2005/104712 | 11/2005 | |
| WO | 2005/123660 | 12/2005 | |
| WO | 2006/058022 | 6/2006 | |
| WO | 2006/067577 | 6/2006 | |
| WO | 2006/093813 | 9/2006 | |
| WO | 2006/132647 A2 | 12/2006 | |
| WO | 2008/083256 | 7/2008 | |
| WO | WO 2008/083256 | * 7/2008 | .............. A61P 27/02 |
| WO | 2009/061697 | 5/2009 | |

OTHER PUBLICATIONS

Non-final office action for related U.S. Appl. No. 11/965,194 dated Apr. 27, 2012.
Atherton E, "Solid Phase Peptide Synthesis: A Practical Approach," IRL Press, Oxford U.K., 1989.
Odian, G., "Principles of polymerization," John Wiley and Sons, Inc., New York, 1991.
Stevens, M. "Ploymer Chemistry," Oxford University Press, 1999.
Metz et. al., "Protamine and newer heparin antagonists" in Stoetling, R. K. (ed): Pharmacology and Physiology in Anesthetic Practice. vol. 1. Philadelphia, PA, JB Lippincott, 1-15, 1994.
Wick, et al., J. Phys. Chem., 2000;104:3093-3104.
Solid-phase Synthesis: A Practical Guide, Kates, S. A., and Albericio, F., eds., Marcel Dekker, New York (2000).
T. W. Green and P.G.M. Wuts, Protective Groups in Organic Synthesis, 3rd Ed., 1999, Wiley & Sons, Inc., New York.
Maniatis, et al., Molecular Cloning—A Laboratory Manual, 2nd Ed., 1989, Cold Spring Harbor Press.
Jerry March, Advanced Organic Chemistry, 4th Ed., Wiley-Interscience, (1992).
A. R. Gennaro (editor), Remington's Pharmaceutical Sciences, Mack Publishing Co. (1980).
Guillemot, D. et al., Low Dosage and Long Treatment Duration of Beta-Lactam, JAMA, Feb. 4, 1998; 279 (5):365-370.
Arnt, L., et al., Rapid Communication: Nonhemolytic Abiogenic Polymers Antimicrobial Peptide Mimics, Journal of Polymer Science, Part A: Polymer Chemistry, 2004, 42:3860-3864.
Montecolvo, M. A., et al., Outbreak of Vancomycin-, Ampicillin-, and Aminoglycosid-Resistant *Enterococcus faecium* Bacteremia in an Adult Oncology Unit, Antimicrobial Agents and Chemotherapy, Jun. 1994; 38(6):1363-1367.
Lathers, C.M., Clinical pharmacology of antimicrobial use in humans and animals, The Journal of Clinical Pharmacology, 2002, 42:587-600.
Monroe, S., et al., Antimicrobial use and bacterial resistance, Curr Opin Microbiol, Oct. 2000; 3(5):496-501.
Liu, et al., Nontoxic Membrane-Active Antimicrobial Arylamide Oligomers, Angew Chem Int Ed Engl, 2004;43:1158-1162.

(Continued)

*Primary Examiner* — Erich A Leeser
(74) *Attorney, Agent, or Firm* — Pepper Hamilton LLP

(57) ABSTRACT

The present invention provides arylamide compounds and methods of making and using them as antibiotics.

2 Claims, 5 Drawing Sheets

(56) References Cited

OTHER PUBLICATIONS

Vippagunta, S. R., et al., Crystalline solids, Adv Drug Deliv Rev. May 16, 2001;48(1):3-26.
West, A. R., Solid State Chemistry and it's Application, Wiley, New York, 1988, pp. 358 & 365.
Non-final office action for related U.S. Appl. No. 11/965,194 dated Sep. 14, 2011.
Walenga et al, "Factor Xa inhibition in mediating anthrombotic actions: application of a synthetic haprin pentasaccharide," doctoral thesis. In. Paris: Universite Pierre et Marie Curie, Paris VI, Paris, France, Jun. 1987.
Hirsh J., et al., "Heparin and low-molecular-weight heparin: mechanisms of action, pharmacokinetics, dosing, monitoring, efficacy, and safety," Chest. Jan. 2001; 119 (1 Suppl):64S-94S.
Bendetowicz AV, et al., "Pharmacokinetics and pharmacodynamics of a low molecular weight heparin (enoxaparin) after subcutaneous injection, comparison with unfractionated heparin—a three way cross over study in human volunteers," Thromb Haemost. Mar. 1994;71(3):305-13.
Morabia A., "Heparin doses and major bleeding," Lancet, May 31, 1986;1(8492):1278-9.
Mureebe L., et al., "Heparin-induced thrombocytopenia: pathophysiology and management," Vasc Endovascular Surg. May-Jun. 2002;36(3):163-70.
Lubenow N., et al., "Heparin-induced thrombocropenia: temporal pattern of thrombocytopenia in relation to initial use or reexposure to heparin," Chest. Jul. 2002; 122(1): 37-42.
Hirsh J., et al., "Low Molecular Weight Heparin," Blood. Jan. 1, 1992; 79(1): 1-17.
Ofosu FA., et al., "Mechanisms of Action of Low Molecular Weight Haparins and Heparinoids," Baillieres Clin Haematol. Jul. 1990; 3(3): 505-29.
Hirsh J., et al., "Heparin and low-molecular-weight heparin: the Seventh ACCP Conference on Antithrombotic and Thrombolytic Therapy," Chest. Sep. 2004, 126 (3 Suppl): 188S-203S.
Becker RC., "New thrombolytics, anticoagulants, and platelet antagonists: the future of clinical practice," J Thromb Thrombolysis. Apr. 1999; 7(2): 195-220.
Antman EM, et al., "Enoxaparin prevents death and cardiac ischemic events in unstable angina/non-Q-wave myocardial infarction. Results of the thrombolysis in myocardial infarction (TIMI) 11B trial," Circulation. Oct. 12, 1999;100(15):1593-601.
Cohen M., et al., "A comparison of low-molecular-weight heparin with unfractionated heparin for unstable coronary artery disease. Efficacy and Safety of Subcutaneous Enoxaparin in Non-Q-Wave Coronary Events Study Group," N Engl J Med. Aug. 14, 1997;337(7):447-52.
Lee AY, et al., "Randomized comparison of low molecular weight heparin and coumarin derivatives on the survival of patients with cancer and venous thromboembolism," J Clin Oncol. Apr. 1, 2005;23(10):2123-9.
Walenga JM, et al., "Short- and long-acting synthetic pentasaccharides as antithrombotic agents," Expert Opin Investig Drugs Jul. 2005; 14(7):847-58.
Mehta SR, et al., "Efficacy and safety of fondaparinux versus enoxaparin in patients with acute coronary syndromes undergoing percutaneous coronary intervention: results from the OASIS-5 trial," J Am Coll Cardiol. Oct. 30, 2007;50(18):1742-51. Epub Oct. 15, 2007.
Hubbard AR, et al., "Neutralisation of heparan sulphate and low molecular weight heparin by protamine," Thromb Haemost. Feb. 18, 1985;53(1):86-9.
Poon MC, et al., "Platelet factor four and protamine sulfate neutralization of heparin fractionated according to anionic charge density," Thromb Haemost Apr. 30, 1982;47(2):162-5.
Massonnet-Castel S., et al "Partial reversal of low molecular weight heparin (PK 10169) anti-Xa activity by protamine sulfate: in vitro and in vivo study during cardiac surgery with extracorporeal circulation," Haemostasis. 1986;16(2):139-46.
Doutremepuich C., et al. "In vivo neutralization of low-molecular weight heparin fraction CY 216 by protamine," Semin Thromb Hemost Jul. 1985;11(3):318-22.
Weiler JM, et al. "Serious adverse reactions to protamine sulfate: are alternatives needed?" J Allergy Clin Immunol. Feb. 1985;75(2):297-303.
Horrow JC., "Protamine: a review of its toxicity," Anesth Analg. Mar. 1985;64(3):348-61.
Porsche R., et al. "Allergy to protamine sulfate," Heart Lung. Nov.-Dec. 1999; 28(6):418-28.
Vlugt, T. J. H., et al., Improving the efficiency of the configurational-bias Monte Carlo algorithm, Mol. Phys., 1998, 94, 727-733.
Röthlisberger, U., et al., The torsional potential of perfluoro n-alkanes: A density functional study, J. Chem., Phys., 1996, 3692-3700.
Lee, M. K. and Lander, A. D., "Analysis of affinity and structural selectivity in the binding of proteins to glycosaminoglycans: development of a sensitive electrophoretic approach" Proc Natl Acad Sci U S A. Apr. 1, 1991;88 (7):2768-72.
Car R., et al., "Unified approach for molecular dynamics and density-functional theory," Phys Rev Lett. Nov. 25, 1985;55(22):2471-2474.
Martin, M. G., et al., Novel Configurational-Bias Monte Carlo Method for Branched Molecules. Transferable Potentials for Phase Equilibria. 2. United-Atom Description of Branched Alkanes, J. Phys. Chem. B 103, 4508-4517, 1999.
Brooks, B. R., et al., Charmm: A Program for Macromolecular Energy, Minimization, and Dynamics Calculations, J. Comp. Chem. 4, 187-217, 1983.
Barany G., et al. "Solid-phase peptide synthesis: a silver anniversary report," Int J Pept Protein Res. Dec. 1987;30 (6):705-39.
Ando et. al., in Kleinzeller, A. (ed): "Protamine: Molecular biology, biochemistry and biophysics" vol. 12. 1973. New York, Springer-Verlag, 1-109.
Siepmann, J. I., et al., Configurational bias Monte Carlo: a new sampling scheme for flexible chains, Mol. Phys., 1992;75(1):59-70.
Yamaguchi, I., et al., Synthesis of polyurea rotaxanes using a cyclodextrin complex of a,ω-diamine, Polym. Bull., 2000;44:247-253.
International Search Report dated Mar. 12, 2010.
Jerry March, Advanced Organic Chemistry, 4th Ed., Wiley-Interscience.
A. R. Gennaro (editor), Remington's Pharmaceutical Sciences, Mack Publishing Co.
Tang et al., "Synthesis of urea oligomers and their antibacterial activity," Chem Com (2005) (12):1537-1539.
Choi et al., "De novo design and in vivo activity of conformationally restrained antimicrobial arylamide foldamers," Proc Natl Acad Sci U S A. (2009) 106(17):6968-6973.

* cited by examiner

SYNTHETIC MIMETICS OF HOST DEFENSE AND USES THEREOF

CROSS-REFERENCE TO RELATED APPLICATIONS

This application is a continuation of U.S. application Ser. No. 12/605,584 filed Oct. 26, 2009, which claims priority to U.S. provisional application Ser. No. 61/108,595 filed Oct. 27, 2008, which is incorporated herein by reference in its entirety.

REFERENCE TO GOVERNMENT GRANTS

The present invention was supported by funds from the U.S. Government (NIH Grant Nos. AI74866 and 1R43A1058407) and the U.S. Government may therefore have certain rights in the invention.

FIELD OF THE INVENTION

The present invention is directed, in part, to arylamide compounds and to methods of making and using the same.

BACKGROUND OF THE INVENTION

Antimicrobial peptides (AMPs) represent a first line of defense against microbes for many species. AMPs are typically small (12-80 amino acids) cationic amphiphiles. There are two types of AMPs comprising ribosomally and nonribosomally synthesized peptides. Over 700 AMPs have been identified and are generally α-helical (magainin and cecropin) or disulfide-rich β-sheets (bactenecin and defensin). Although the peptides are composed of many different sequences, their physiochemical properties are remarkably similar. They adopt an amphiphilic architecture with positively charged groups segregated to one side of the secondary structure and hydrophobic groups on the opposite surface. In mammals, the peptides are produced and secreted in skin, mucosal surfaces and neutrophils, and act locally in response to infection. It is the overall physiochemical properties that are largely responsible for biological activity of these peptides.

Some antimicrobial activities of host defense proteins have been linked to direct cytotoxic actions and modulation of the innate immune system. Their direct antimicrobial activities are proposed to involve both membrane and non-membrane effects. Antimicrobial peptides have remained an effective weapon against bacterial infection over evolutionary time indicating that their mechanism of action thwarts bacterial responses which lead to resistance against toxic substances. This premise is supported by direct experimental data showing that no appreciable resistance to the action of the antimicrobial peptides occurs after multiple serial passages of bacteria in the presence of sub-lethal concentrations of the peptides.

There is a dire need for development of new antimicrobial agents that attack new targets to evade resistance issues that limit the usefulness of many antibiotics. Furthermore, these new agents should exert their antimicrobial activity via mechanisms that bacteria do not effectively resist. A series of non-peptidic analogues have been developed that have many advantages over peptides because of their small size, which increases stability and enhances tissue distribution, and ability to fine-tune their physical properties for optimization of potency and safety. A series of arylamide compounds that mimic structural properties of the antimicrobial peptides were found to have potent antibacterial activities and wide selectivity ratios versus mammalian cells.

SUMMARY OF THE INVENTION

The present invention provides compounds of Formula I

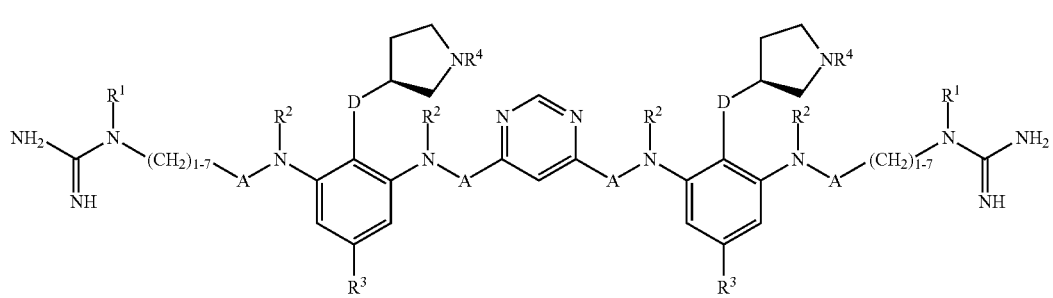

wherein: each A is, independently, —C═O, —C═S, or —CH$_2$; each D is, independently, O or S; each R$^1$ is, independently, hydrogen, C$_{1-3}$alkyl, C$_{1-3}$alkoxy, halo, or halo C$_{1-3}$alkyl; each R$^2$ is, independently, hydrogen, C$_{1-3}$alkyl, C$_{1-3}$alkoxy, halo, or haloC$_{1-3}$alkyl; each R$^3$ is, independently, hydrogen, C$_{1-4}$alkyl, C$_{1-4}$alkoxy, halo, or haloC$_{1-4}$alkyl; and each R$^4$ is, independently, hydrogen, C$_{1-3}$alkyl, C$_{1-3}$alkoxy, halo, or haloC$_{1-3}$alkyl; or a pharmaceutically acceptable salt thereof.

In some embodiments, each A is —C═O.

In some embodiments, each D is O.

In some embodiments, each R$^1$ is, independently, hydrogen, methyl, ethyl, methoxy, ethoxy, halo, or haloC$_{1-3}$alkyl. In some embodiments, each R$^1$ is, independently, hydrogen, methyl, methoxy, halo, or haloC$_{1-3}$alkyl. In some embodiments, each R$^1$ is, independently, hydrogen, methyl, or methoxy. In some embodiments, each R$^1$ is hydrogen.

In some embodiments, each R$^2$ is, independently, hydrogen, methyl, ethyl, methoxy, ethoxy, halo, or haloC$_{1-3}$alkyl. In some embodiments, each R$^2$ is, independently, hydrogen, methyl, methoxy, or halo. In some embodiments, each R$^2$ is hydrogen.

In some embodiments, each $R^3$ is, independently, hydrogen, methyl, ethyl, methoxy, ethoxy, halo, or haloC$_{1-3}$alkyl. In some embodiments, each $R^3$ is, independently, methyl, methoxy, halo, or haloC$_{1-3}$alkyl. In some embodiments, each $R^3$ is, independently, halo or haloC$_{1-3}$alkyl. In some embodiments, each $R^3$ is, independently, haloC$_{1-3}$alkyl. In some embodiments, each $R^3$ is trifluoromethyl.

In some embodiments, each $R^4$ is, independently, hydrogen, methyl, ethyl, methoxy, ethoxy, or haloC$_{1-3}$alkyl. In some embodiments, each $R^4$ is, independently, hydrogen, methyl, methoxy, halo, or haloC$_{1-3}$alkyl. In some embodiments, each $R^4$ is, independently, hydrogen, methyl, methoxy, or halo. In some embodiments, each $R^4$ is hydrogen.

In some embodiments, each A is, independently, —C═O, —C═S, or CH$_2$; each D is, independently, O or S; each $R^1$ is, independently, hydrogen, methyl, ethyl, methoxy, ethoxy, halo, halomethyl, or haloethyl; each $R^2$ is, independently, hydrogen, methyl, methoxy, halo, or halomethyl; each $R^3$ is, independently, C$_{1-3}$alkyl, C$_{1-3}$alkoxy, halo, or haloalkyl; and each $R^4$ is, independently, hydrogen, methyl, ethyl, methoxy, ethoxy, halo, halomethyl, or haloethyl.

In some embodiments, each A is, independently, —C═O or —C═S; each D is, independently, O or S; each $R^1$ is, independently, hydrogen, methyl, methoxy, halo, or halomethyl; each $R^2$ is, independently, hydrogen, halo, or halomethyl; each $R^3$ is, independently, methyl, ethyl, methoxy, ethoxy, halo, halomethyl, or haloethyl; and each $R^4$ is, independently, hydrogen, methyl, ethyl, methoxy, ethoxy, halo, halomethyl, or haloethyl.

In some embodiments, each A is —C═O; each D is O; each $R^1$ is, independently, hydrogen, halo, or halomethyl; each $R^2$ is, independently, hydrogen or halo; each $R^3$ is, independently, methyl, methoxy, halo, or halomethyl; and each $R^4$ is, independently, hydrogen, methyl, methoxy, halo, or halomethyl.

In some embodiments, each A is —C═O; each D is O; each $R^1$ is, independently, hydrogen or halo; each $R^2$ is, independently, hydrogen or halo; each $R^3$ is, independently, methyl, halo, or halomethyl; and each $R^4$ is, independently, hydrogen, methyl, halo, or halomethyl.

In some embodiments, each A is —C═O; each D is O; each $R^1$ is, independently, hydrogen or halo; each $R^2$ is, independently, hydrogen or halo; each $R^3$ is, independently, halo or halomethyl; and each $R^4$ is, independently, hydrogen or halo.

In some embodiments, each A is —C═O; each D is O; each $R^1$ is, independently, hydrogen or halo; each $R^2$ is, independently, hydrogen or halo; each $R^3$ is, independently, methyl, halo, or halomethyl; and each $R^4$ is, independently, hydrogen, methyl, halo, or halomethyl.

In some embodiments, the compound is

The present invention also provides pharmaceutical compositions comprising one or more of the compounds described above or salt of any of the compounds described above and a pharmaceutically acceptable carrier.

The present invention also provides formulations comprising one or more of the compounds described above, wherein the formulation comprises saline, water, a cyclodextrin solution, or a buffered solution of pH 3 to 9. In some embodiments, the formulation is an oral non-absorbed formulation. In some embodiments, the formulation comprises an excipient chosen from purified water, propylene glycol, polyethyleneglycol 400 (PEG 400), glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, or any combination thereof. In some embodiments, the formulation comprises an excipient chosen from propylene glycol, purified water, and glycerin. In some embodiments, the formulation comprises an excipient chosen from 20% w/v propylene glycol in saline, 30% w/v propylene glycol in saline, 40% w/v propylene glycol in saline, 50% w/v propylene glycol in saline, 15% w/v propylene glycol in purified water, 30% w/v propylene glycol in purified water, 50% w/v propylene glycol in purified water, 30% w/v propylene glycol and 5 w/v ethanol in purified water, 15% w/v glycerin in purified water, 30% w/v glycerin in purified water, 50% w/v glycerin in purified water, 20% w/v Kleptose in purified water, 40% w/v Kleptose in purified water, and 25% w/v Captisol in purified water.

The present invention also provides methods of preparing Compound A comprising:

a) reacting (R)-(−)-N-Boc-3-pyrrolidinol with a strong base to form a mixture; further reacting the mixture with 2-chloro-5-(trifluoromethyl)-1,3-dinitrobenzene to form a compound having Formula II

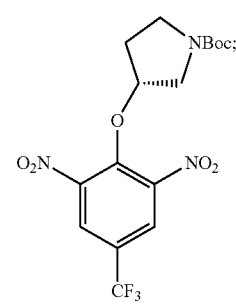

II

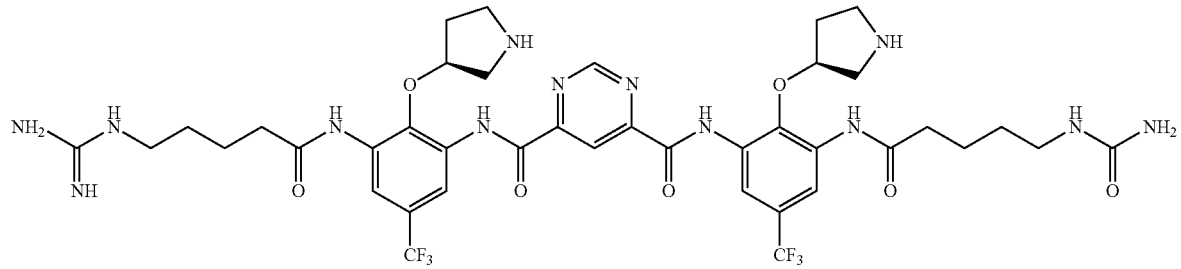

Compound A or a pharmaceutically acceptable salt thereof.

b) reacting the compound of Formula II with an alcohol and a transition metal catalyst in the presence of hydrogen to form a compound of Formula III

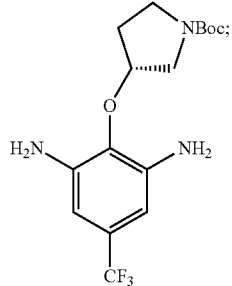

c) adding the compound of Formula III and pyrimidine-4,6-dicarboxylic acid to a mixture of 2-chloro-4,6-dimethoxy-1,3,5-triazine and N-methylmorpholine to form a compound of Formula IV

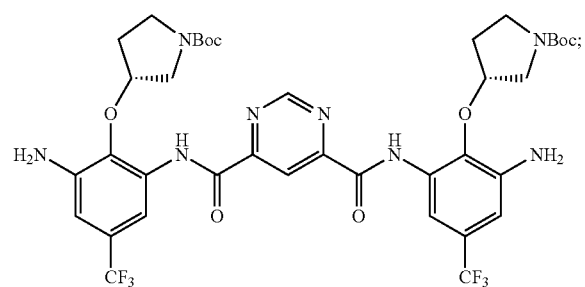

d) reacting the compound of Formula IV with N-Boc-guanidine butyric acid to form a compound of Formula V

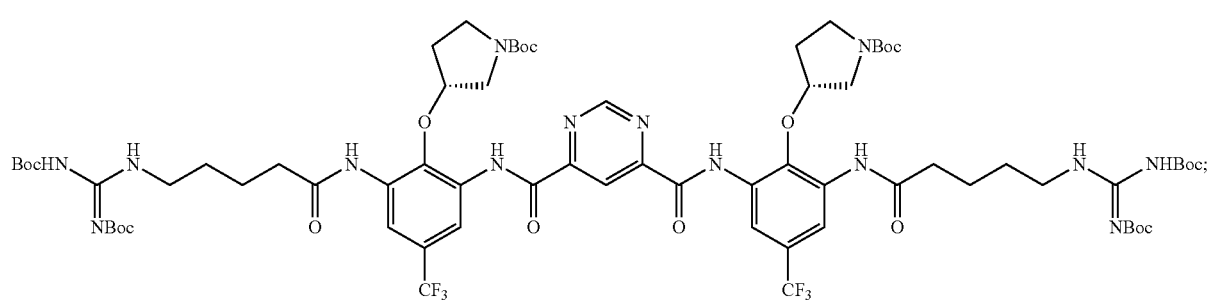

and e) deprotecting the compound of Formula V to produce Compound A. In some embodiments, in a) the strong base is NaH; and in b) the transition metal catalyst is Pd/C and the alcohol is ethanol.

The present invention also provides alternate methods of preparing Compound A comprising:

a) deprotonating (R)-3-Hydroxypyrrolidine-1-carboxylic acid tert-butyl ester, and reacting the resultant compound with 2-chloro-1,3-dinitro-5-trifluoromethylbenzene to form (R)-3-(2,6-dinitro-4-trifluoromethylphenoxy)pyrrolidine-1-carboxylic acid tert-butyl ester;

b) reducing (R)-3-(2,6-dinitro-4-trifluoromethylphenoxy)pyrrolidine-1-carboxylic acid tert-butyl ester in the presence of an alcohol, a transition metal catalyst, and hydrogen to form (R)-3-(2,6-diamino-4-trifluoromethylphenoxy)-pyrrolidine-1-carboxylic acid tert-butyl ester;

c) coupling (R)-3-(2,6-diamino-4-trifluoromethylphenoxy)-pyrrolidine-1-carboxylic acid tert-butyl ester with pyrimidine-4,6-dicarboxylic acid in the presence of 1-[(3-(dimethylamino)-propyl)]-3-ethylcarbodiimide hydrochloride to form pyrimidine-4,6-dicarboxylic acid bis-{[3-amino-2-((R)-1-(tert-butoxycarbonyl)pyrrolidin-3-yloxy)-5-trifluoromethyl-phenyl]amide};

d) reacting pyrimidine-4,6-dicarboxylic acid bis-{[3-amino-2-((R)-1-(tert-butoxycarbonyl)pyrrolidin-3-yloxy)-5-trifluoromethyl-phenyl]amide} with ({[(tert-butoxycarbonyl)amino][(tert-butoxycarbonyl)imino]methyl}amino)pentanoic acid in the presence of phosphorous oxychloride to form pyrimidine-4,6-dicarboxylic acid bis-{[3-(5-({[(tert-butoxycarbonyl)amino][(tert-butoxycarbonyl)imino]methyl}amino)-pentanoylamino)-2-((R)-1-(tert-butoxycarbonyl)-pyrrolidin-3-yloxy)-5-trifluoromethyl-phenyl]-amide};

e) deprotecting pyrimidine-4,6-dicarboxylic acid bis-{[3-(5-({[(tert-butoxycarbonyl)amino][(tert-butoxycarbonyl)imino]methyl}amino)-pentanoylamino)-2-((R)-1-(tert-butoxycarbonyl)-pyrrolidin-3-yloxy)-5-trifluoromethyl-phenyl]-amide} to form crude pyrimidine-4,6-dicarboxylic acid bis-{[3-(5-guanidino-pentanoylamino)-2-((R)-pyrrolidin-3-yloxy)-5-trifluoromethyl-phenyl]-amide}tetrahydrochloride; and f) purifying crude pyrimidine-4,6-dicarboxylic acid bis-{[3-(5-guanidino-pentanoylamino)-2-((R)-pyrrolidin-3-yloxy)-5-trifluoromethyl-phenyl]-amide}tetrahydrochloride by, for example, reverse-phase chromatography.

The present invention also provides second alternate methods of preparing Compound A comprising:

a) deprotonating (R)-3-Hydroxypyrrolidine-1-carboxylic acid tert-butyl ester and further reacting the resultant compound with 2-chloro-1,3-dinitro-5-trifluoromethylbenzene to form (R)-3-(2,6-dinitro-4-trifluoromethylphenoxy)pyrrolidine-1-carboxylic acid tert-butyl ester;

b) reducing (R)-3-(2,6-dinitro-4-trifluoromethylphenoxy)pyrrolidine-1-carboxylic acid tert-butyl ester in the presence of an alcohol, a transition metal catalyst, and hydrogen, to form (R)-3-(2,6-diamino-4-trifluoromethylphenoxy)-pyrrolidine-1-carboxylic acid tert-butyl ester;

c) coupling (R)-3-(2,6-diamino-4-trifluoromethylphenoxy)-pyrrolidine-1-carboxylic acid tert-butyl ester with pyrimidine-4,6-dicarboxylic acid in the presence of 1-[(3-(dimethylamino)-propyl)]-3-ethylcarbodiimide hydrochloride to form pyrimidine-4,6-dicarboxylic acid bis-{[3-amino-2-((R)-1-(tert-butoxycarbonyl)pyrrolidin-3-yloxy)-5-trifluoromethyl-phenyl]amide};

d) reacting pyrimidine-4,6-dicarboxylic acid bis-{[3-amino-2-((R)-1-(tert-butoxycarbonyl)pyrrolidin-3-yloxy)-5-trifluoromethyl-phenyl]amide} with N-Cbz acid in the presence of thionyl chloride;

e) reducing the resultant compound of d) in the presence of an alcohol, a transition metal catalyst, and hydrogen;

f) reacting the resultant compound of e) with di-Boc pyrazole; and g) deprotecting the resultant compound of f) to produce Compound A.

The present invention also provides methods of preparing a pharmaceutically acceptable salt of Compound A comprising:

a) reacting (R)-(−)-N-Boc-3-pyrrolidinol with a strong base to form a mixture; further reacting the mixture with 2-chloro-5-(trifluoromethyl)-1,3-dinitrobenzene to form a compound having Formula II

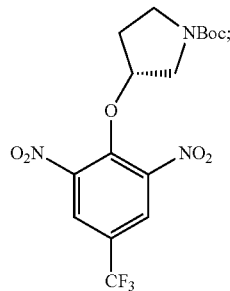

II b) reacting the compound of Formula II with an alcohol and a transition metal catalyst in the presence of hydrogen to form a compound of Formula III

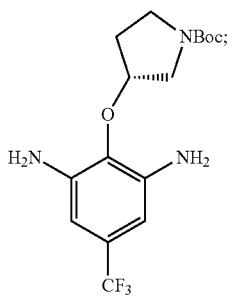

III c1) adding the compound of Formula III and pyrimidine-4,6-dicarboxylic acid to a mixture of 2-chloro-4,6-dimethoxy-1,3,5-triazine and N-methylmorpholine to form a compound of Formula IV

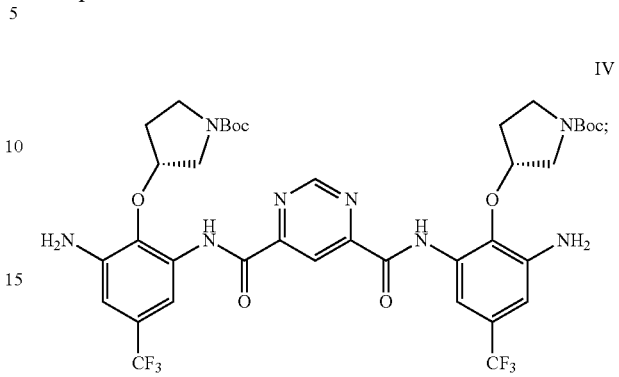

IV or c2) adding the compound of Formula III and pyrimidine-4,6-dicarboxylic acid to a mixture of 1-ethyl-3-[3-(dimethylamino)propyl]-carbodiimide hydrochloride (EDCl) and anhydrous pyridine to form a compound of Formula IV

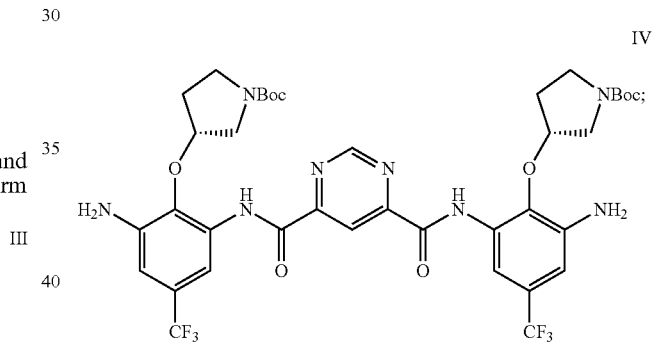

IV d) adding the compound of Formula IV with an N-Cbz acid to a solution comprising anhydrous pyridine, dimethylaminopropylamine, and any one of thionyl chloride, POCl₃, (EtO)₂POCl, or oxalyl chloride to form a compound of Formula Va

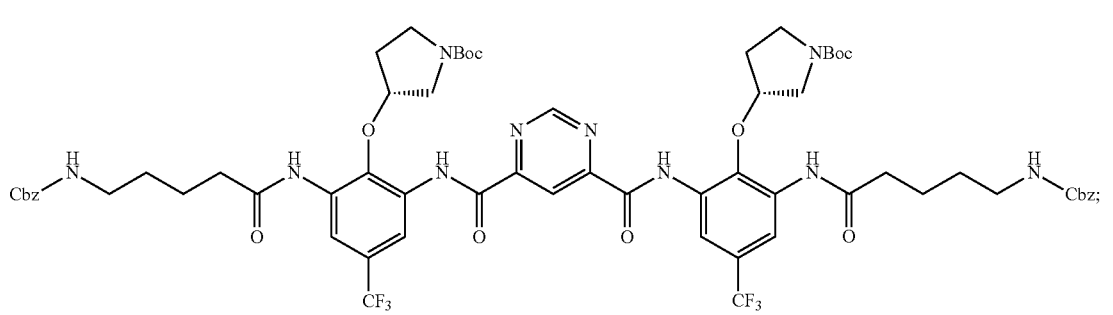

Va e) hydrogenlysis of the Cbz group of the compound of Formula Va to produce the compound of formula VI

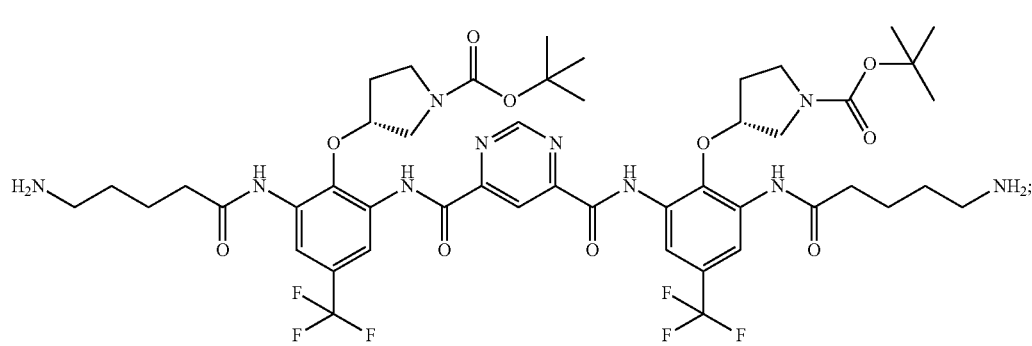

f) protecting the compound of Formula VI to produce the compound of formula VII

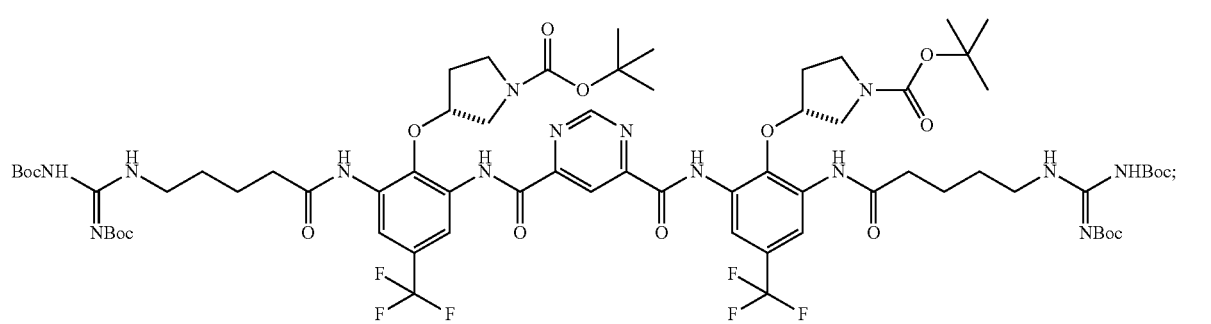

and g) deprotecting the compound of Formula VII to produce a pharmaceutically acceptable salt of Compound A.

The present invention also provides methods of inhibiting the growth of a microbe comprising contacting the microbe with any of the compounds described above, or pharmaceutically acceptable salts thereof.

The present invention also provides methods of treating a mammal having a microbial infection comprising administering to the mammal in need thereof an anti-microbial effective amount of any of the compounds described above, or pharmaceutically acceptable salts thereof.

In some embodiments, the microbe or microbial infection is a gram-negative aerobe, a gram-positive aerobe, a gram-negative anaerobe, a gram-positive anaerobe, a mycobacterium or a yeast. In some embodiments, the gram-negative aerobe is *Escherichia coli, Citrobacter freundii, Citrobacter diverus, Citrobacter koseri, Enterobacter cloacae, Enterobacter faecalis, Klebsiella pneumonia, Klebsiella oxytoca, Morganella morganii, Providencia stuartii, Proteus vulgaris, Proteus mirabilis, Serratia marcescens, Acinetobacter haemolyticus, Acinetobacter junii, Acinetobacter lwoffii, Haemophilus influenzae, Stenotrophomonas maltophilia,* or *Pseudomonas aeruginosa*. In some embodiments, the gram-positive aerobe is *Enterococcus faecalis, Enterococcus faecium, Mycobacterium tuberculosis, Staphylococcus aureus, Staphylococcus pneumoniae, Staphylococcus epidermidis, Staphylococcus saprophyticus, Staphylococcus colmii, Staphylococcus sciuri, Staphylococcus warneri, Streptococcus agalactiae, Streptococcus pyogenes, Streptococcus anginosus, Streptococcus mitis,* or *Streptococcus oralis*. In some embodiments, the gram-negative anaerobe is *Bacteroides fragilis*. In some embodiments, the gram-positive anaerobe is *Clostridium difficile* or *Clostridium perfringens*. In some embodiments, the mycobacterium is *Mycobacterium tuberculosis, Mycobacterium bovis, Mycobacterium africanum, Mycobacterium canetti,* or *Mycobacterium microti*. In some embodiments, the yeast is *Candida albicans* or *Candida krusei*.

The present invention also provides any of the compounds described above for treating a microbial infection.

The present invention also provides any of the compounds described above, or pharmaceutically acceptable salts thereof, for use in the manufacture of a medicament for the treatment of a microbial infection.

The present invention also provides use of any of the compounds described above, or pharmaceutically acceptable salts thereof, for inhibiting growth of a microbe.

The present invention also provides use of any of the compounds described above, or pharmaceutically acceptable salts thereof, for treatment of a microbial infection in a mammal.

DESCRIPTION OF EMBODIMENTS

Figure 1B:
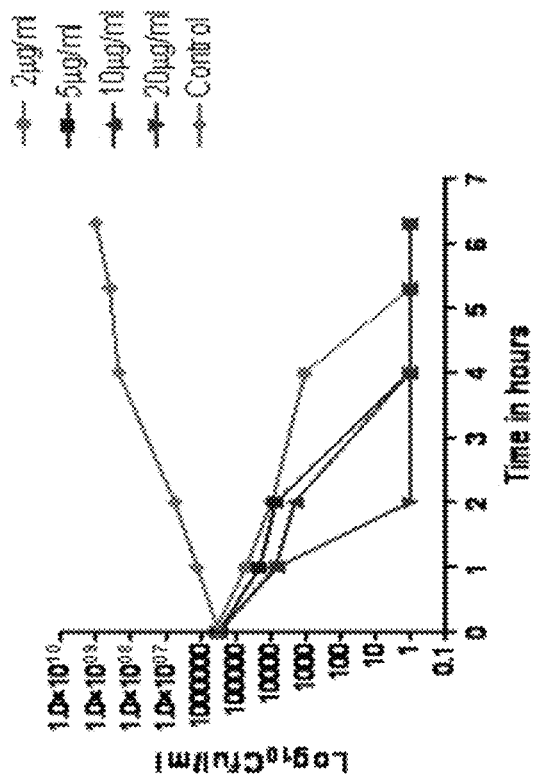
FIG. 1A and FIG. 1B show time-kill studies of Compound A versus *S. aureus* ATCC27660 (FIG. 1B is expanded view of FIG. 1A).

As used herein, the term "about" means ±5% of the value it describes. For example, about 100 means from 95 to 105.

As used herein, the terms "$C_{1-3}$alkyl", "$C_{1-4}$alkyl", and "$(CH_2)_{1-7}$" mean saturated, monovalent unbranched or branched hydrocarbon chains having from 1 to 3 carbons, from 1 to 4 carbons, and from 1 to 7 carbons, respectively. Examples of alkyl groups include, but are not limited to, ($C_1$-$C_7$)alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, and heptyl. An alkyl group can be unsubstituted or substituted with one or two suitable substituents.

As used herein, the terms "$C_{1-3}$alkoxy" and "$C_{1-4}$alkoxy" means —O-alkyl, with alkyl defined as above. An alkoxy group can be unsubstituted or substituted with one or two suitable substituents. The alkyl chain of an alkyloxy group is from 1 to 3 or 1 to 4 carbon atoms in length.

As used herein, the term "halo" means a halogen such as fluorine, chlorine, bromine, or iodine.

As used herein, the terms "halo$C_{1-3}$alkyl" and "halo $C_{1-4}$alkyl" means alkyl groups as defined above, wherein one or more (i.e., 1, 2, 3, 4, 5, 6, 7, 8, 9, or 10) hydrogens are replaced with a halo, as defined above.

As used herein, "isolated" means that the compounds of Formula I are separated from other components of either (a) a natural source, such as a cell, such as a bacterial culture, or (b) a synthetic organic chemical reaction mixture, such as by conventional techniques, the compounds of Formula I are purified.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "microbe" means a bacteria, fungi, protozoa, or virus.

As used herein, the phrase "pharmaceutically acceptable salt(s)" includes, but is not limited to, salts of acidic or basic groups.

As used herein, the term "purified" means that, when isolated, the isolate contains at least 90%, at least 95%, at least 98%, or at least 99% of a compound of Formula I by weight of the isolate.

As used herein, the phrase "suitable substituent" means a group that does not nullify the synthetic or pharmaceutical utility of the compounds of Formula I or the intermediates useful for preparing them. Examples of suitable substituents include, but are not limited to: ($C_1$-$C_4$)alkyl, ($C_1$-$C_4$)alkenyl, ($C_1$-$C_4$)alkynyl, ($C_1$-$C_4$)alkoxy, —CN, —OH, oxo, halo, —NO$_2$, —CO$_2$H, —NH$_2$, —NH(($C_1$-$C_4$)alkyl), —N(($C_1$-$C_4$)alkyl)$_2$, —CHO, —CO(($C_1$-$C_4$)alkyl), and —CO$_2$(($C_1$-$C_4$)alkyl). One of skill in art can readily choose a suitable substituent based on the stability and pharmacological and synthetic activity of the compound of Formula I.

As used herein, the phrase "anti-microbial effective amount" of a compound comprising Formula I is measured by the anti-microbial effectiveness of the compound. In some embodiments, an anti-microbial effective amount inhibits growth of a particular microbe by at least 10%, by at least 20%, by at least 30%, by at least 40%, by at least 50%, by at least 60%, by at least 70%, by at least 80%, by at least 90%, or by at least 95%. In some embodiments, an "anti-microbial effective amount" is also a "therapeutically effective amount" whereby the compound reduces or eliminates at least one harmful effect of a microbe on a mammal.

The present invention provides compounds of Formula I

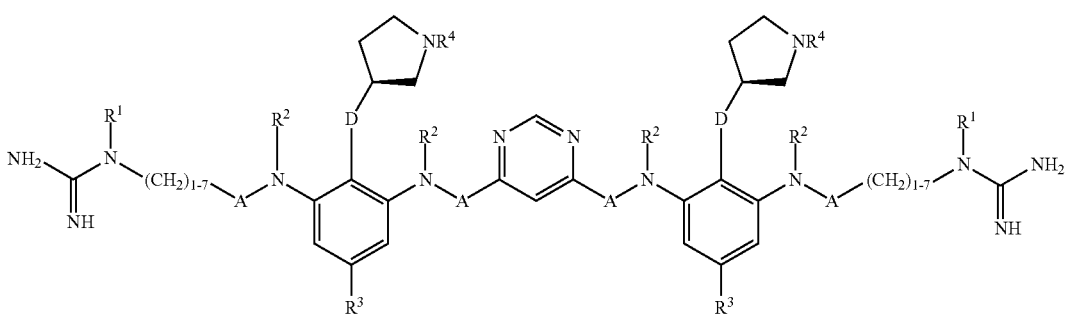

I wherein:
each A is, independently, —C=O, —C=S, or CH$_2$;
each D is, independently, O or S;
each $R^1$ is, independently, hydrogen, $C_{1-3}$alkyl, $C_{1-3}$alkoxy, halo, or halo$C_{1-3}$alkyl;
each $R^2$ is, independently, hydrogen, $C_{1-3}$alkyl, $C_{1-3}$alkoxy, halo, or halo$C_{1-3}$alkyl;
each $R^3$ is, independently, hydrogen, $C_{1-4}$alkyl, $C_{1-4}$alkoxy, halo, or halo$C_{1-4}$alkyl; and
each $R^4$ is, independently, hydrogen, $C_{1-3}$alkyl, $C_{1-3}$alkoxy, halo, or halo$C_{1-3}$alkyl; or a pharmaceutically acceptable salt thereof.

In some embodiments, at least one A is —C=O. In some embodiments, each A is —C=O.

In some embodiments, at least one D is O. In some embodiments, each D is O.

In some embodiments, each $R^1$ is, independently, hydrogen, methyl, ethyl, methoxy, ethoxy, halo, or halo$C_{1-3}$alkyl. In some embodiments, each $R^1$ is, independently, hydrogen, methyl, methoxy, halo, or halo$C_{1-3}$alkyl. In some embodiments, each $R^1$ is, independently, hydrogen, methyl, or methoxy. In some embodiments, at least one $R^1$ is hydrogen. In some embodiments, each $R^1$ is hydrogen.

In some embodiments, each $R^2$ is, independently, hydrogen, methyl, ethyl, methoxy, ethoxy, halo, or halo$C_{1-3}$alkyl.

In some embodiments, each $R^2$ is, independently, hydrogen, methyl, methoxy, or halo. In some embodiments, at least one $R^2$ is hydrogen. In some embodiments, each $R^2$ is hydrogen.

In some embodiments, each $R^3$ is, independently, hydrogen, methyl, ethyl, methoxy, ethoxy, halo, or halo$C_{1-3}$alkyl. In some embodiments, each $R^3$ is, independently, methyl, methoxy, halo, or halo$C_{1-3}$alkyl. In some embodiments, each $R^3$ is, independently, halo or halo$C_{1-3}$alkyl. In some embodiments, each $R^3$ is, independently, halo$C_{1-3}$alkyl. In some embodiments, at least one $R^3$ is trifluoromethyl. In some embodiments, each $R^3$ is trifluoromethyl.

In some embodiments, each $R^4$ is, independently, hydrogen, methyl, ethyl, methoxy, ethoxy, or halo$C_{1-3}$alkyl. In some embodiments, each $R^4$ is, independently, hydrogen, methyl, methoxy, halo, or halo$C_{1-3}$alkyl. In some embodiments, each $R^4$ is, independently, hydrogen, methyl, methoxy, or halo. In some embodiments, at least one $R^4$ is hydrogen. In some embodiments, each $R^4$ is hydrogen.

In some embodiments, each A is, independently, —C=O or —C=S; each D is, independently, O or S; each $R^1$ is, independently, hydrogen, methyl, ethyl, methoxy, ethoxy, halo, halomethyl, or haloethyl; each $R^2$ is, independently, hydrogen, methyl, methoxy, halo, or halomethyl; each $R^3$ is, independently, $C_{1-3}$alkyl, $C_{1-3}$alkoxy, halo, or haloalkyl; and each $R^4$ is, independently, hydrogen, methyl, ethyl, methoxy, ethoxy, halo, halomethyl, or haloethyl.

In some embodiments, each A is, independently, —C=O or —C=S; each D is, independently, O or S; each $R^1$ is, independently, hydrogen, methyl, methoxy, halo, or halomethyl; each $R^2$ is, independently, hydrogen, halo, or halomethyl; each $R^3$ is, independently, methyl, ethyl, methoxy, ethoxy, halo, halomethyl, or haloethyl; and each $R^4$ is, independently, hydrogen, methyl, ethyl, methoxy, ethoxy, halo, halomethyl, or haloethyl.

In some embodiments, each A is —C=O; each D is O; each $R^1$ is, independently, hydrogen, halo, or halomethyl; each $R^2$ is, independently, hydrogen or halo; each $R^3$ is, independently, methyl, methoxy, halo, or halomethyl; and each $R^4$ is, independently, hydrogen, methyl, methoxy, halo, or halomethyl.

In some embodiments, each A is —C=O; each D is O; each $R^1$ is, independently, hydrogen or halo; each $R^2$ is, independently, hydrogen or halo; each $R^3$ is, independently, methyl, halo, or halomethyl; and each $R^4$ is, independently, hydrogen, methyl, halo, or halomethyl.

In some embodiments, each A is —C=O; each D is O; each $R^1$ is, independently, hydrogen or halo; each $R^2$ is, independently, hydrogen or halo; each $R^3$ is, independently, halo or halomethyl; and each $R^4$ is, independently, hydrogen, halo, or halomethyl.

In some embodiments, each A is —C=O; each D is O; each $R^1$ is, independently, hydrogen or halo; each $R^2$ is, independently, hydrogen or halo; each $R^3$ is, independently, methyl, halo, or halomethyl; and each $R^4$ is, independently, hydrogen, methyl, halo, or halomethyl.

In some embodiments, the compound is Compound A

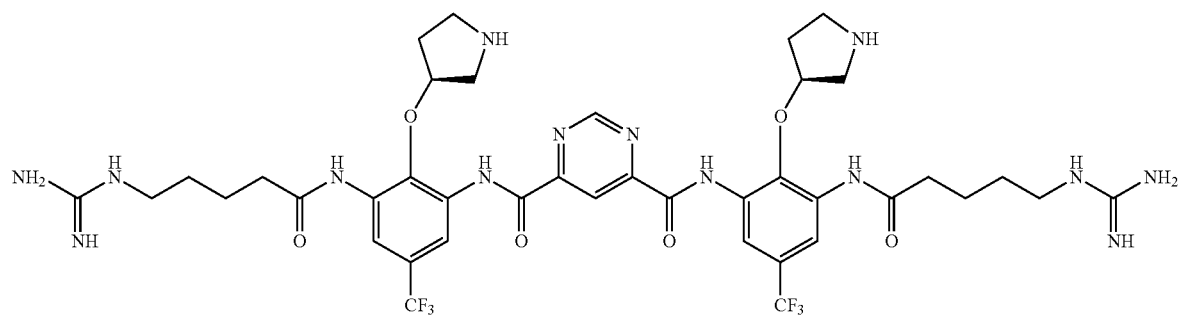 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3O[C@H]3CCNC3)ncn2)c1O[C@H]1CCNC1]

or a pharmaceutically acceptable salt thereof.

Suitable examples of salts include, for example, hydrochloric acid and triflouroacetic acid.

The compounds of Formula I can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of Formula I, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

Compounds of Formula I further include hydrates and solvates.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

In some embodiments, the compounds of Formula I are isolated and/or purified.

The present invention also provides pharmaceutical compositions comprising one or more of the compounds described above, or one or more salts thereof, and a pharmaceutically acceptable carrier.

Suitable compositions include, but are not limited to, oral non-absorbed compositions. Suitable compositions also include, but are not limited to saline, water, cyclodextrin solutions, and buffered solutions of pH 3-9.

The compounds described herein, including Compound A, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the excipient is a multi-component system chosen from 20% w/v propylene glycol in saline, 30% w/v propylene glycol in saline, 40% w/v propylene glycol in saline, 50% w/v propylene glycol in saline, 15% w/v propylene glycol in purified water, 30% w/v propylene glycol in purified water, 50% w/v propylene glycol in purified water, 30% w/v propylene glycol and 5 w/v ethanol in purified water, 15% w/v glycerin in purified water, 30% w/v glycerin in purified water, 50% w/v glycerin in purified water, 20% w/v Kleptose in purified water, 40% w/v Kleptose in purified water, and 25% w/v Captisol in purified water. In some embodiments, the excipient is chosen from 50% w/v propylene glycol in purified water, 15% w/v glycerin in purified water, 20% w/v Kleptose in purified water, 40% w/v Kleptose in purified water, and 25% w/v Captisol in purified water. In some embodiments, the excipient is chosen from 20% w/v Kleptose in purified water, 20% w/v propylene glycol in purified water, and 15% w/v glycerin in purified water.

In some embodiments, the formulation comprises 50 mg/mL Compound A in 20% w/v Kleptose in purified water.

In some embodiments, the formulation can be lyophilized to a solid and reconstituted with, for example, water prior to use.

When administered to a mammal (e.g., to an animal for veterinary use or to a human for clinical use) the compounds of Formula I can be administered in isolated form. Alternately, the compounds of Formula I can be administered along with (i.e., as a combined formulation or as separate formulations) with other antibiotics, such as, for example: 1) protein synthesis inhibitors including, but not limited to, amikacin, anisomycin, apramycin, azithromycin, blasticidine S, brefeldin A, butirosin, chloramphenicol, chlortetracycline, clindamycin, clotrimazole, cycloheximide, demeclocycline, dibekacin, dihydrostreptomycin, doxycycline, duramycin, emetine, erythromycin, fusidic acid, G 418, gentamicin, helvolic acid, hygromycin B, josamycin, kanamycin, kirromycin, lincomycin, meclocycline, mepartricin, midecamycin, minocycline, neomycin, netilmicin, nitrofurantoin, nourseothricin, oleandomycin, oxytetracycline, paromomycin, puromycin, rapamycin, ribostamycin, rifampicin, rifamycin, rosamicin, sisomicin, spectinomycin, spiramycin, streptomycin, tetracycline, thiamphenicol, thiostrepton, tobramycin, tunicamycin, tylosin, viomycin, and virginiamycin; 2) DNA synthesis interfering agents including, but not limited to, camptothecin, 10-deacetylbaccatin III, azacytidine, 7-aminoactinomycin D, 8-quinolinol, 9-dihydro-13-acetylbaccatin III, aclarubicin, actinomycin D, actinomycin I, actinomycin V, bafilomycin A1, bleomycin, capreomycin, chromomycin, cinoxacin, ciprofloxacin, cis-diammineplatinum(II) dichloride, coumermycin A1, L(+)-lactic acid, cytochalasin B, cytochalasin D, dacarbazine, daunorubicin, distamycin A, doxorubicin, echinomycin, enrofloxacin, etoposide, flumequine, formycin, fumagillin, ganciclovir, gliotoxin, lomefloxacin, metronidazole, mithramycin A, mitomycin C, nalidixic acid, netropsin, nitrofurantoin, nogalamycin, nonactin, novobiocin, ofloxacin, oxolinic acid, paclitaxel, phenazine, phleomycin, pipemidic acid, rebeccamycin, sinefungin, streptonigrin, streptozocin, succinylsulfathiazole, sulfadiazine, sulfadimethoxine, sulfaguanidine purum, sulfamethazine, sulfamonomethoxine, sulfanilamide, sulfaquinoxaline, sulfasalazine, sulfathiazole, trimethoprim, tubercidin, 5-azacytidine, cordycepin, and formycin A; 3) cell wall synthesis interfering agents including, but not limited to, (+)-6-aminopenicillanic acid, 7-Aminodesacetoxycephalosporanic acid, amoxicillin, ampicillin, azlocillin, bacitracin, carbenicillin, cefaclor, cefamandole, cefazolin, cefmetazole, cefoperazone, cefotaxime, cefsulodin, ceftriaxone, cephalexin, cephalosporin C, cephalothin, cephradine, cloxacillin, D-cycloserine, dicloxacillin, D-penicillamine, econazole, ethambutol, lysostaphin, moxalactam, nafcillin, nikkomycin Z, nitrofurantoin, oxacillin, penicillic, penicillin G, phenethicillin, phenoxymethylpenicillinic acid, phosphomycin, pipemidic acid, piperacillin, ristomycin, and vancomycin; 4) cell membrane permeability interfering agents (ionophores) including, but not limited to, 2-mercaptopyridine, 4-bromocalcimycin A23187, alamethicin, amphotericin B, calcimycin A23187, chlorhexidine, clotrimazole, colistin, econazole, hydrocortisone, filipin, gliotoxin, gramicidin A, gramicidin C, ionomycin, lasalocid A, lonomycin A, monensin, N-(6-aminohexyl)-5-chloro-1-naphthalenesulfonamide, narasin, nigericin, nisin, nonactin, nystatin, phenazine, pimaricin, polymyxin B, DL-penicillamine, polymyxin B, praziquantel, salinomycin, surfactin, and valinomycin; 5) enzyme inhibitors including, but not limited to, (+)-usnic acid, (±)-miconazole, (S)-(+)-camptothecin, 1-deoxymannojirimycin, 2-heptyl-4-hydroxyquinoline N-oxide, cordycepin, 1,10-phenanthroline, 6-diazo-5-oxo-L-norleucine, 8-quinolinol, antimycin, antipain, ascomycin, azaserine, bafilomycin, cerulenin, chloroquine, cinoxacin, ciprofloxacin, mevastatin, concanamycin A, concanamycin C, coumermycin A1, L(+)-lactic acid, cyclosporin A, econazole, enrofloxacin, etoposide, flumequine, formycin A, furazolidone, fusaric acid, geldanamycin, gliotoxin, gramicidin A, gramicidin C, herbimycin A, indomethacin, irgasan, lomefloxacin, mycophenolic acid, myxothiazol, N-(6-aminohexyl)-5-chloro-1-naphthalenesulfonamide, nalidixic acid, netropsin, niclosamide, nikkomycin, N-methyl-1-deoxynojirimycin, nogalamycin, nonactin, novobiocin, ofloxacin, oleandomycin, oligomycin, oxolinic acid, piericidin A, pipemidic acid, radicicol, rapamycin, rebeccamycin, sinefungin, staurosporine, stigmatellin, succinylsulfathiazole, succinylsulfathiazole, sulfadiazine, sulfadimethoxine, sulfaguanidine, sulfamethazine, sulfamonomethoxine, sulfanilamide, sulfaquinoxaline, sulfasalazine, sulfathiazole, triacsin C, trimethoprim, and vineomycin A1; and 6) membrane modifiers including, but not limited to, paracelsin.

In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, or excipient with which a compound of Formula I is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used. When administered to a human, the compounds of Formula I and pharmaceutically acceptable carriers can be sterile. Water is a suitable carrier when the compound of Formula I is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A.R. Gennaro (Editor) Mack Publishing Co.

In one embodiment, the compounds of Formula I are formulated in accordance with routine procedures as a pharmaceutical composition adapted for administration to humans. Typically, compounds of Formula I are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of Formula I is administered by injection, an ampoule of sterile water for injection or saline can be provided so that the ingredients may be mixed prior to administration.

The compounds of Formula I, and compositions comprising the same, can be administered orally. Compounds and compositions for oral delivery can be in the form of, for example, tablets, lozenges, aqueous or oily suspensions, granules, powders, emulsions, capsules, syrups, or elixirs. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of Formula I. Oral compositions can include standard vehicles such as mannitol, lactose, starch, magnesium stearate, sodium saccharine, cellulose, magnesium carbonate, etc. Such vehicles are suitably of pharmaceutical grade.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

The present invention also provides methods of preparing Compound A comprising:

1a) reacting (R)-(−)-N-Boc-3-pyrrolidinol with a strong base to form a mixture; further reacting the mixture with 2-chloro-5-(trifluoromethyl)-1,3-dinitrobenzene to form a compound having Formula II

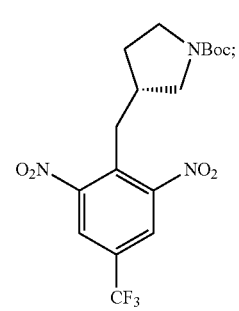

1b) reacting the compound of Formula II with an alcohol and a transition metal catalyst in the presence of hydrogen to form a compound of Formula III

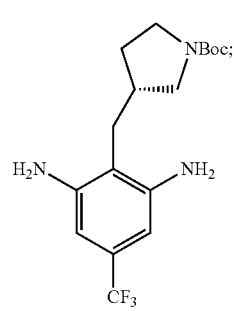

1c) adding the compound of Formula III and pyrimidine-4,6-dicarboxylic acid to a mixture of 2-chloro-4,6-dimethoxy-1,3,5-triazine and N-methylmorpholine to form a compound of Formula IV

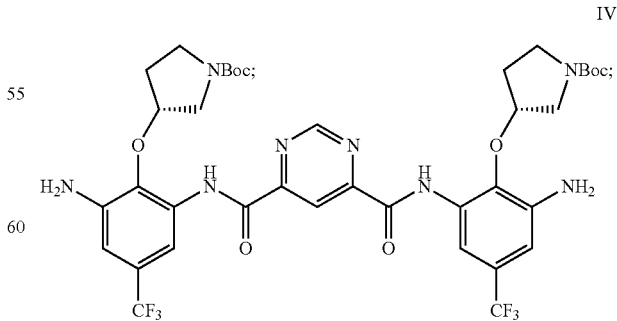

1d) reacting the compound of Formula IV with N-Boc-guanidine butyric acid to form a compound of Formula V

V

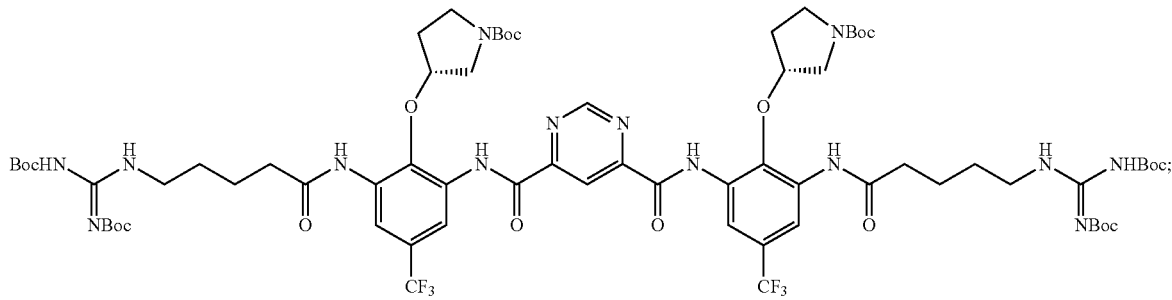

and 1e) deprotecting the compound of Formula V to produce Compound A.

In some embodiments, in a) the strong base is NaH; and in b) the transition metal catalyst is Pd/C and the alcohol is ethanol. In particular, this method is described below in more detail in Example 1.

The present invention also provides alternate methods of preparing Compound A comprising:

a) deprotonating (R)-3-Hydroxypyrrolidine-1-carboxylic acid tert-butyl ester, and reacting the resultant compound with 2-chloro-1,3-dinitro-5-trifluoromethylbenzene to form (R)-3-(2,6-dinitro-4-trifluoromethylphenoxy)pyrrolidine-1-carboxylic acid tert-butyl ester;

b) reducing (R)-3-(2,6-dinitro-4-trifluoromethylphenoxy)pyrrolidine-1-carboxylic acid tert-butyl ester in the presence of an alcohol, a transition metal catalyst, and hydrogen to form (R)-3-(2,6-diamino-4-trifluoromethylphenoxy)-pyrrolidine-1-carboxylic acid tert-butyl ester;

c) coupling (R)-3-(2,6-diamino-4-trifluoromethylphenoxy)-pyrrolidine-1-carboxylic acid tert-butyl ester with pyrimidine-4,6-dicarboxylic acid in the presence of 1-[(3-(dimethylamino)-propyl)]-3-ethylcarbodiimide hydrochloride to form pyrimidine-4,6-dicarboxylic acid bis-{[3-amino-2-((R)-1-(tert-butoxycarbonyl)pyrrolidin-3-yloxy)-5-trifluoromethyl-phenyl]amide};

d) reacting pyrimidine-4,6-dicarboxylic acid bis-{[3-amino-2-((R)-1-(tert-butoxycarbonyl)pyrrolidin-3-yloxy)-5-trifluoromethyl-phenyl]amide} with ({[(tert-butoxycarbonyl)amino][(tert-butoxycarbonyl)imino]methyl}amino)pentanoic acid in the presence of phosphorous oxychloride to form pyrimidine-4,6-dicarboxylic acid bis-{[3-(5-({[(tert-butoxycarbonyl)amino][(tert-butoxycarbonyl)imino]methyl}amino)-pentanoylamino)-2-((R)-1-(tert-butoxycarbonyl)-pyrrolidin-3-yloxy)-5-trifluoromethyl-phenyl]-amide};

e) deprotecting pyrimidine-4,6-dicarboxylic acid bis-{[3-(5-({[(tert-butoxycarbonyl)amino][(tert-butoxycarbonyl)imino]methyl}amino)-pentanoylamino)-2-((R)-1-(tert-butoxycarbonyl)-pyrrolidin-3-yloxy)-5-trifluoromethyl-phenyl]-amide} to form crude pyrimidine-4,6-dicarboxylic acid bis-{[3-(5-guanidino-pentanoylamino)-2-((R)-pyrrolidin-3-yloxy)-5-trifluoromethyl-phenyl]-amide}tetrahydrochloride; and f) purifying crude pyrimidine-4,6-dicarboxylic acid bis-{[3-(5-guanidino-pentanoylamino)-2-((R)-pyrrolidin-3-yloxy)-5-trifluoromethyl-phenyl]-amide}tetrahydrochloride by reverse-phase chromatography.

In some embodiments, in b) the transition metal catalyst is Pd/C and the alcohol is ethanol. In particular, this method is described below in more detail in Example 2.

The present invention also provides second alternate methods of preparing Compound A comprising:

a) deprotonating (R)-3-Hydroxypyrrolidine-1-carboxylic acid tert-butyl ester and further reacting the resultant compound with 2-chloro-1,3-dinitro-5-trifluoromethylbenzene to form (R)-3-(2,6-dinitro-4-trifluoromethylphenoxy)pyrrolidine-1-carboxylic acid tert-butyl ester;

b) reducing (R)-3-(2,6-dinitro-4-trifluoromethylphenoxy)pyrrolidine-1-carboxylic acid tert-butyl ester in the presence of an alcohol, a transition metal catalyst, and hydrogen, to form (R)-3-(2,6-diamino-4-trifluoromethylphenoxy)-pyrrolidine-1-carboxylic acid tert-butyl ester;

c) coupling (R)-3-(2,6-diamino-4-trifluoromethylphenoxy)-pyrrolidine-1-carboxylic acid tert-butyl ester with pyrimidine-4,6-dicarboxylic acid in the presence of 1-[(3-(dimethylamino)-propyl)]-3-ethylcarbodiimide hydrochloride to form pyrimidine-4,6-dicarboxylic acid bis-{[3-amino-2-((R)-1-(tert-butoxycarbonyl)pyrrolidin-3-yloxy)-5-trifluoromethyl-phenyl]amide};

d) reacting pyrimidine-4,6-dicarboxylic acid bis-{[3-amino-2-((R)-1-(tert-butoxycarbonyl)pyrrolidin-3-yloxy)-5-trifluoromethyl-phenyl]amide} with N-Cbz acid in the presence of thionyl chloride;

e) reducing the resultant compound of d) in the presence of an alcohol, a transition metal catalyst, and hydrogen;

f) reacting the resultant compound of e) with di-Boc pyrazole; and g) deprotecting the resultant compound of f) to produce Compound A.

In some embodiments, in b) and e) the transition metal catalyst is Pd/C and the alcohol is ethanol. In particular, this method is described below in more detail in Example 3.

One skilled in the art will be able to substitute suitable reagents for the reagents recited in the methods described herein to produce Compound A as well as additional compounds of Formula I.

The present invention also provides methods of preparing a pharmaceutically acceptable salt of Compound A comprising:

a) reacting (R)-(−)-N-Boc-3-pyrrolidinol with a strong base to form a mixture; further reacting the mixture with 2-chloro-5-(trifluoromethyl)-1,3-dinitrobenzene to form a compound having Formula II

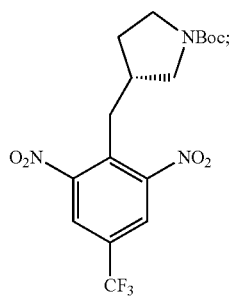

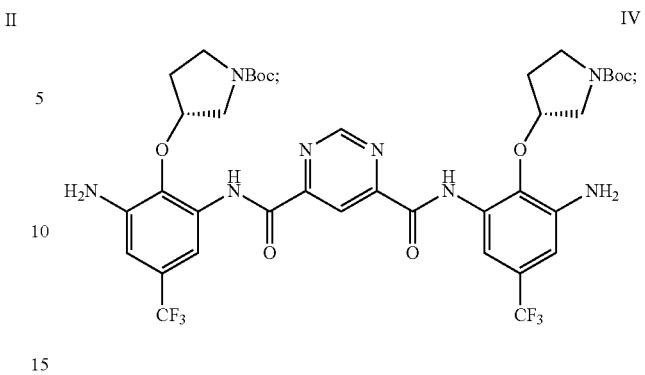

b) reacting the compound of Formula II with an alcohol and a transition metal catalyst in the presence of hydrogen to form a compound of Formula III or c2) adding the compound of Formula III and pyrimidine-4,6-dicarboxylic acid to a mixture of 1-ethyl-3-[3-(dimethylamino)propyl]-carbodiimide hydrochloride (EDCl) and anhydrous pyridine to form a compound of Formula IV

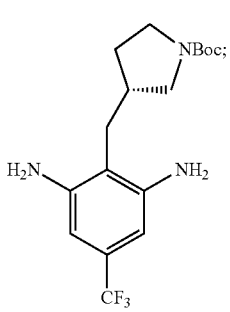

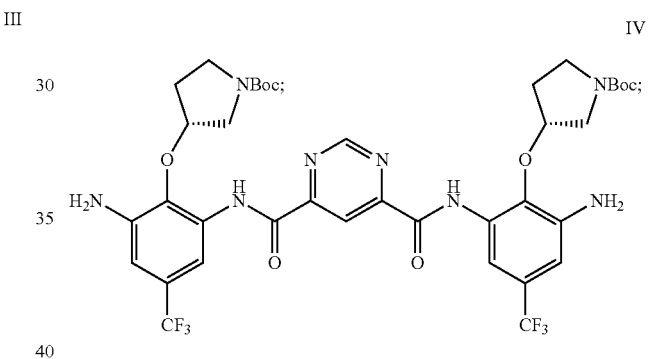

c1) adding the compound of Formula III and pyrimidine-4,6-dicarboxylic acid to a mixture of 2-chloro-4,6-dimethoxy-1,3,5-triazine and N-methylmorpholine to form a compound of Formula IV d) adding the compound of Formula IV with an N-Cbz acid to a solution comprising anhydrous pyridine, dimethylaminopropylamine, and any one of thionyl chloride, POCl$_3$, (EtO)$_2$POCl, or oxalyl chloride to form a compound of Formula Va

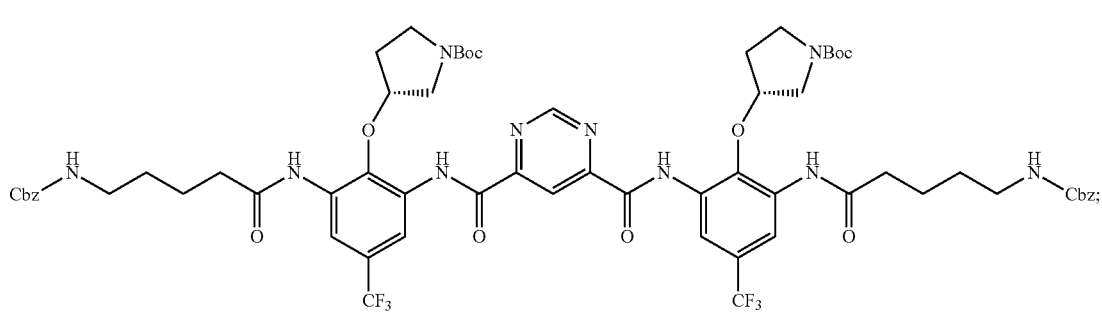

e) hydrogenlysis of the Cbz group of the compound of Formula Va to produce the compound of formula VI

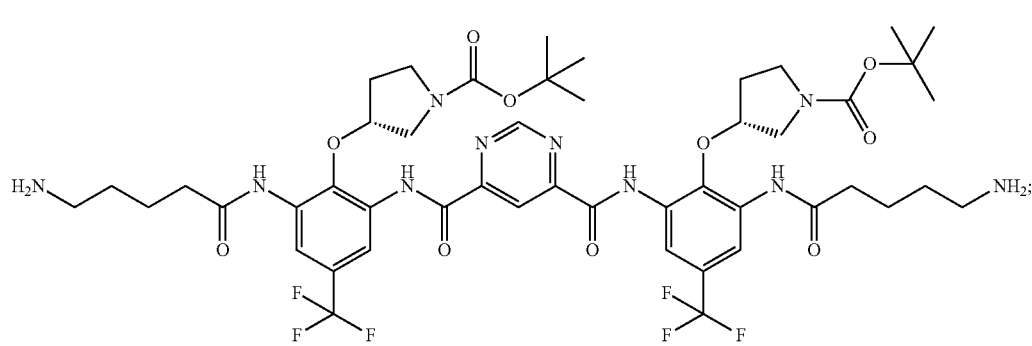

f) protecting the compound of Formula VI to produce the compound of formula VII

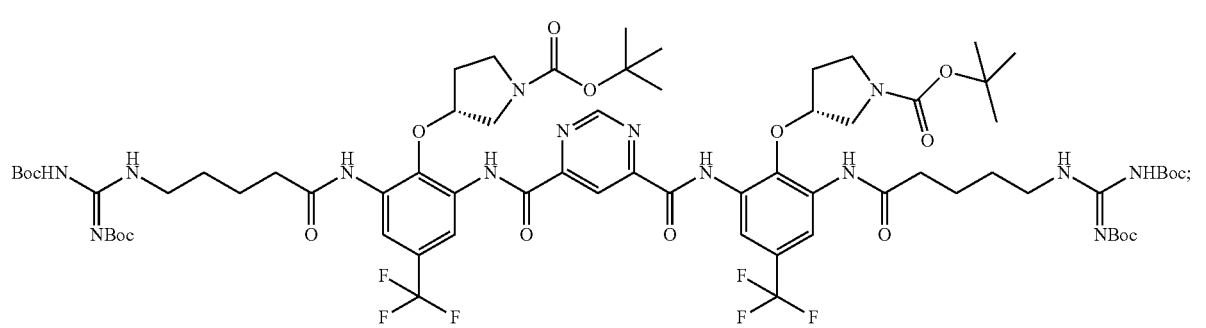

and g) deprotecting the compound of Formula VII to produce a pharmaceutically acceptable salt of Compound A.

Preparation of compounds of Formula I can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

The present invention also provides methods of inhibiting the growth of a microbe comprising contacting the microbe with one or more compounds described above, or a pharmaceutically acceptable salt thereof. In some embodiments, the compound of Formula I can act as an antiseptic agent for cleansing surfaces, such as in, for example, kitchens and bathrooms. In these embodiments, the compound of Formula I can be formulated for such uses by procedures well known to the skilled artisan.

The present invention also provides methods of treating a mammal having a microbial infection comprising administering to the mammal in need thereof an anti-microbial effective amount of one or more compounds described above, or a pharmaceutically acceptable salt thereof. In some embodiments, the mammal can be pre-diagnosed with a microbial infection prior to treatment. In some embodiments, no formal diagnosis may have been made; in such embodiments, the mammal may be suspected of having a microbial infection for which treatment is recognized as being desirable.

In one embodiment, "treatment" or "treating" refers to an amelioration of a microbial infection, or at least one discernible symptom thereof; or to an amelioration of at least one measurable physical parameter, not necessarily discernible by the patient; or to inhibiting the progression of a microbial infection; or to delaying the onset of a microbial infection.

In some embodiments, the microbe is, or the microbial infection is due to, a gram-negative aerobe, a gram-positive aerobe, a gram-negative anaerobe, a gram-positive anaerobe, or a yeast. In some embodiments, the gram-negative aerobe is selected from, but not limited to, *Escherichia coli, Citrobacter freundii, Citrobacter diverus, Citrobacter koseri, Enterobacter cloacae, Enterobacter faecalis, Klebsiella pneumonia, Klebsiella oxytoca, Morganella morganii, Providencia stuartii, Proteus vulgaris, Proteus mirabilis, Serratia marcescens, Acinetobacter haemolyticus, Acinetobacter junii, Acinetobacter lwoffii, Haemophilus influenzae, Stenotrophomonas maltophilia*, and *Pseudomonas aeruginosa*. In some embodiments, the gram-positive aerobe is selected from, but not limited to, *Enterococcus faecalis, Enterococcus faecium, Mycobacterium tuberculosis, Staphylococcus aureus, Staphylococcus pneumoniae, Staphylococcus epidermidis, Staphylococcus saprophyticus, Staphylococcus colmii, Staphylococcus sciuri, Staphylococcus warneri, Streptococcus agalactiae, Streptococcus pyogenes, Streptococcus anginosus, Streptococcus mitis*, and *Streptococcus oralis*. In some embodiments, the gram-negative anaerobe is *Bacteroides fragilis*. In some embodiments, the gram-positive anaerobe is *Clostridium difficile* or *Clostridium perfringens*. In some embodiments, the mycobacterium is *Mycobacterium tuberculosis, Mycobacterium bovis, Myco-*

*bacterium africanum, Mycobacterium canetti,* or *Mycobacterium microti.* In some embodiments, the yeast is selected from, but not limited to, *Candida albicans* and *Candida krusei.*

In some embodiments, the microbe is an antibiotic-resistant strain of bacteria, such as those recited in the Examples below.

The compounds of Formula I, or a pharmaceutically acceptable salt thereof, and compositions comprising the same, can be administered in a variety of routes, such as, for example, by infusion or bolus injection, and can be administered together with another biologically active agent, such as another antibiotic. Administration can be systemic or local. Various delivery systems are known, e.g., encapsulation in liposomes, microparticles, microcapsules, capsules, etc., and can be used to administer a compound of Formula I. Routes of administration include, but are not limited to, intradermal, intramuscular, intraperitoneal, intravenous, subcutaneous, intranasal, epidural, oral, sublingual, intranasal, intracerebral, intravaginal, transdermal, rectally, pulmonary, by inhalation, or topically, particularly to the ears, nose, eyes, or skin. In some embodiments, suitable routes of administration include intravenous, topical, and subcutaneous. The desired route of administration is left to the discretion of the practitioner, and will depend, in part, upon the site of the microbial infection and medical condition of the mammal or human being treated. In most instances, administration can result in the release of the compounds of Formula I into the bloodstream.

In some embodiments, it may be desirable to administer one or more compounds of Formula I, or a pharmaceutically acceptable salt thereof, locally to an area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, wherein the implant is of a porous, non-porous, or gelatinous material, including membranes, such as sialastic membranes, or fibers.

The amount of a compound of Formula I, or a pharmaceutically acceptable salt thereof, that will be effective in the treatment of a particular microbial infection will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the infection, and should be decided according to the judgment of the practitioner and each patient's circumstances. However, suitable dosage ranges for administration are generally about 0.001 milligrams to about 200 milligrams per kilogram of body weight. In some embodiments, the dose is from about 0.01 milligrams to about 70 milligrams per kilogram of body weight, or from about 0.1 milligrams to about 50 milligrams per kilogram of body weight, or from about 0.5 milligrams to about 20 milligrams per kilogram of body weight, or from about 1 milligram to about 10 milligrams per kilogram of body weight. In some embodiments, the dose is about 5 milligrams per kilogram of body weight. The dosage amounts described herein refer to total amounts administered; that is, if more than one compound of Formula I is administered, the dosages correspond to the total amount of the compounds of Formula I administered. Compositions can contain 10% to 95% active ingredient by weight. Effective doses can be extrapolated from dose-response curves derived from in vitro or animal model test systems. Such animal models and systems are well known in the art.

The present invention also provides one or more compounds described above, or a pharmaceutically acceptable salt thereof, or a pharmaceutical composition comprising one or more compounds described above, for treating a microbial infection.

The present invention also provides one or more compounds described above, or a pharmaceutically acceptable salt thereof, or a pharmaceutical composition comprising one or more compounds described above, for use in the manufacture of a medicament for the treatment of a microbial infection.

The present invention also provides the use of one or more compounds described above, or a pharmaceutically acceptable salt thereof, or a pharmaceutical composition comprising one or more compounds described above, in the inhibition of growth of a microbe.

The present invention also provides the use of one or more compounds described above, or a pharmaceutically acceptable salt thereof, or a pharmaceutical composition comprising one or more compounds described above, in the treatment of a microbial infection in a mammal.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Briefly, the results generated from the examples below indicate that Compound A is active against *Staphylococci* spp. and other Gram-positive and Gram-negative organisms. For example, susceptibility screens were performed against 150 isolates of *S. aureus* and coagulase-negative *Staphylococci* with defined antibacterial susceptibilities to other antimicrobials. Generally, $MIC_{90}$ values of 0.5 to 2.0 µg/ml have been obtained in a screen of 150 *Staphylococci* organisms, and was not affected by susceptibility phenotypes to other antibiotics. Serial passage of methicillin-susceptible (MSSA ATCC 29213) and resistant (MRSA ATCC 33591) strains of *S. aureus* at 0.5× MIC concentrations for 17 passages did not result in any change in MIC values. Generally, Compound A was bactericidal with time-kills ranging from 30 minutes to 6 hours.

Compound A was efficacious in vivo in a mouse thigh burden model against MSSA 29213 and MRSA 33591 and in a mouse peritonitis/sepsis model against MSSA 27660. In the mouse thigh burden model with MSSA 27660, Compound A achieved reductions 24 hours post-infection of up to $4^{10}$ in cfu/thigh relative to untreated, infected control mice at dosages that were well-tolerated in repeat dose toxicity studies. Thus, robust efficacy against MSSA and MRSA was observed in a mouse thigh burden model, and against MSSA in a rat thigh burden model and a mouse peritonitis model. Compound A was stable in the presence of plasma and isolated hepatocytes from multiple species.

Compound A was better tolerated in acute toxicity studies when administered by IV infusion. The MTD (IV bolus) for Compound A in the mouse (30 mg/kg) is significantly higher than the static efficacy dose in the thigh burden model (2-4 mg/kg).

Compound A is currently in Phase 1 human clinical trials for development as an IV pan-Staphylococcal agent.

Example 1

Synthesis of Compound A

Step 1:

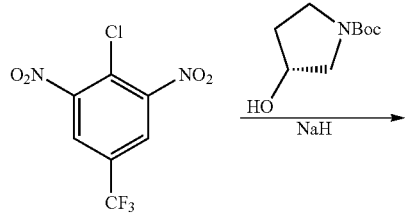

Sodium hydride (1.12 g, 60% in mineral oil, 28 mmol) was added in portion to anhydrous DMF (24 mL) solution of (R)-(−)-N-Boc-3-pyrrolidinol (5.0 g, 27.6 mmol) at room temperature. The resulting mixture was stirred for an additional 15 minutes. This mixture was then added dropwise to a DMF (20 mL) solution of 2-chloro-5-(trifluoromethyl)-1,3-dinitrobenzene (7.45 g, 27.6 mmol) at 0° C. The deep red solution was stirred at room temperature for 4 hours. The reaction was quenched by ice-water and extracted by ethyl acetate. The organic layer was washed by brine and water, and dried over $Na_2SO_4$. After removal of the solvent, the residue was purified by flash column (ethyl acetate/hexanes=¼, v/v). The yield was 54%.

Step 2:

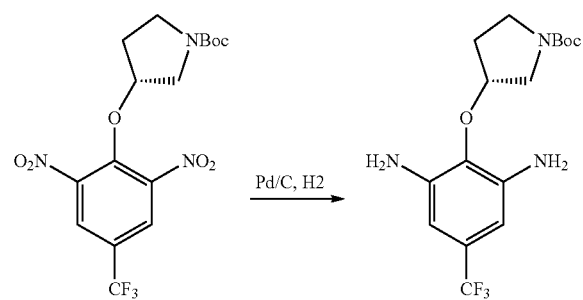 [SMILES: CC(C)(C)OC(=O)N1CC[C@@H](Oc2c([N+](=O)[O-])cc(C(F)(F)F)cc2[N+](=O)[O-])C1 ; CC(C)(C)OC(=O)N1CC[C@@H](Oc2c(N)cc(C(F)(F)F)cc2N)C1]

(R)-tert-butyl 3-(4-(trifluoromethyl)-2,6-dinitrophenoxy)pyrrolidine-1-carboxylate (4.84 g, 9.8 mmol) and Pd/C (0.78 g, 10% on carbon) and ethanol (140 mL) were placed in a Parr bottle. The mixture was flashed under hydrogen three times and stirred under 40 psi hydrogen at room temperature overnight. The mixture was filtrated through celite. The cake was washed twice with ethanol (2×20 mL). The filtrate was evaporated under vacuum. An off-white solid was obtained and used as such for the subsequent reaction. The yield was 100%.

Step 3:

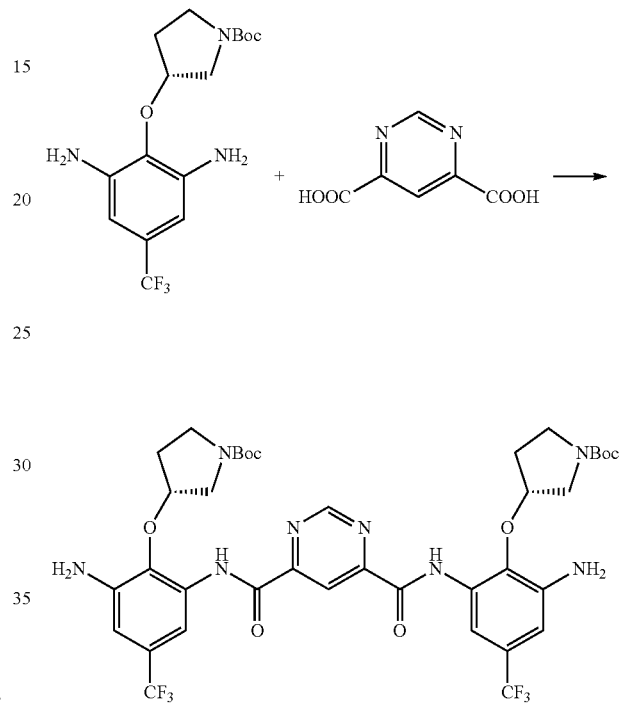

2-Chloro-4,6-dimethoxy-1,3,5-triazine (5.97 g, 34 mmol) was stirred in anhydrous THF (200 mL). N-Methylmorpholine (7.5 ml, 68 mmol) was added. The resulting mixture was stirred at room temperature for 30 minutes. Then, (R)-tert-butyl 3-(2,6-diamino-4-(trifluoromethyl)phenoxy)pyrrolidine-1-carboxylate (10.84 g, 30 mmol) and pyrimidine-4,6-dicarboxylic acid (2.48 g, 14.8 mmol) were added. The mixture was stirred at room temperature for 24 hours. The solvent was evaporated completely in vacuum. Water (250 mL) was added and the mixture was stirred for 4 hours. After filtration, the yellow cake was washed with water (3×100 mL) and stirred in water (250 mL) for 4 hours. The filtration and washing procedure was repeated twice. The solid was dried in the air and stirred in dichloromethane (20 mL) for 30 minutes, followed by ultrasonic treatment for 1 hour. After filtration, the yellow cake was quickly washed with cold dichloromethane (2×10 mL). The product (10.0 g, yield: 79.1%) was used as such for subsequent reaction.

Step 4:

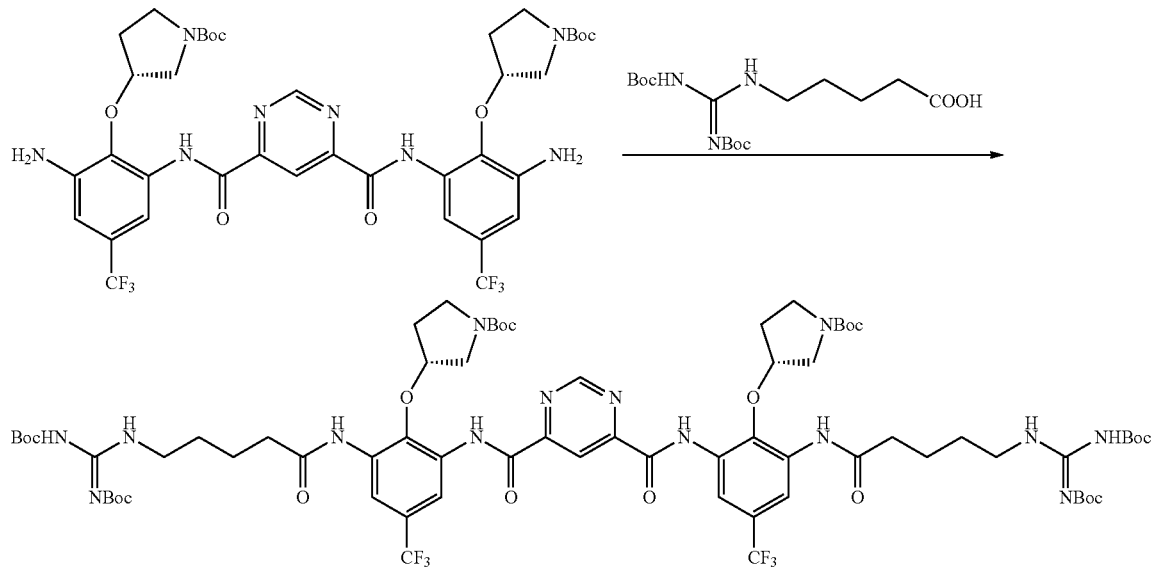

The starting material (6.5 g, 7.6 mmol), N-Boc guanidine butyric acid (10.9 g, 30.4 mmol) were stirred in anhydrous pyridine (40 mL) at 0° C. POCl₃ (2.78 mL, 30.4 mmol) in pyridine (4 mL) was added dropwise. The resulting mixture was stirred at 0° C. for 1.5 hours. The reaction mixture was evaporated under vacuum. Water (140 mL) was added to the residue. The mixture was extracted with ethyl acetate (260 mL). The organic layer was washed with brine (100 mL) and dried over Na₂SO₄. After evaporation, the residue was purified by column (Eluent: ethyl acetate/hexanes/dichloromethane=1/1/1, v/v/v then 2%~4% methanol in dichloromethane). The yield was 29.1%. The R$_f$ was same as the standard sample which was characterized by NMR.

Step 5:

The starting material (3.4 g, 2.3 mmol) was stirred in 4N HCl in dioxane (34 mL) at room temperature overnight. The solvent was removed under vacuum. The residue was titrated in ether. The solid was filtered and purified by C18 reverse-phase C18 column. A light yellow solid was obtained as product with a purity of 98% (HPLC); LC-MS (M+1): 937. Yield: 51%.

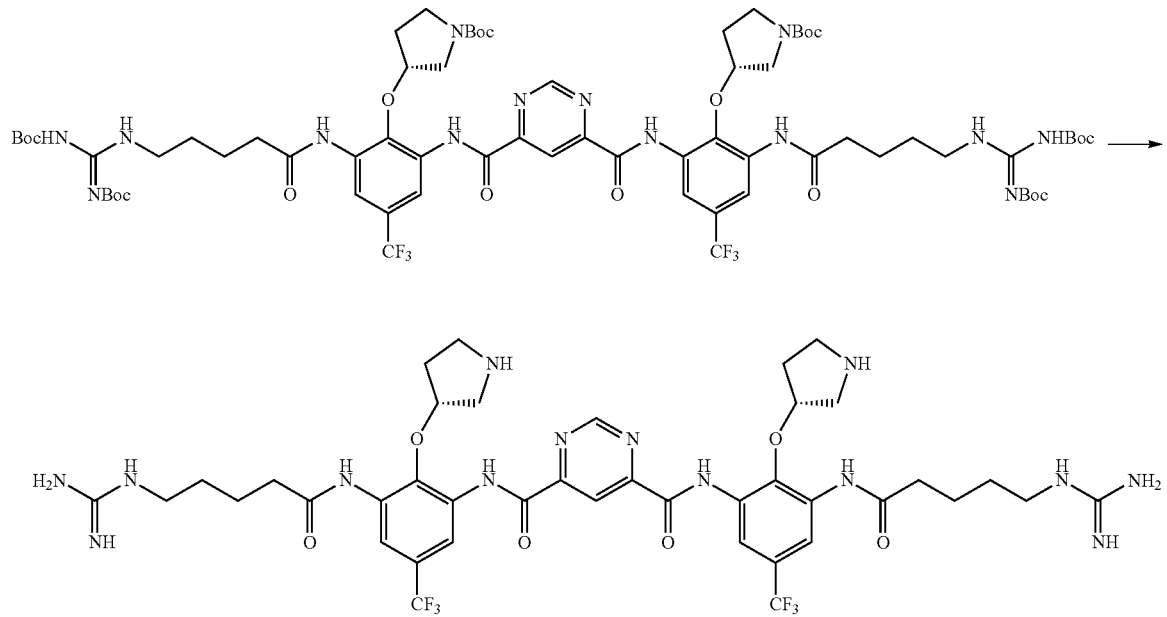

Example 2
Synthesis Of Compound A
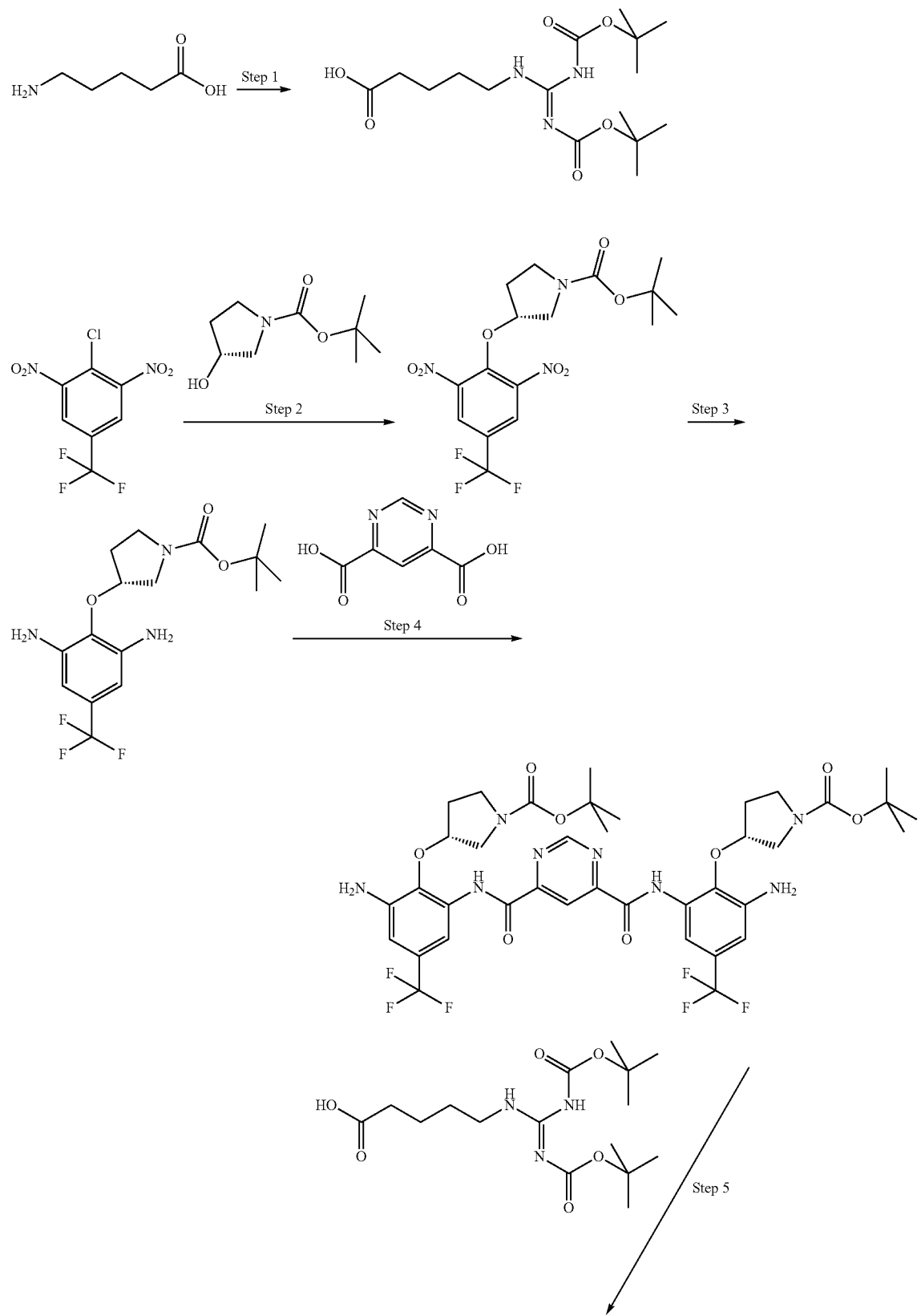

-continued

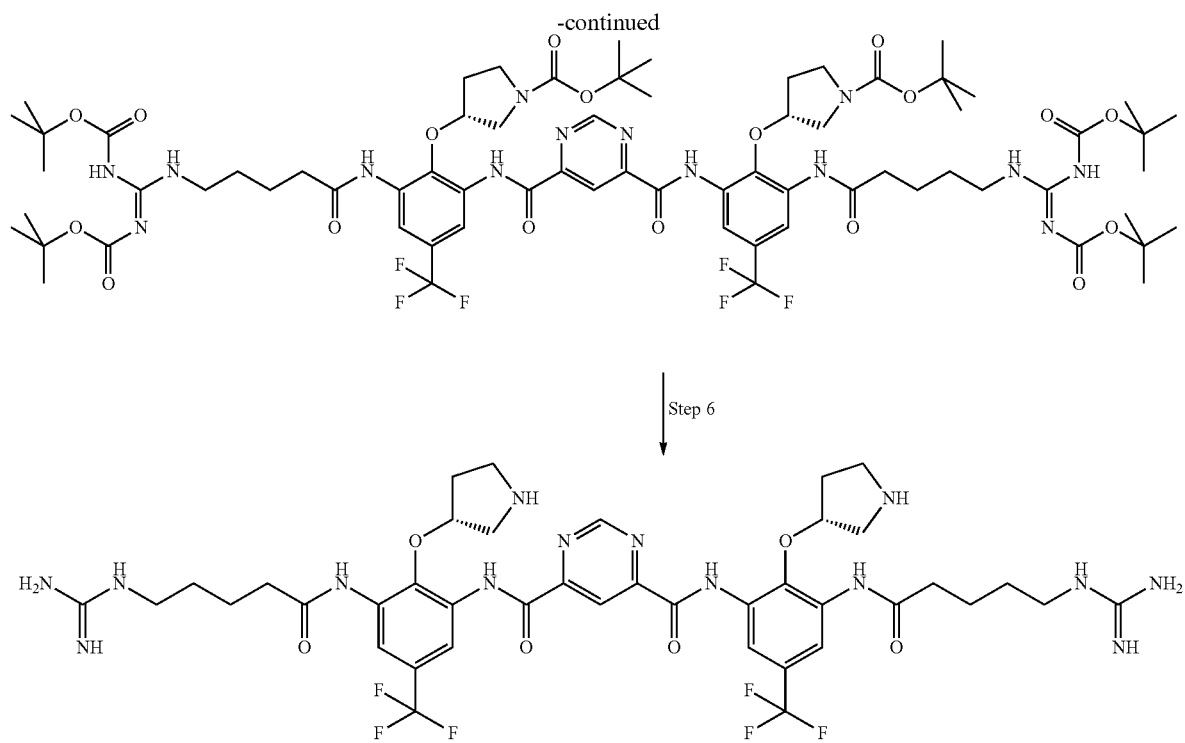

↓ Step 6

Step 1: (R)-3-hydroxypyrrolidine-1-carboxylic acid tert-butyl ester is de-protonated with potassium tert-butoxide (KOtBu) in tetrahydrofuran (THF). The resulting anion is reacted with 2-chloro-1,3-dinitro-5-trifluoromethylbenzene in tert-butyl methyl ether (MTBE)/THF. When the reaction is complete, the reaction mixture is quenched with water and partitioned with more MTBE. The organic layer is washed with brine and water and concentrated on a rotary evaporator. The solid concentrate is re-dissolved in methanol and re-precipitated with water. The resulting precipitate is filtered and dried to afford (R)-3-(2,6-dinitro-4-trifluoromethylphenoxy)pyrrolidine-1-carboxylic acid tert-butyl ester which can be used in the next step without further purification.

Step 2: The product from Step 1 is dissolved in methanol and hydrogenated at 100-200 psi and 30-50° C. in the presence of 10% Pd/C until the reduction is deemed complete by HPLC. The reaction mixture is filtered through Celite. The filtrate is concentrated and dried to afford (R)-3-(2,6-diamino-4-trifluoromethylphenoxy)-pyrrolidine-1-carboxylic acid tert-butyl ester which can be used in the next step without further purification.

Step 3: The product from Step 2 is coupled with pyrimidine-4,6-dicarboxylic acid, in the approximate ratio of 2 mol diamine:1 mol diacid, in the presence of 1-[(3-(dimethylamino)-propyl)]-3-ethylcarbodiimide hydrochloride (EDCI), in pyridine, under inert atmosphere, at ambient temperature. When the reaction is complete, the reaction mixture is diluted in water. The resulting precipitate is separated and re-dissolved in MTBE. The MTBE solution is washed with water, 0.2 N HCl, and brine, dried over anhydrous sodium sulfate, separated, and diluted in heptane. The resulting precipitate is isolated by filtration and dried to afford pyrimidine-4,6-dicarboxylic acid bis-{[3-amino-2-((R)-1-(tert-butoxycarbonyl)pyrrolidin-3-yloxy)-5-trifluoromethyl-phenyl]amide} which can be used in the next step without further purification.

Step 4: The product from Step 3 is reacted with 2.5-3 molar equivalents of ({[(tert-butoxycarbonyl)amino][(tert-butoxycarbonyl)imino]methyl}amino)pentanoic acid in pyridine, in the presence of phosphorous oxychloride, at a temperature around −5 to −10° C. The reaction is quenched with water at temperature of 15° C. The supernatant is separated from the amorphous precipitate, which is re-dissolved in MTBE, washed with water and brine, dried over anhydrous sodium sulfate, separated, and diluted in heptane. The resulting precipitate is isolated by filtration and dried to afford pyrimidine-4,6-dicarboxylic acid bis-{[3-({[(tert-butoxycarbonyl)amino][(tert-butoxycarbonyl)imino]methyl}amino)-pentanoylamino)-2-((R)-1-(tert-butoxycarbonyl)-pyrrolidin-3-yloxy)-5-trifluoromethyl-phenyl]-amide} which is used in the next step without further purification.

Step 5: The product from Step 4 is de-protected (removal of six tert-butoxycarbonyl groups) with 4M HCl/1,4-dioxane in formic acid at ambient temperature. The reaction mixture is diluted with 1,4-dioxane. The resulting precipitate is filtered, washed with 1,4-dioxane and dried to afford crude pyrimidine-4,6-dicarboxylic acid bis-{[3-(5-guanidino-pentanoylamino)-2-((R)-pyrrolidin-3-yloxy)-5-trifluoromethyl-phenyl]-amide}tetrahydrochloride (crude Compound A). The crude product is further purified by re-precipitation from methanol solution with THF (50° C. to ambient temperature) and/or re-precipitation from water/methanol solution with THF at ambient temperature.

Step 6 (chromatographic purification): The final purification of Compound A is achieved by reverse-phase chromatography (RP-HPLC) using YMC ODS-AQ phase, 50 micron, 120 Angstrom, slurry packed into a 0 dynamic axial compression column The mobile phase is a gradient of solvent B in solvent A, where solvent A is water with 0.05% trifluoroacetic acid (TFA) and solvent B is acetonitrile with 0.05% TFA. Fractions containing purified product are concentrated by rotary evaporation to afford Compound A as the trifluoroacetate salt. The final hydrochloride salt form is regenerated by passing a water/methanol solution of the trifluoroacetate salt through a Dowex 1×2-400 (Cl— form) ion-exchange column, collecting the API-containing eluate, concentrating, and drying.

Compound A bulk drug substance is stored at 2-8° C., protected from light and air, in amber HDPE containers or in double polyethylene bags in a fiber drum.

Example 3

Synthesis of Compound A

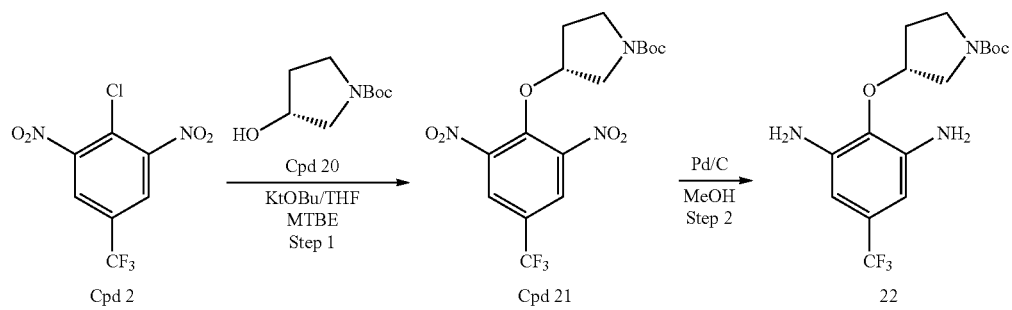

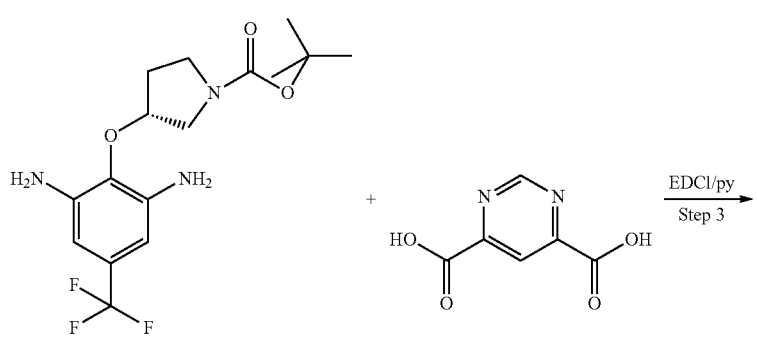

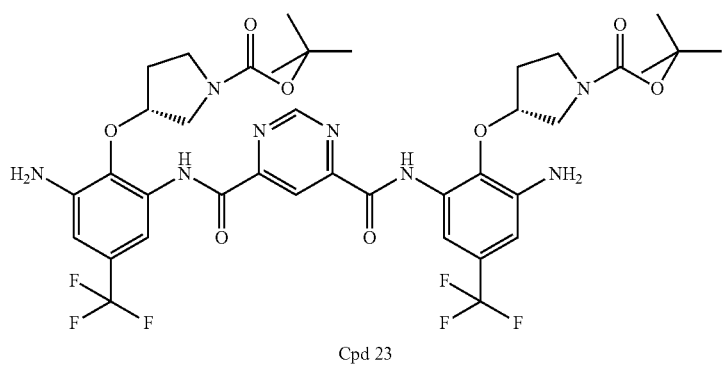

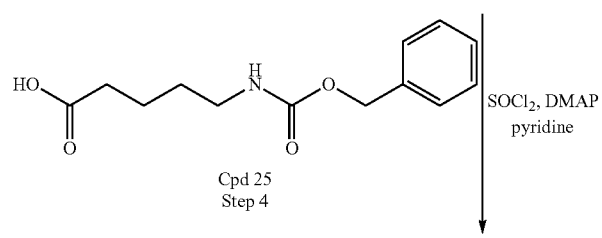

-continued
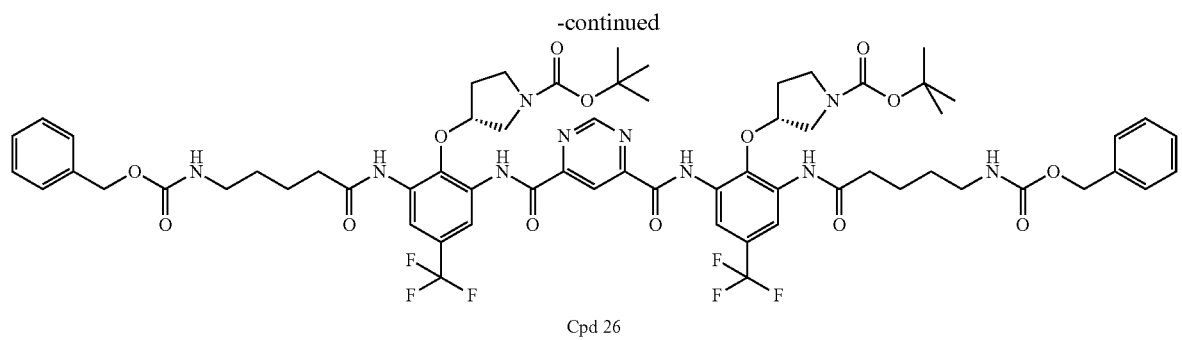
Cpd 26
Step 5 | H2, Pd/C
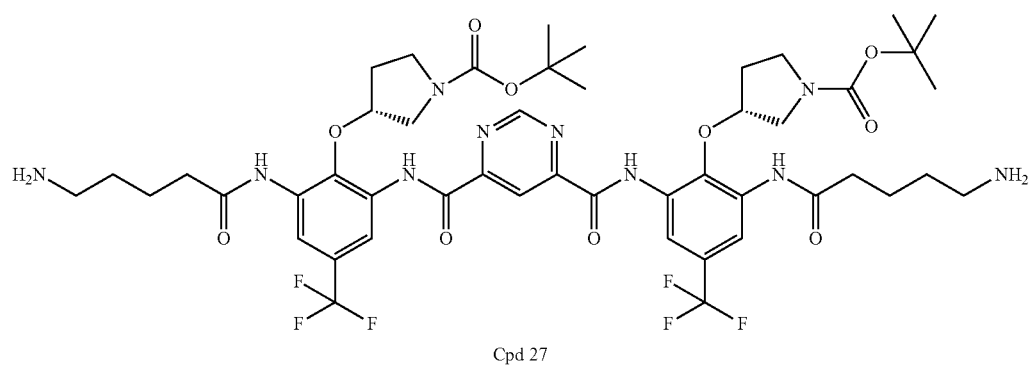
Cpd 27
Step 6
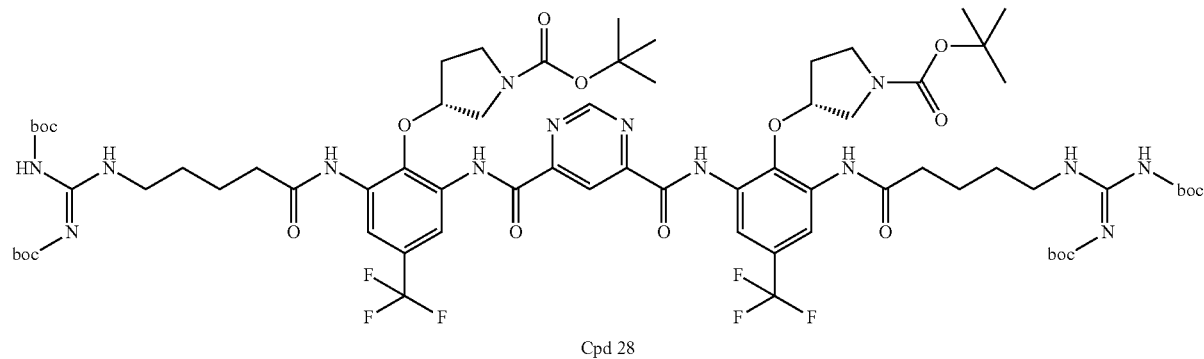
Cpd 28
Step 7 | HCl/EtOAc -continued

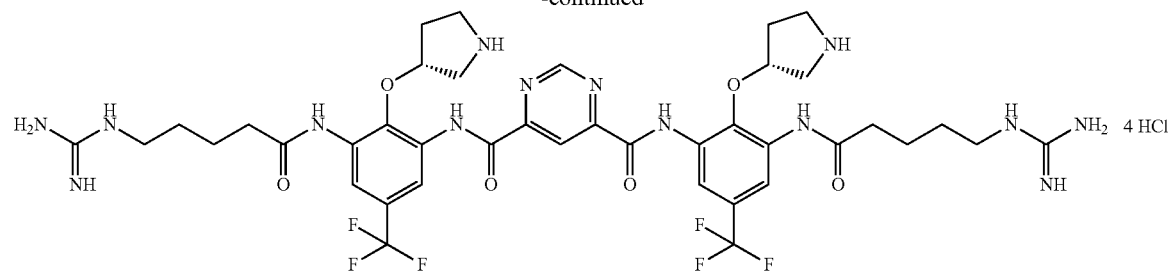
Compound A

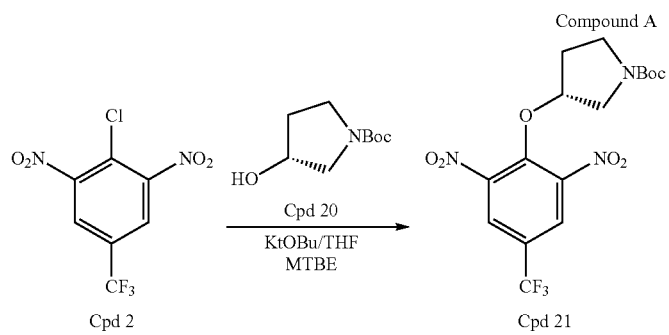

Step 1: (R)-3-Hydroxypyrrolidine-1-carboxylic acid tert-butyl ester (compound 20) is de-protonated with potassium tert-butoxide (KOtBu) in tetrahydrofuran (THF). The resulting anion is reacted 2-chloro-1,3-dinitro-5-trifluoromethyl-benzene (compound 2) in tert-butyl methyl ether (MTBE)/THF. When the reaction is complete, the reaction mixture is quenched with water and partitioned with more MTBE. The organic layer is washed with brine and water and concentrated on a rotary evaporator. The solid concentrate is re-dissolved in methanol and re-precipitated with water. The resulting precipitate is filtered and dried to afford (R)-3-(2,6-dinitro-4-trifluoromethylphenoxy)pyrrolidine-1-carboxylic acid tert-butyl ester which can be used in the next step without further purification. This reaction has been carried out at a scale using 4.2 Kg of compound 2.

Step 2: Compound 21 is dissolved in methanol and hydrogenated at 100-200 psi and 30-50° C. in the presence of 10% Pd/C until the reduction is deemed complete by HPLC. The reaction mixture is filtered through Celite. The filtrate is concentrated and dried to afford (R)-3-(2,6-diamino-4-trifluoromethylphenoxy)-pyrrolidine-1-carboxylic acid tert-butyl ester (compound 22) with HPLC purity of 92.2%. The reaction is done in four batches with a scale of 1.64 kg of compound 21 for each batch.

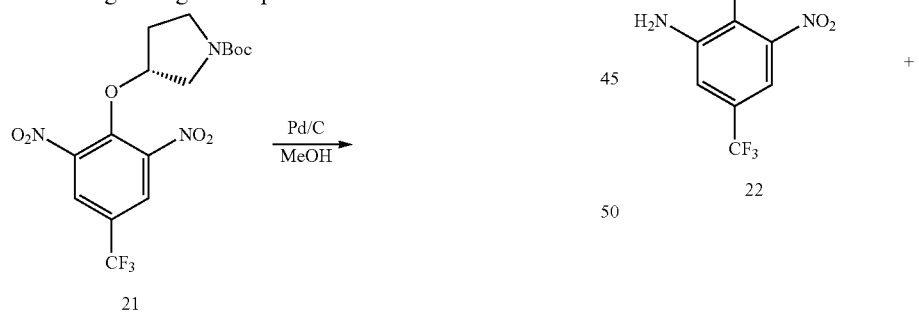

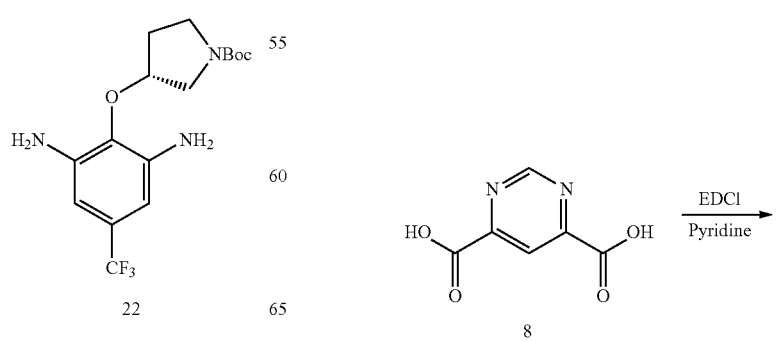

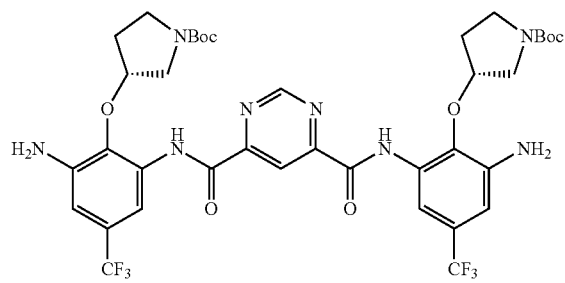

23

Step 3: Compound 22 is coupled with pyrimidine-4,6-dicarboxylic acid (compound 8), in the approximate ratio of 2 mol diamine:1 mol diacid, in the presence of 1-[(3-(dimethylamino)-propyl)]-3-ethylcarbodiimide hydrochloride (EDCI), in pyridine, under inert atmosphere, at ambient temperature. When the reaction is complete, the reaction mixture is diluted in water. The resulting precipitate is separated and re-dissolved in MTBE. The MTBE solution is washed with water, 0.2 N HCl, and brine, dried over anhydrous sodium sulfate, separated, and diluted in heptane. The resulting precipitate is isolated by filtration and dried to afford pyrimidine-4,6-dicarboxylic acid bis-{[3-amino-2-((R)-1-(tert-butoxycarbonyl)pyrrolidin-3-yloxy)-5-trifluoromethyl-phenyl]amide} (compound 23) which can be used in the next step without further purification. The reaction is carried out at a scale using 3.15 kg of compound 22.

Step 4: The solution of 3.66 g of DMAP in 60 ml anhydrous pyridine was cooled to 0° C. with ice bath. 3.60 g of thionyl chloride was added slowly. The resulting solution was stirred for 10 minutes. The starting material N-Cbz acid (7.53 g, 30 mmol), Cpd 23 (8.54 g, 10 mmol), were added to the solution respectively. The resulting mixture was stirred at RT for 4 hours. Water (500 mL) was added. After the mixture was stirred vigorously at room temperature for 2 hours, the solid was filtered and washed with 250 mL of water. The solid was dissolved in ethyl acetate (300 mL). The organic layer was washed with 10% citric acid solution (100 mL) and brine (100 mL) and dried over $Na_2SO_4$. After evaporation, the residue was dissolved in 40 mL DCM, then 250 mL hexane was added. The precipitate was collected and dry under vacuum. 13.20 g of product was obtained in 95% purity. Yield: 100%.

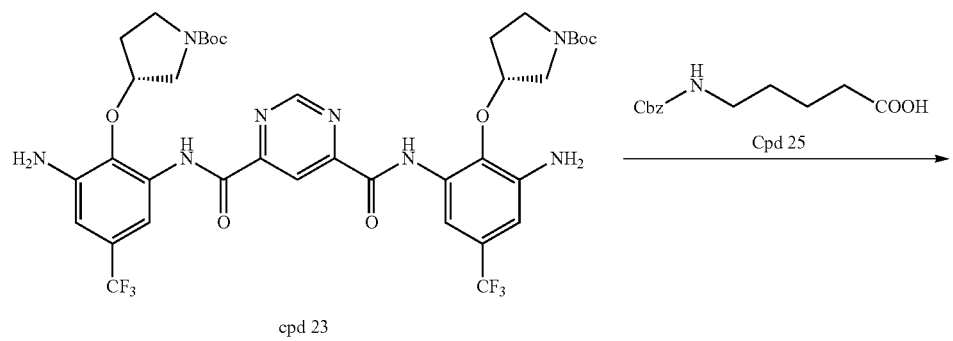

cpd 23

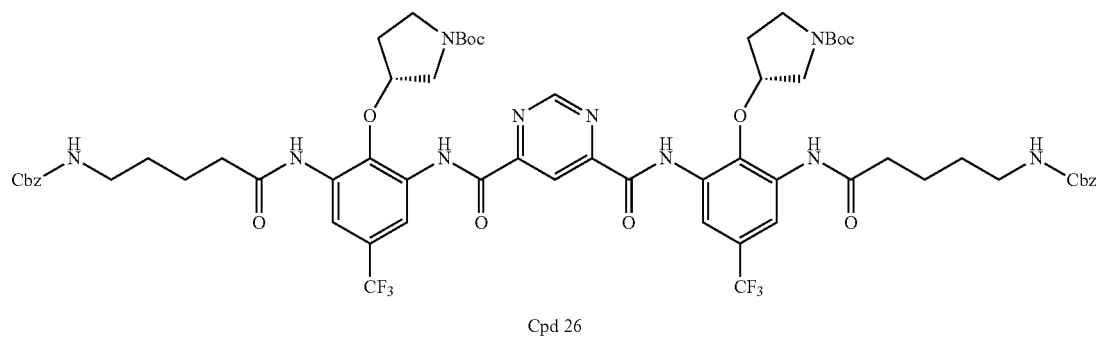

Cpd 26

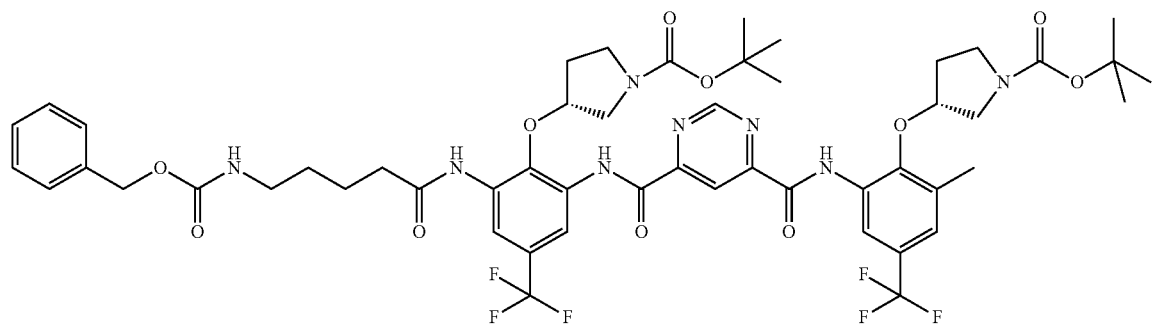

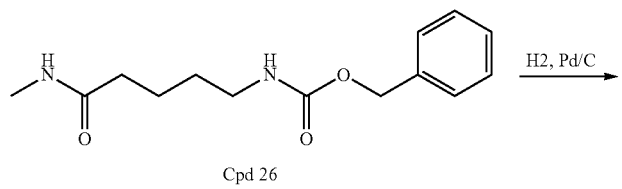

Cpd 26

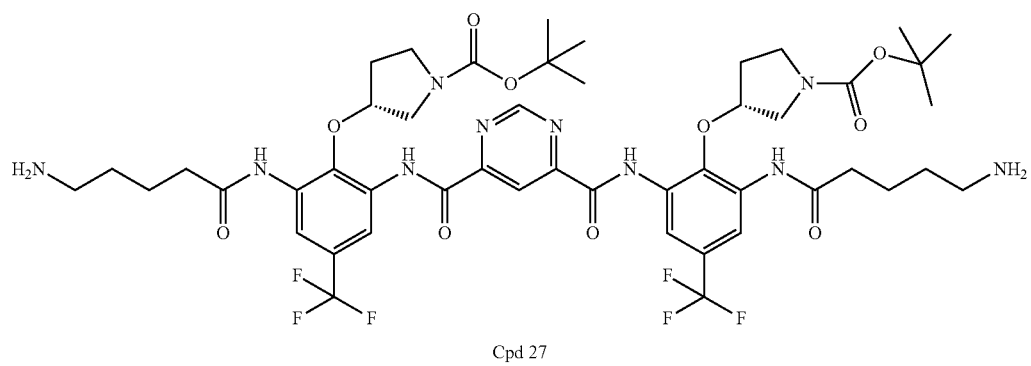

Cpd 27

Step 5: Compound 26 (13.20 g) was dissolved in MeOH with 2 equiv. of 1 N HCl, and the catalyst Pd/C (10%) 1.0 g was added. The reaction mixture was put on a Parr hydrogenator and shaken for 2 hours under 60 psi of hydrogen. LCMASS showed no progress and another 1.0 g of catalyst was added. The reaction mixture was put on a Parr hydrogenator and shaken for 3 hours under 60 psi of hydrogen. The mixture was filtered through celite to remove the catalyst. The filtrate was concentrated to dryness on a rotovap at 30° C. 11.50 g of product was obtained in 95% purity. Yield: 100%.

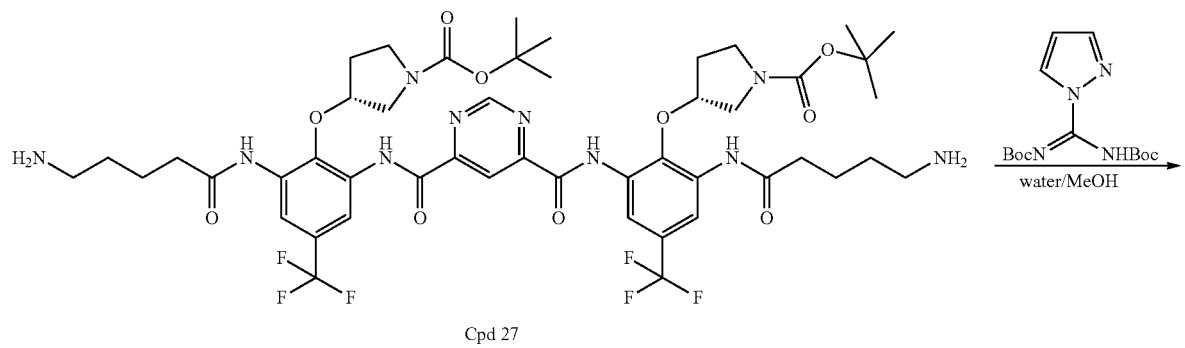

Cpd 27

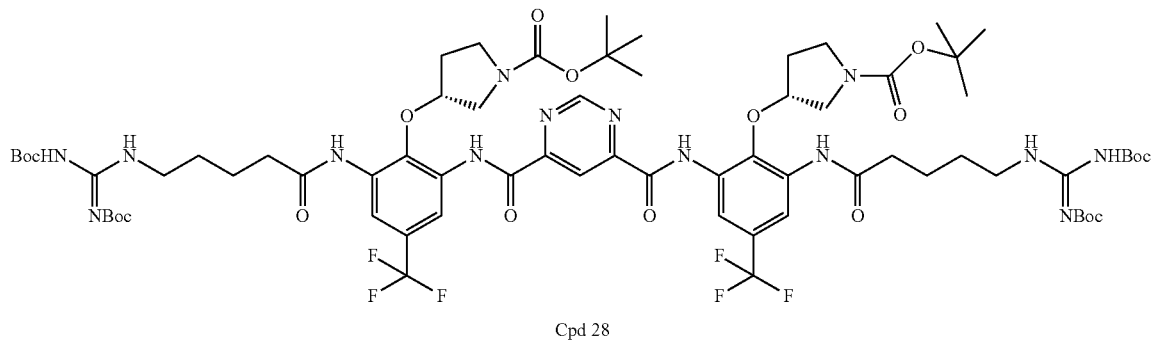

Cpd 28

Step 6: Compound 27 (11.50 g, 10 mmol) was dissolved in 60 ml methanol and DCM (1:1). Then, 4.04 g triethylamine (40 mmol) was added. di-Boc pyrazole 9.3 gram (30 mmol) was added and the resulting mixture was stirred at room temperature for 1 hour. After removing 95% of the solvent, 300 mL water was added and the mixture was stirred vigorously for 2 hours. The solid was filtered and washed with 300 mL water. The solid was dissolved in 300 mL ethyl acetate and dried over $Na_2SO_4$. After evaporating the solvent, the solid was dissolved in 40 mL DCM, then 500 mL hexane was used to precipitate the product out. The solid was collected and dried under vacuum. 13.0 gram of product was obtained in 85% yield (90% purity).

vacuum, and dried. Recovery was 50-60%. Compound 28 with 95% purity (0.3 g) was dissolved and stirred in ethyl acetate (3 mL) at room temperature (22° C.) under argon. HCl gas was bubbling into the solution for 20 minutes. The color of the solution was turning deep yellow as the bubbling was ongoing. The solid started crushing out in 15 minutes. The solution was stirred at room temperature for another 1 hour. Additional 4 mL of ethyl acetate was introduced into the reaction mixture because of a loss of ethyl acetate. The mixture was bubbling with HCl gas for 10 minutes. The mixture was stirred for 2.5 hours. One third of the mixture was filtered and washed with ethyl acetate. Two thirds of the mixture was stirred at room temperature overnight. Then, 30 mL of ethyl

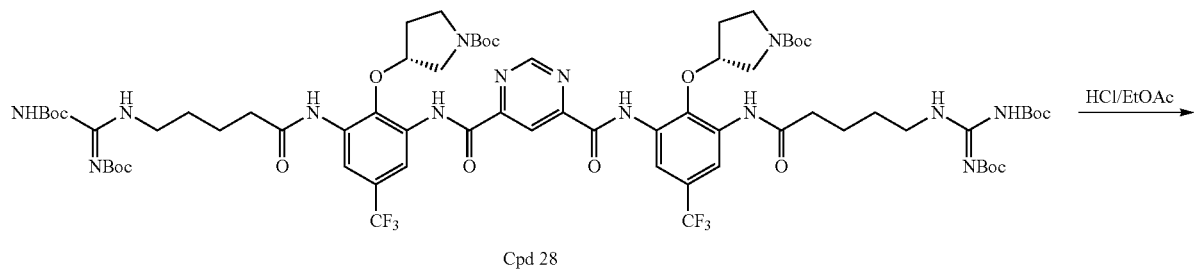

Cpd 28

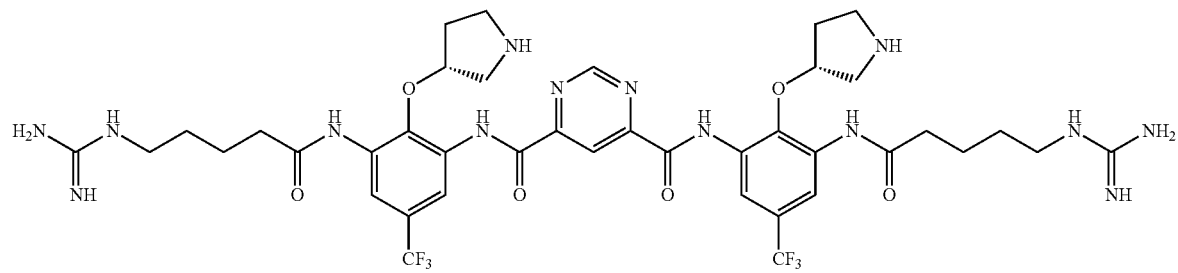

PMX30063·4HCl

Step 7: Compound 28 (1.5 g) was purified on 80 g silica gel column by using a gradient of 10-88% EtOAc in DCM. Fractions with purity above 95% were collected, evaporated under acetate was added to the mixture. After filtration, the cake was washed with ethyl acetate twice (2×140 mL) and dried. The solid was immersed in ethyl acetate (8 mL) and kept in a freezer. The reaction process was performed in 4 hours. Overnight stirring did not show much change. The purity of the final product was 98% with one major impurity of 1.2%.
Example 4
Synthesis of Compound A
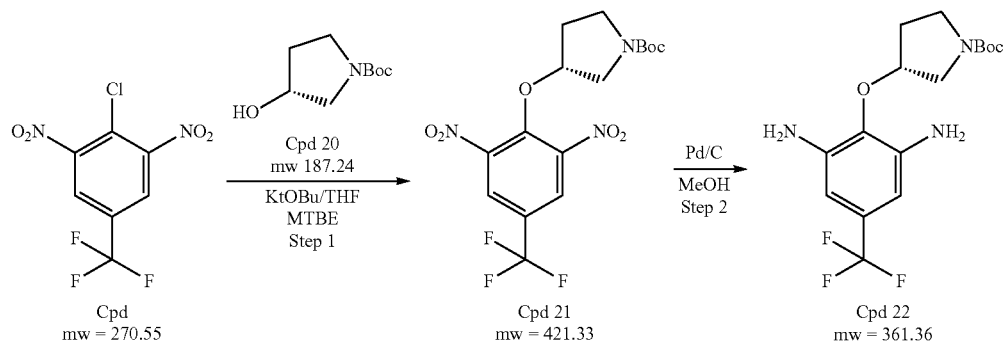
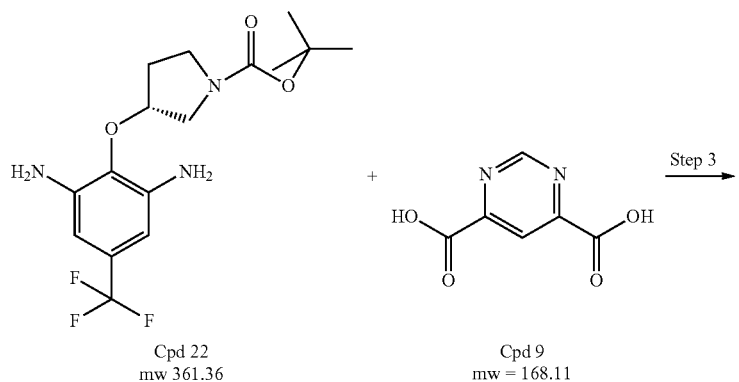
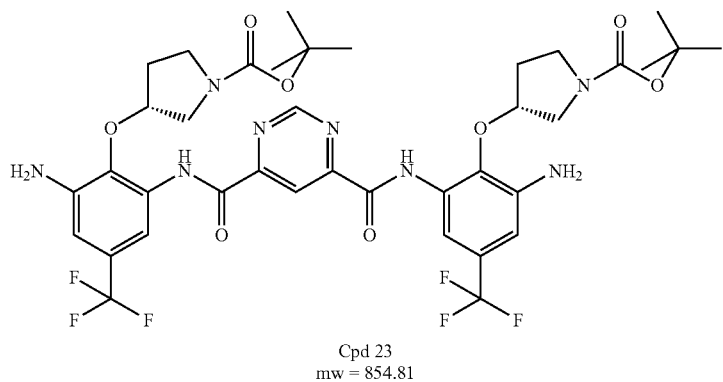
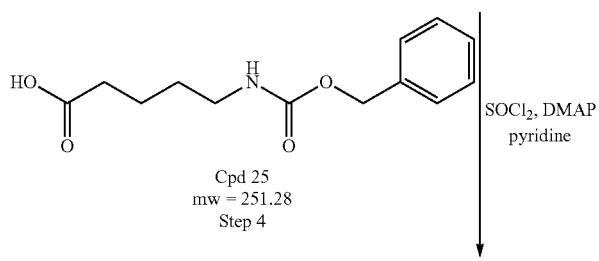

-continued
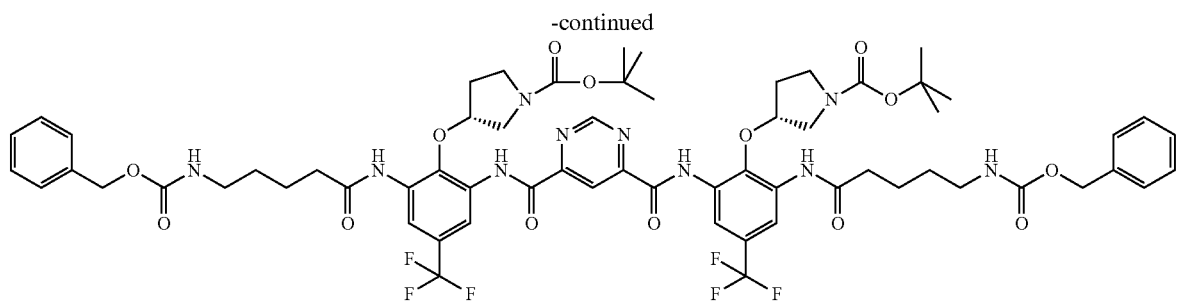
Cpd 26
mw = 1308.3
Step 5 | H2, Pd/C, MeOH
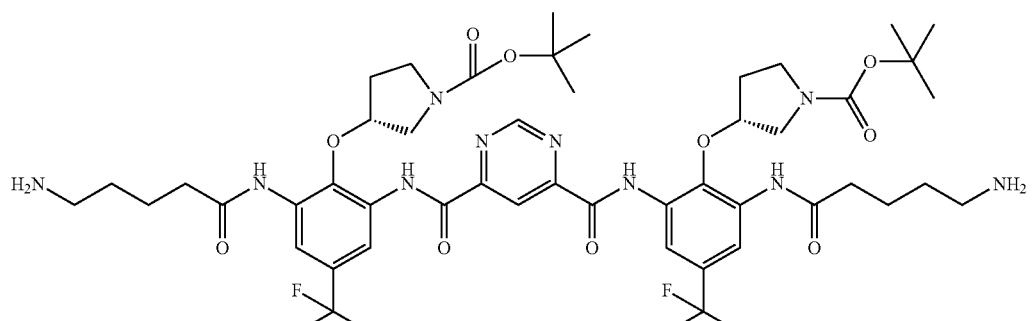
Cpd 27
mw = 1069.12
Step 6 | 
[pyrazole carboxamidine reagent with boc groups], MeOH, HCl, Et₃N
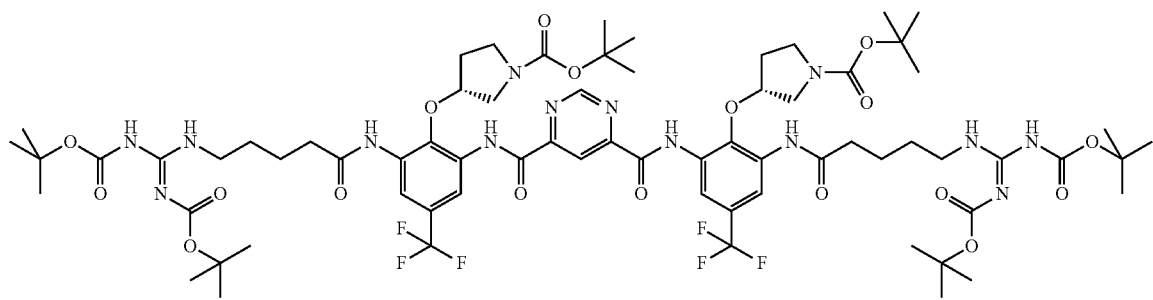
Cpd 28
mw = 1537.63
Step 7 | HCl/EtOAc, 20 equiv. H₂O

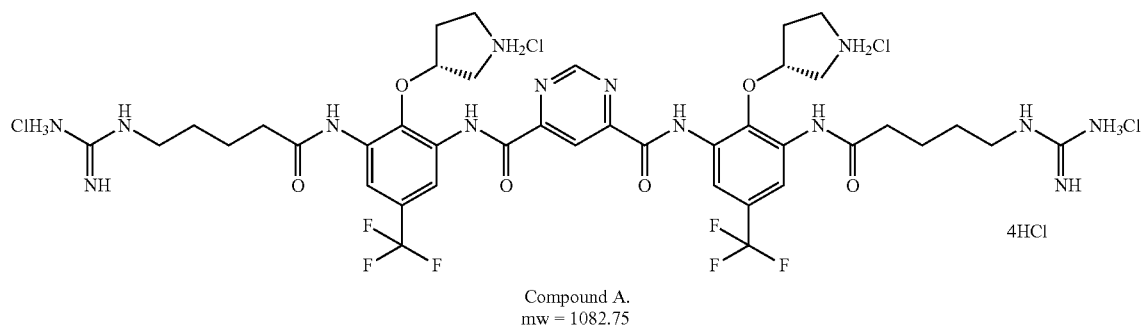

Compound A.
mw = 1082.75

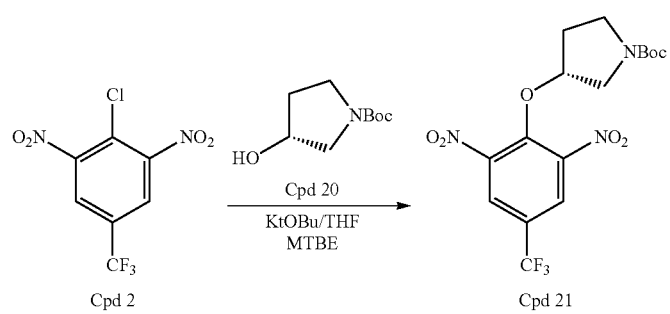

Step 1: To a nitrogen purged 4-necked 12 L RBF was added 305.32 g of compound 2, 700 mL of MTBE with stirring and the mixture was cooled in an ice/water bath. Compound 20 (212.43 g) was dissolved with the potassium tert-butoxide (1.31 L of 1 M solution in THF) providing a slightly turbid mixture. This mixture was added to compound 21 solution in the RBF over 86 minutes with stirring while maintaining <9.0° C. internal temperature. The reaction was removed from the cold bath 30 minutes later and allowed to stir at ambient temperature for 15.5 hours. Upon stirring, several small ice chips were added with a temperature decrease from 21.4° C. to 18.4° C. Then water was added (1.5 L) and MTBE (1.5 L) and the mixture was stirred for 10 minutes. The mixture was phase-split and separated in a 6 L separatory funnel. The aqueous layer was re-extracted with MTBE (500 mL). The organic layers were combined and washed with 2:1 water/saturated brine (3×900 mL), and concentrated to a reddish/rust colored solid under reduced pressure. This solid was dissolved in 2.45 L of MeOH and the solution was transferred to a 4 L Erlenmeyer flask. Then water (1 L) was added with stirring, in portions, resulting in thick slurry. The mixture was covered and placed in a refrigerator (1-5° C.) for 16 hours. The solid was collected by filtration and dried under vacuum. The dried product was a bright yellow powder. Yield: 395.3 g, HPLC purity 94.0%.

The potassium tert-butoxide can be replaced with, for example, any alkoxide, sodium hydride, potassium hydride, or any base that can deprotonate the hydroxyl of compound 20. Compound 2 can be substituted at the 2 position by any halide.

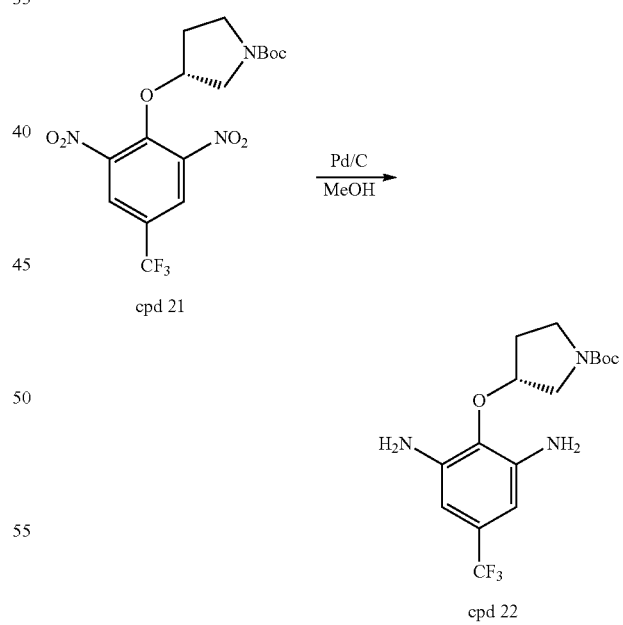

Step 2: To a stainless steel 2 gal Parr stirrer unit was added the catalyst Pd/C (10 wt %, 20 g), compound 21 from Step 1 (394.37 g) and then 2 L of MeOH carefully with swirling. The vessel was charged with hydrogen and vented twice. The mixture was then stirred starting at 82 psi hydrogen; the pressure dropped to 0 psi. The vessel was repeatedly filled to 62 psi, 28 psi and 36 psi, respectively, each time allowing the pressure to go back to 0 psi (total uptake of 208 psi in 51 minutes). The internal temperature started at 16° C. and the mixture showed a gradual but rapid exotherm to maximum of 38° C. The internal temperature was maintained at 33-38° C. The vessel was pressurized to 49 psi with uptake of 23 psi. The vessel was pressurized to 90 psi with uptake of 12 psi over 1 hour. The vessel was pressurized to 120 psi with uptake of 82 psi over 6 hours. The vessel was then re-pressurized to 51 psi with uptake of 37 psi over 14.33 hours (the total uptake of hydrogen was 362 psi). The reactor was dismantled and the mixture was filtered through a pad of celite 545 pre-moistened with MeOH (11.0 cm diameter Büchner funnel). The reactor and pad were rinsed with MeOH and the pad was suctioned until slow dripping and colorless filtrate (~3.0 L total volume). The filtrate was further filtered through a fluted paper disk to remove some fine dark powders. The clear filtrate was transferred to a 5 L RBF and concentrated to orange/brown colored viscous oil which was chilled to 3-4° C. overnight, during which time the material partially solidified/crystallized. The material was warmed and further suctioned under reduced pressure to form a solid rust/brown gummy/waxy hard solid chunk. To the RBF were added heptanes (2×700 mL) and MTBE (700 mL). The mixture was stirred with overhead mechanical stirring for 3.5 hours. The liquid layer was decanted from the solid, the chunk was broken into smaller pieces, the liquid was placed back into the RBF and the suspension was stirred vigorously for 16.75 hours. Then the small pieces left were further crushed using the end of a glass stir shaft and the mixture was vigorously stirred for 70 minutes. The suspension was filtered through a tared fritted glass funnel using the filtrate to complete the transfer. The funnel was covered and vacuum dried with low heat (41° C.) for 4 hours providing the product as a faint peachy/beige powder. Yield 270.60 g, HPLC purity 98.5%.

The Pd/C catalyst can be replaced by, for example, any catalyst suitable for the hydrogenation of a nitro group.

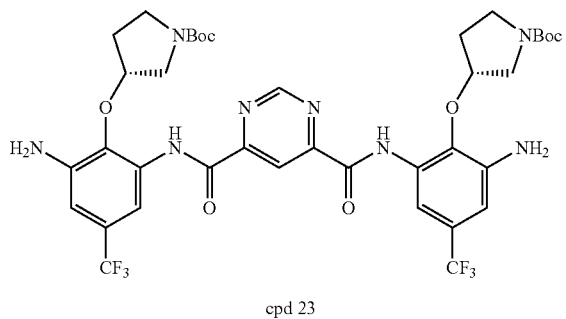

cpd 23

Step 3 (Option 1): 2-Chloro-4,6-dimethoxy-1,3,5-triazine (4.0 g) was stirred in anhydrous THF (60 mL). N-Methylmorpholine (4.4 g) was added. The resulting mixture was stirred at room temperature for 30 minutes. Then compound 22 (7.2 g) and pyrimidine-4,6-dicarboxylic acid (1.68 g) were added. The mixture was stirred at room temperature for 24 hours. Then the solvent was evaporated completely in vacuum. Water (250 mL) was added and the mixture was stirred for 4 hours. After filtration, the yellow cake was washed with water (3×100 mL) and stirred in water (250 mL) for 4 hours again. The filtration and washing procedure was repeated twice. Then the solid was dry in the air. The solid was dissolved in 15 mL of DCM:Hexane:Acetone (5:5:1) solution. The mixture was kept at room temperature for 2 days. The solid was filtered and washed with 10 mL of DCM:Hexane (1:1) solution twice. The recrystalization procedure was repeated one more time to give light yellow solid. Yield 70%, HPLC purity 100%.

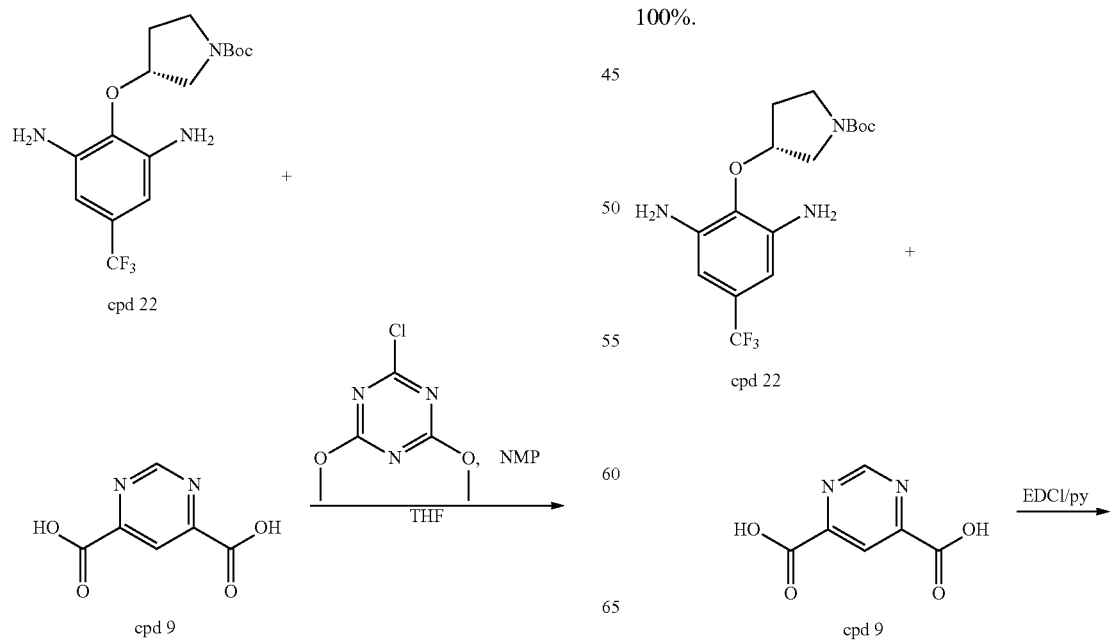

-continued

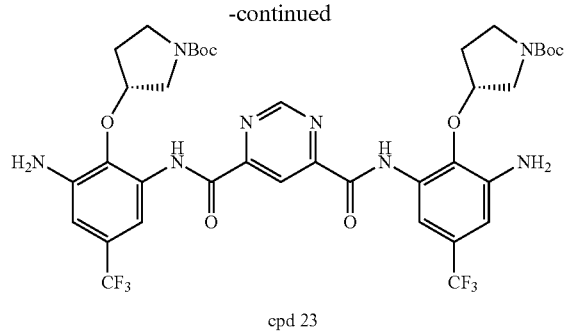

cpd 23

Step 3 (Option 2): EDCI (6.0 g) was stirred in anhydrous Pyridine (60 mL). Then compound 22 (7.2 g) and compound 9 (0.56 g) were added. The mixture was stirred at room temperature for 2 hours. Then another portion pyrimidine-4,6-dicarboxylic acid (0.56 g) was added. After the mixture was stirred at room temperature for another 2 hours, the third portion pyrimidine-4,6-dicarboxylic acid (0.56 g) was added. The resulting mixture was stirred at room temperature for 24 hours. Then the solvent was evaporated completely in vacuum. Water (250 mL) was added and the mixture was stirred for 4 hours. After filtration, the yellow cake was washed with water (3×100 mL) and stirred in water (250 mL) for 4 hours again. The filtration and washing procedure was repeated twice. Then the solid was dry in the air. The solid was dissolved in 15 mL DCM:Hexane:Acetone (5:5:1) solution. The mixture was kept at room temperature for 2 days. The solid was filtered and washed with 10 mL DCM:Hexane (1:1) solution twice. The recrystalization procedure was repeated one more time to give light yellow solid. Yield 70%, HPLC purity 100%.

EDCI can be replaced with, for example, any amide coupling reagents that generate acid anhydride or activated ester such as CDI, DCC, HOBt, HOAt, POCl$_3$.

Step 4: The solution of DMAP (3.66 g) in 60 mL anhydrous pyridine was cooled to 0° C. with ice bath. Thionyl chloride (3.60 g) was added slowly. Then the resulting solution was stirred for 10 minutes. The starting material N-Cbz acid (7.53 g, 30 mmol), Cpd 5 (8.54 g, 10 mmol), were added to the solution respectively. The resulting mixture was stirred at room temperature for 4 hours. Then water (500 mL) was added. After the mixture was stirred vigorously at room temperature for 2 hours, the solid was filtered and washed with 250 mL water. The solid was dissolved in ethyl acetate (300 mL). The organic layer was washed with 10% citric acid solution (100 mL) and brine (100 mL) and dried over Na$_2$SO$_4$. After evaporation, the residue was dissolved in 40 mL DCM, then 250 mL hexane was added. The precipitate was collected and dry under vacuum. 13.20 g product was obtained in 95% purity. Yield: 100%.

The thionyl chloride can be replaced with, for example, POCl$_3$, (EtO)$_2$POCl, or oxalyl chloride.

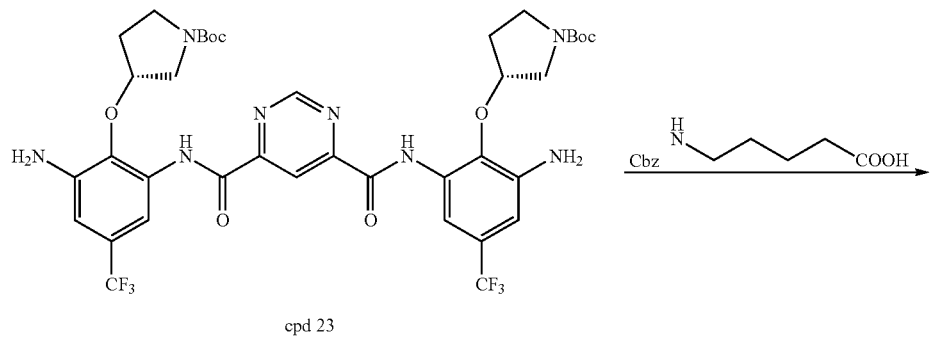

cpd 23

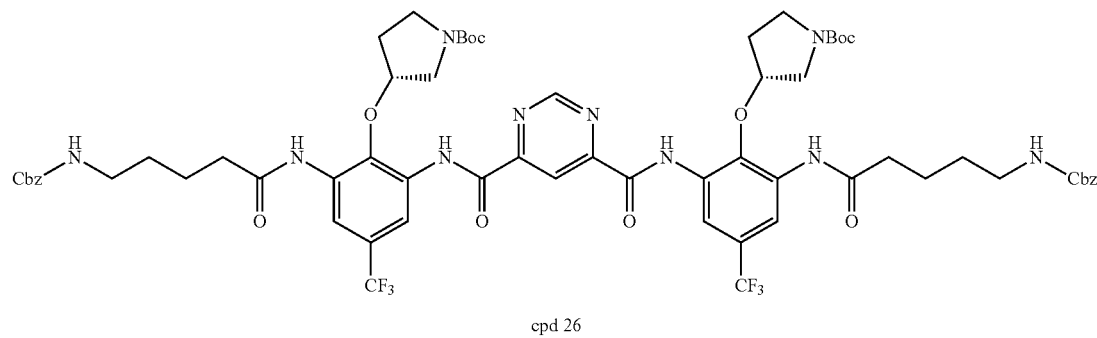

cpd 26

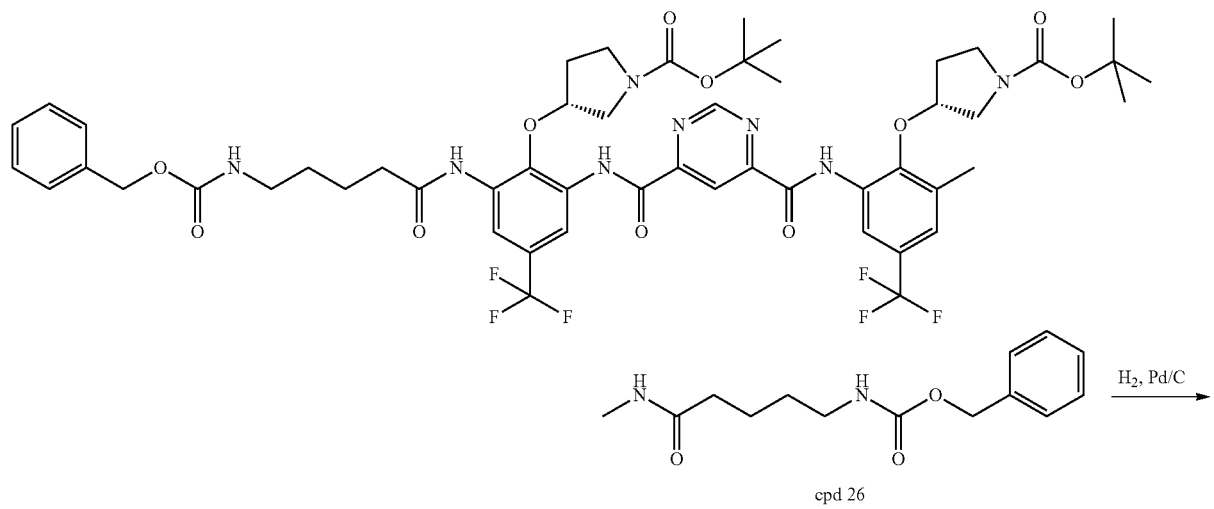

cpd 26

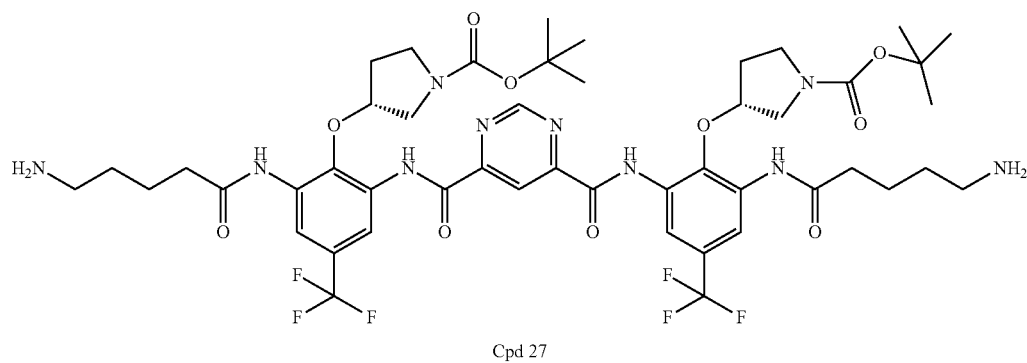

Cpd 27

Step 5: Compound 26 (13.20 g) was dissolved in MeOH with 2 equiv. of 1 N HCl, and the catalyst Pd/C (10%) 1.0 gram was added. The reaction mixture was put on a Parr hydrogenator and shaking for 2 hours under 60 psi of hydrogen. LCMASS showed no progress and another 1.0 gram catalyst was added. The reaction mixture was put on a Parr hydrogenator and shaking for 3 hours under 60 psi of hydrogen. The mixture was filtered through celite to remove the catalyst. The filtrate was concentrated to dryness on a rotovap at 30° C. 11.50 g product was obtained in 95% purity. Yield: 100%.

The Pd/C catalyst can be replaced with, for example, any catalyst suitable for the hydrogenlysis of CBZ group.

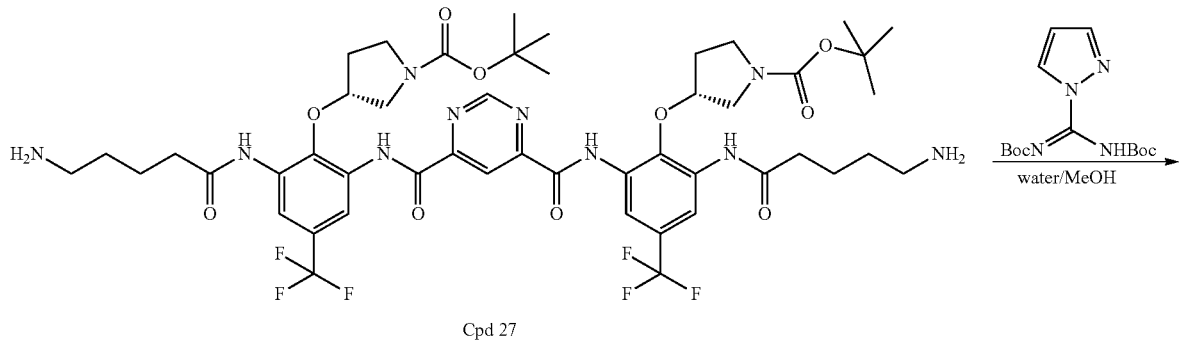

Cpd 27

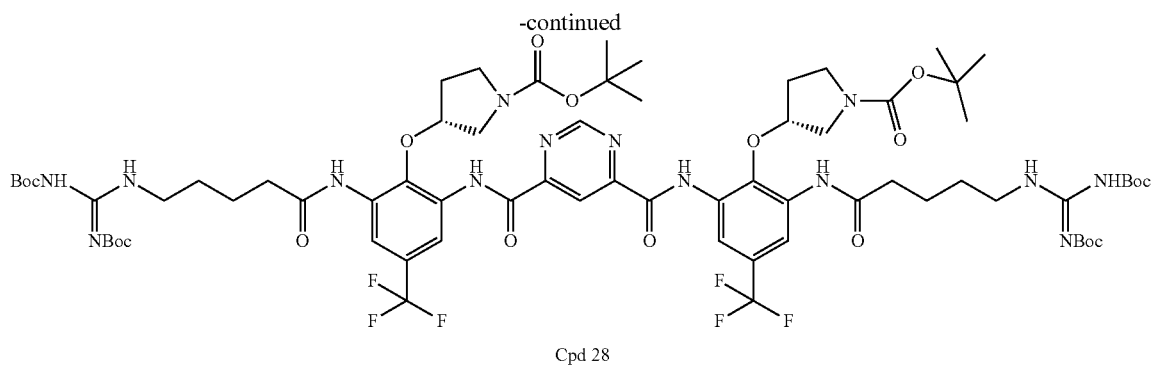

Cpd 28

Step 6: Compound 27 (11.50 g, 10 mmol) was dissolved in 60 mL methanol and DCM (1:1). Then 4.04 g triethylamine (40 mmol) was added. di-Boc pyrazole 9.3 gram (30 mmol) was added and the resulting mixture was stirred at room temperature for 1 hour. After removing 95% of the solvent, 300 mL water was added and the mixture was stirred vigorously for 2 hours. The solid was filtered and washed with 300 mL water. The solid was dissolved in 300 mL ethyl acetate and dried over $Na_2SO_4$. After evaporating the solvent, the solid was dissolved in 40 mL DCM, then 500 mL hexane was used to precipitate the product out. The solid was collected and dried under vacuum. 13.0 g product was obtained in 85% yield (95% purity).

The di-Boc pyrazole can be replaced with, for example, isourea or di-Boc isourea.

filtration under nitrogen. The solid was rinsed with EtOAc, triturated with MeOH/THF (1:1) and dried under vacuum. Yield 84%.

The HCl/EtoAC can be replaced with, for example, HCl/dioxane.

Example 5

Antimicrobial Activity vs. Gram-Positive Clinical Isolates (Table 1A) and Gram-Negative Clinical Isolates (Table 1B)

Compound A was evaluated in vitro in accordance with defined CLSI documents specific to the organisms (aerobic,

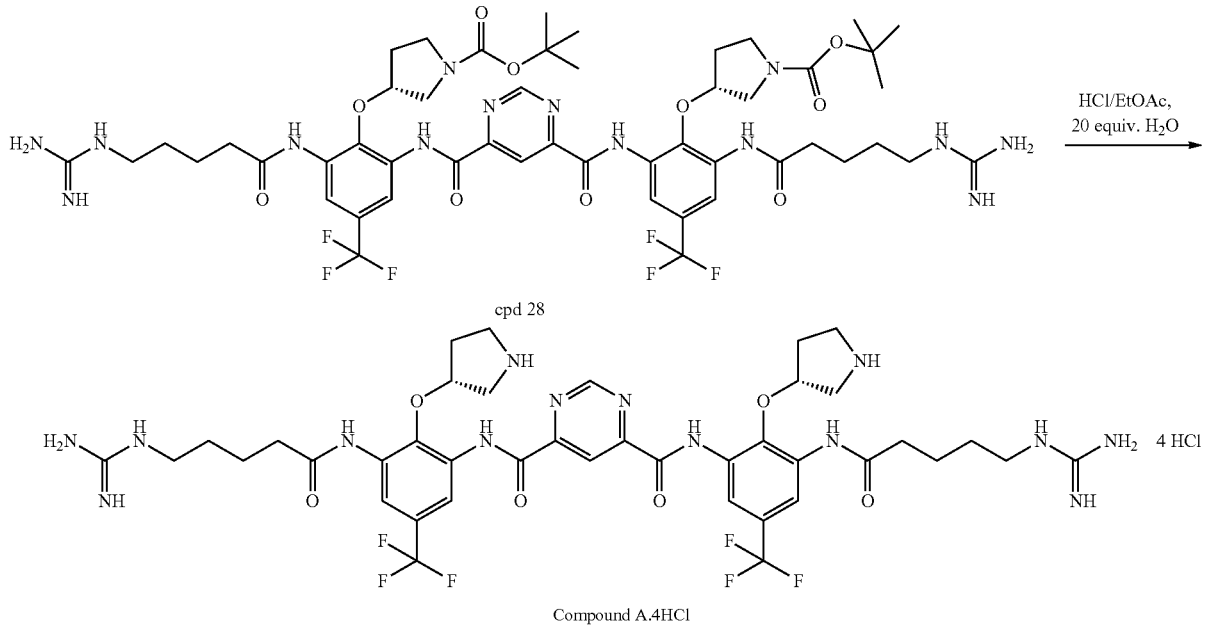

Step 7: Compound 28 (1.17 kg, 0.76 mol) was dissolved in 24 L of EtOAc, followed by addition of 281 mL of water. HCl gas was added to the solution while the temperature of reaction was controlled below 45° C. by adjust addition speed. The total reaction time is 5 hours among which 1.5 hour is the time of HCl addition. HPLC indicated the starting material is less than 1% and the precipitated product was collected by anaerobic or yeast) tested in this study. Ampicillin, ceftazidime, cefuroxime, ciprofloxacin, linezolid, and vancomycin were tested alongside as comparator agents for aerobic bacteria; clindamycin and metronidazole were tested as comparators for anaerobes; fluconazole was tested as a comparator for yeast isolates. Stock solutions of Compound A were prepared in dimethyl sulfoxide (DMSO). Ampicillin, ceftazidime, cefuroxime, ciprofloxacin, linezolid, vancomycin, metronidazole, clindamycin, and fluconazole were prepared each according to its manufacturer's guideline.

Aerobes (M7-A7)1

Minimum inhibitory concentrations (MICs) in µg/ml were determined according to CLSI guideline M7-A7 by broth microdilution. All aerobes were tested using Mueller-Hinton broth medium with the exception of *Streptococcus* spp., which were tested using cation-adjusted Mueller-Hinton broth supplemented with 2-5% lysed horse blood. Results are shown in Table 1A and Table 1B.

TABLE 1A

| Organism Gram-Positive | MIC (µg/mL)* 2-3 isolates/organism | | | |
|---|---|---|---|---|
| | Compound A | Linezolid | Vancomycin | Ceftazidime |
| *Entero. faecalis* | 1 | 1-2 | 1 | >64 |
| *Entero. faecium* (VRE) | 1 | 1-2 | >128 | >64 |
| *Staph. aureus* (MRSA) | 0.5-1 | 1-2 | 0.5-1 | 32 |
| *Staph. spidermidis* | 0.25-0.5 | 0.5-1 | 2 | 16-32 |
| *Staph. saprophyticus* | 0.25-0.5 | 1-2 | 1-2 | 32->64 |
| *Staph.* spp. (coagulase -) | 0.25-0.5 | 1 | 1-2 | 16-32 |
| *Strept. agalactiae* | 2 | 1 | 0.5 | 0.5 |
| *Strept. pneumoniae* | 4-8 | 1 | 0.5 | 0.25 |
| *Strept. pyogenes* | 1-4 | 1 | 0.5 | 0.12 |
| *Strept. viridians* | 2-8 | 1 | 0.5-1 | 0.5-4 |

*Broth microdilution assays performed according to standard CLSI guidelines.

TABLE 1B

| Organism Gram-Negative | MIC (µg/mL)* 2-3 isolates/organism | | | |
|---|---|---|---|---|
| | Compound A | Ceftazidime | Linezolid | Vancomycin |
| *Citrobacter freundi* | 2-4 | 0.25-2 | >16 | >128 |
| *Citrobacter koseri* | 1-2 | 0.12-0.25 | >16 | >128 |
| *Enterobacter cloacae* | 0.5-4 | 0.25 | >16 | >128 |
| *Escherichia coli* | 1-2 | 0.06 | >16 | >128 |
| *Klebsiella oxytoca* | 2-8 | 0.06-0.12 | >16 | >128 |
| *Klebsiella pneumoniae* | 1-2 | 0.06-0.12 | >16 | >128 |
| *Morganella morganii* | 2->64 | 2-16 | >16 | >128 |
| *Proteus mirabilis* | 64->64 | 0.03-0.06 | >16 | >128 |
| *Proteus vulgarisi* | 64->64 | 0.12 | >16 | >128 |
| *Providencia stuartii* | 16-64 | 0.12-0.64 | >16 | >128 |
| *Acinetobacter* spp. | 4 | 2-64 | >16 | 128->128 |
| *Pseudomonas aeruginosa* | 32 | 1-8 | >16 | >128 |
| *Serratia marcescens* | 32 | 0.12-0.25 | >16 | >128 |
| *Stenotrophomonas maltophilia* | 8->64 | 4-8 | >16 | 32-128 |
| *Haemophilus influenzae* | 4-8 | 0.06-0.12 | 16->16 | 128 |

*Broth microdilution assays performed according to standard CLSI guidelines.

Compound A exhibited broad coverage against the Gram-positive pathogens with *S. aureus* and coagulase-negative *Staphyloccal* species showing the lowest MICs. Compound A was active against the Gram-negative pathogens but overall coverage was less than for the Gram-positive organisms.

Example 6

MICs with *Staphylococcus* Species with Defined Resistance Phenotypes

Evaluation of the susceptibility profiles of Compound A against selected isolates was carried out in vitro by broth microdilution methodology using Mueller-Hinton broth medium according to CLSI document M7-A7. CLSI interpretive breakpoints were applied where applicable as directed by CLSI document M100-S17. Results are shown in Table 2.

TABLE 2

| | Drug-suscept. | OXA-R | VRSA/VISA OXA-R | LZD-NS OXA-R | DAP-NS OXA-R | VRSA/VISA DAP-NS OXA-R |
|---|---|---|---|---|---|---|
| isolates | 59 | 69 | 7 | 5 | 5 | 3 |
| Compound A MIC range | 0.25-1 | 0.25-2 | 0.5-1 | 0.5-1 | 0.5-2 | 0.5-1 |

*Broth microdilution assays performed according to standard CLSI guidelines.
OXA-R: oxacillin-resistant;
VRSA: vancomycin-resistant *S. aureus*;
VISA: vancomycin intermediate *S. aureus*;
LZD-NS: linezolid non-suscepetible;
DAP-NS: daptomycin non-susceptible.

Compound A was active in vitro against all isolates of *S. aureus* and coagulase-negative staphylococci, including isolates of *S. aureus* with characterized resistance to daptomycin, linezolid, and vancomycin (last-line therapeutics for the treatment of resistant *S. aureus* such as MRSA). Against *S. aureus* isolates, there was no alteration in activity against resistant isolates relative to susceptible isolates. Against coagulase-negative staphylococci, activity was not affected by resistance to methicillin.

Example 7

Cytotoxicity and Selectivity

Cytotoxicity of Compound A was evaluated in a colorimetric assay using a transformed human liver cell line (HepG2, HB-8065) and an embryonic mouse cell line (NIH/3T3 cells, CRL-1658). This assay measures the bioreduction of a novel tetrazolium compound to a soluble formazan product by viable cells. HepG2 cells were seeded in 96 well plates at $2\times10^4$ cells/well in MEM medium with 10% fetal bovine serum (FBS) 24 hours prior to use. NIH/3T3 cells were seeded in 96 well plates at $2\times10^4$ cells/well in DMEM medium with 10% bovine calf serum (BCS) 24 hours prior to use. Cell monolayers were rinsed in serum-free media and incubated for one hour with Compound A in serum-free media. After incubation, the media was replaced with serum supplemented media and live cells were measured using the Cell Titer 96 Aqueous Non-Proliferation Assay kit (Promega, Madison, Wis.). $EC_{50}$ values were determined using a four parameter logistic equation: $Y=Bottom+(Top-Bottom)/(1+10^{((LogEC_{50}-X)*HillSlope)})$.

Cytotoxicity of Compound A was also evaluated in a hemolysis assay using human erythrocytes. Pooled whole human blood was centrifuged to separate the red blood cells (RBC). The isolated RBCs were rinsed and diluted in Tris-buffered saline (TBS buffer, pH 7.4) to obtain a 0.22% RBC stock suspension. 5 µL of Compound A stock solution was added to 45 µL of RBC suspension and incubated with shaking for 1 hour at 37° C. At the conclusion of the incubation time, samples were centrifuged and 30 µL of the supernatant was added to 100 µL of water. $OD_{414}$ measurements were read for hemoglobin concentration. The bee venom peptide melittin was used as a positive control. EC50 values were determined as described above. Results are shown in Table 3.

TABLE 3

| Compound | MIC or MIC$_{90}$* (µg/mL) S. aureus | Cytotoxicity (EC$_{50}$ µg/mL) RBCs | 3T3 | HepG2 | Selectivity (EC$_{50}$/MIC) RBCs | 3T3 | HepG2 |
|---|---|---|---|---|---|---|---|
| Compound A | 1.0* | >500 | 430 | 1,031 | >500 | 430 | 1,031 |
| melittin | 2 | 2 | 4 | 1 | 1 | 2 | 0.5 |

Compound A demonstrates great overall selectivity.

Example 8

Time-Kill vs *S. Aureus* (ATCC 27660)

Figure 1A:
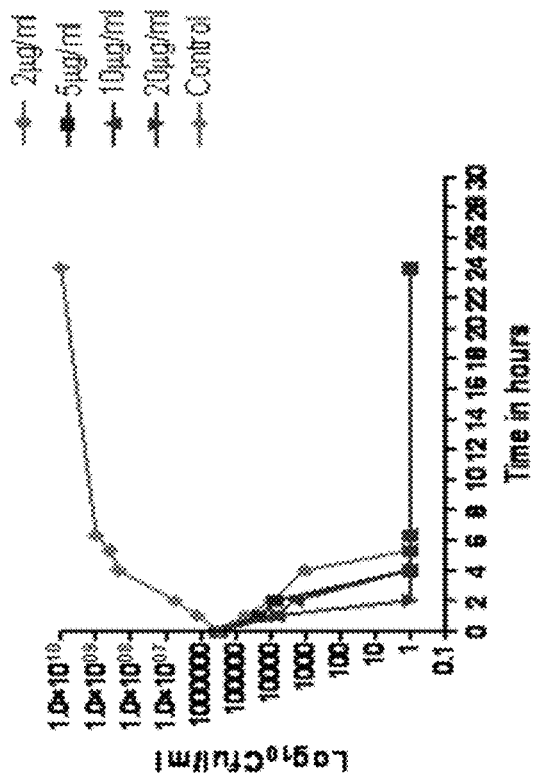

Time-kill studies of Compound A versus *E. coli* ATCC25922, *E. coli* (lab strain) D31, and *S. aureus* ATCC27660 were determined in a standard protocol by measuring the time it takes to reduce the initial inoculums 3 log units. Three ml of cation-adjusted Mueller-Hinton medium was inoculated with 20 µL of frozen bacterial stock and incubated at 37° C. on a shaker platform (250 rpm) overnight. The suspension was diluted to approximately $5 \times 10^5$ cfu/mL and treated with 2×, 5×, 10×, and 20× MIC (MIC=1 µg/mL). Compound A stock solution was prepared at 10 mg/mL in DMSO. Time points were collected and viable bacteria were counted on MH Agar plates after an 18 hour incubation. Studies examining time-kill kinetics of Compound A against *S. aureus* ATCC 27660 at 2× MIC concentrations show that reductions of 3 $\log_{10}$ units in the initial inoculum occur in 5 hours. No re-growth is observed in the cultures over 72 hours at 1× MIC concentrations. See, FIG. 1A and FIG. 1B.

Example 9

Serial Passage Resistance in MSSA (ATCC 29213) and MRSA (ATCC 33591)

Frozen bacterial stocks (20 µL) of *S. aureus* ATCC29213 or methicillin-resistant *S. aureus* (MRSA ATCC 33591) were inoculated into 3 mL cation-adjusted Mueller-Hinton medium and incubated at 37° C. on a shaker platform (250 rpm) overnight. The suspension was diluted to approximately $5 \times 10^5$ cfu/mL and inoculated into a polypropylene (Costar) 96-well round bottom plate (90 µL volumes). Compound stock solutions of Compound A and norfloxacin (Sigma Aldrich, St. Louis, Mo.; Catalogue #N9890) were prepared in DMSO and serial two-fold dilutions of compound were made in 0.01% acetic acid, 0.2% bovine serum albumin directly in the wells of the polypropylene plate at 10 µL/well. Final concentrations of Compound A were 50, 25, 12.5, 6.25, 3.13, 1.56, 0.78, 0.39, 0.19, 0.098, 0.049, and 0.024 µg/mL. Final concentration ranges of norfloxacin were 100, 50, 25, 12.5, 6.25, 3.13, 1.56, 0.78, 0.39, 0.19, 0.098, and 0.049 µg/mL. DMSO concentrations did not exceed 1% in the assay. All samples were performed in triplicate. Following a 24 hour incubation at 37° C., cell growth was assessed by observing the presence of "acceptable growth", defined by CLSI as a ≥2 mm button or definite turbidity. The MIC wells were defined as the lowest concentration where acceptable growth was not observed. For serial passage, 50 µL aliquots were taken from 2 of 3 replicate wells at 0.5× MIC and combined into 900 µL of fresh cation-adjusted Mueller-Hinton medium. The OD$_{600}$ was measured and the cell suspensions were inoculated into polypropylene 96-well round bottom plates (90 µL volumes) at approximately $5 \times 10^5$ cfu/mL. Ten µL of compound stock solutions were added previously to the wells to achieve the concentration ranges for each compound described above. All samples were performed in triplicate. The plates were incubated for 24 hours at 37° C. This process was repeated for a total of 17 passages and MIC values were recorded at each passage.

Figure 2:
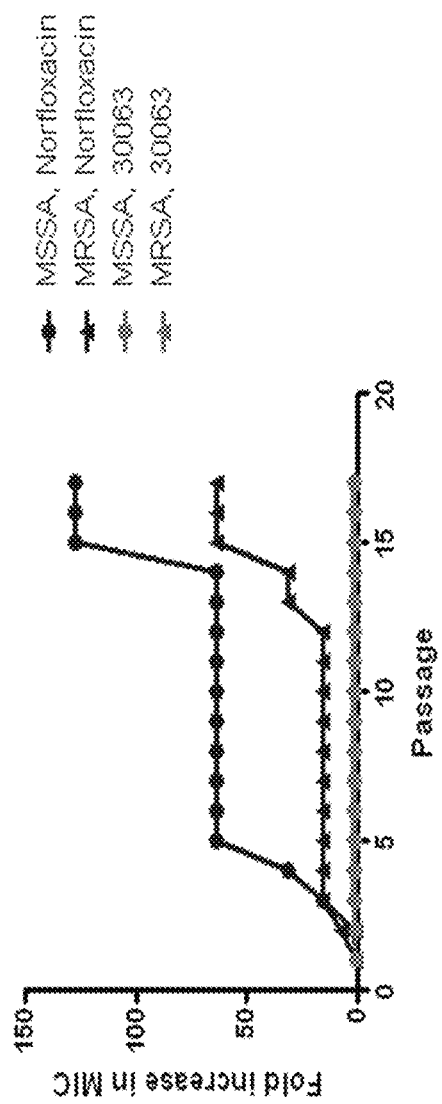
FIG. 2 shows association of passage of *S. aureus* with norfloxacin with a significant rise in MIC values by passage 3 (4 doubling dilutions) for both MSSA and MRSA.

Passage of *S. aureus* with norfloxacin was associated with a significant rise in MIC values by passage 3 (4 doubling dilutions) for both MSSA and MRSA that reached 128-fold and 64-fold increases, respectively, by passage 15. Conversely, there was no change in the MICs for Compound A against MSSA ATCC 29213 or MRSA ATCC 33591 over the entire 17 passage time course. See, FIG. 2.

Example 10

In Vitro Metabolic Stability of Compound A—Blood Plasma

Pooled plasma samples from human (mixed gender), rat (mixed breed and gender) and dog (mixed breed and gender) were incubated with Compound A (5 µM) at 37° C. for 0 and 60 minutes (duplicate samples). Incubations were terminated by addition of ice-cold precipitation solvent (acetonitrile: glacial acetic acid, 9:1 v/v). Supernatants were diluted with equal volume of 0.1% formic acid and analyzed by HPLC-MS/MS. Plasma stability is reported as % parent compound at 60 minutes relative to amount of parent at 0 minutes. Results are shown in Table 4.

TABLE 4

| Species | Plasma Stability (%) |
|---|---|
| Human | 96 |
| Rat (mixed breeds) | 102 |
| Dog (mixed breeds) | 100 |

There is little to no loss of Compound A in human, rat and dog plasma following 1 hour incubation at 37° C., indicating high plasma stability. There was also little to no loss of Compound A in humans, cynomolgus monkeys, and rabbits, (data not shown).

Example 11

Efficacy of Compound A in the Mouse Thigh Burden Model

Female 6-7-week old CD-1 mice were made neutropenic with cyclophosphamide (150 mg/kg, i.p.) on days 4 and 1 before i.m. inoculation with *S. aureus* (ATCC 13709). *S. aureus* inoculum was prepared by transferring colonies from 18-20-hour tryptic soy agar (TSA) cultures to sterile PBS. The density was adjusted to approximately $10^6$ cfu/mL with the aid of a spectrophotometer, and the inoculum concentration was determined by the dilution plate count method. Mice were inoculated by injecting each posterior thigh with 0.1 mL of inoculum. Compound A was given to separate groups of mice (4 females/group) by i.v. bolus doses of 1 or 2 mg/kg/dose at 1 and 5, 1 and 9, or 1 and 13 hours post inoculation as shown in Table 5. A separate control group of 4 mice received the inoculum without antibiotic treatment. Compound A was dissolved 50%/50% v/v sterile USP purified water/PBS. Thighs were harvested at 25 hours after inoculation. Thigh muscle and bone tissue were homogenized, aliquots of serial dilutions were plated on TSA and incubated at 37° C. for 20 hours, and colony counts were obtained to calculate cfu/thigh. The parameters are shown in Table 5.

TABLE 5

| Group No. | Treatment | Dose (mg/kg/dose) | Total Dose (mg/kg) | Volume (ml/kg) | Treatment (hr after inoculation) | Thigh Harvest (hr after inoculation) | No. Mice |
|---|---|---|---|---|---|---|---|
| 1 | Inoc. control | NA | NA | NA | NA | 25 | 4 |
| 2 | Compound A | 1 | 2 | 4 | 1 and 5 | 25 | 4 |
| 3 | Compound A | 2 | 4 | 4 | 1 and 5 | 25 | 4 |
| 4 | Compound A | 1 | 2 | 4 | 1 and 9 | 25 | 4 |
| 5 | Compound A | 2 | 4 | 4 | 1 and 9 | 25 | 4 |
| 6 | Compound A | 1 | 2 | 4 | 1 and 13 | 25 | 4 |
| 7 | Compound A | 2 | 4 | 4 | 1 and 13 | 25 | 4 |

Figure 3:
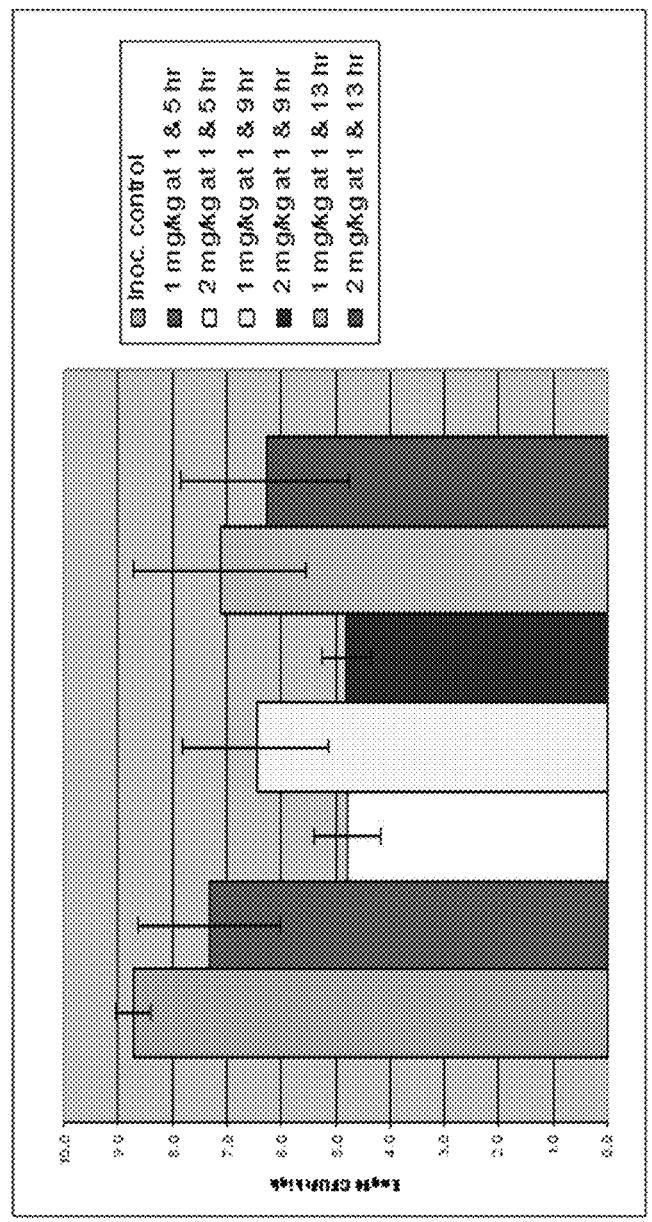
FIG. 3 shows efficacy of Compound A against *S. aureus* in the Mouse Thigh Burden Model.

Compound A was most effective in reducing the bacterial population in inoculated thighs when administered at 2 mg/kg/dose at either 1 and 5 or 1 and 9 hours after inoculation. Bacterial reductions in these 2 groups were 3.96 and 3.93 logs lower, respectively, than those of the inoculated control group. See, FIG. 3.

Example 12

Efficacy vs. Vancomycin in the Rat Thigh Burden Model

For each experiment, female 8-9-week old femoral vein cannulated Crl:CD(SD) rats were made neutropenic with cyclophosphamide (150 mg/kg, i.p.) on days 4 and 1 before i.m. inoculation with S. aureus (ATCC 13507). A suspension of S. aureus was prepared from colonies obtained from an overnight culture, placed in PBS, and adjusted to approximately $10^7$ cfu/mL with the aid of a spectrophotometer. Each rat was injected 0.2 mL of inoculum into the thigh muscle of the right hind leg. Thighs were harvested at 25 hours after inoculation and processed to determine cfu/thigh. Compound A was given by i.v. bolus injection into a tail vein or 1-hour i.v. infusion, or 4-hour i.v. infusion via the femoral vein cannulae at different time intervals following inoculation. Separate inoculation control groups were included in each experiment, and vancomycin groups were included as comparative agents in the first and second experiments. Each group, including the controls and comparative agent, consisted of 4 rats.

Figure 4:
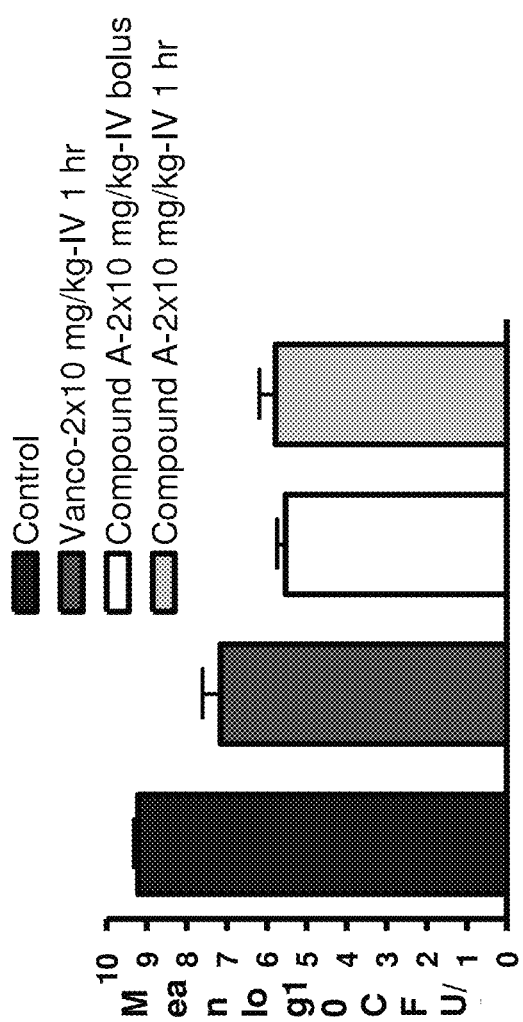
FIG. 4 shows efficacy of Compound A versus vancomycin against *S. aureus* in the Rat Thigh Burden Model.

For Compound A, i.v. bolus (10 mg/kg/dose, 20 mg/kg total dose) and 1 hour i.v. infusions (10 mg/kg/dose, 20 mg/kg total dose) reduced the bacterial load by 3.2 and 3.0 logs, respectively, in comparison to inoculated controls. Reductions relative to inoculum levels at 1 hour post-infection were approximately 2.2 to 2.0 logs, respectively. Efficacy was comparable to vancomycin. See, FIG. 4.

Example 13

Efficacy Compound A in Mouse Sepsis Model: S. aureus Infection

Sterile saline, vancomycin, or Compound A were administered to separate groups of 8-week old female CD-1 mice (8 mice/group) 1 and 7 hours after i.p. injections of S. aureus (ATCC 13709, $5 \times 10^7$ cfu/mL in 5% mucin, 0.5 mL/mouse). Compound A was dissolved in 50%/50% v/v sterile USP purified water/TBS. A suspension of S. aureus was prepared from colonies transferred from the TSA plate to sterile PBS. An aliquot of the stock suspension was added to 5% mucin for a final concentration of about $5 \times 10^7$ cfu/mL. Study design and doses are shown in Table 6. The mice were observed for 6 days following inoculation for mortality.

TABLE 6

| Treatment | Dose (mg/kg/dose) | Total Dose (mg/kg) | Route of Test Compound | Volume (ml/kg) | Test Compound Injection Schedule (hr after inolulation) | No. Mice |
|---|---|---|---|---|---|---|
| Inoc. control | NA | NA | NA | NA | NA | 8 |
| Vancomycin | 10 | 10 | s.c. | 10 | 1 | 8 |
| Compound A | 3 | 6 | i.v. | 4 | 1 & 7 | 8 |
| Compound A | 5 | 10 | i.v. | 4 | 1 & 7 | 8 |
| Compound A | 10 | 20 | i.v. | 4 | 1 & 7 | 8 |

Figure 5:
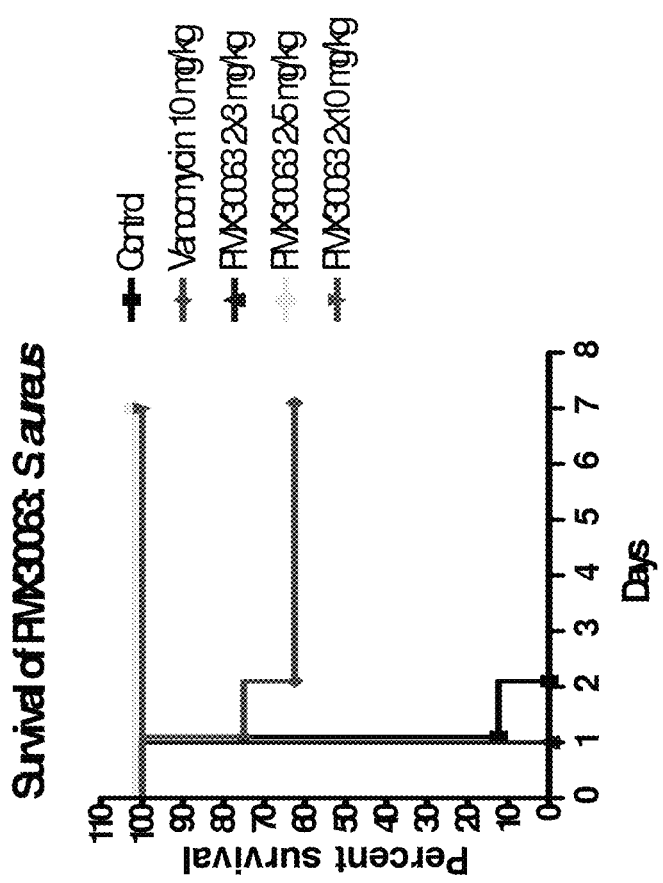
FIG. 5 shows efficacy of Compound A against *S. aureus* in the Mouse Sepsis Model.

Dose-dependent efficacy was observed with Compound A that was comparable to the vancomycin treatment group. All untreated mice died within the first day of treatment. At the 2×5 and 2×10 mg/kg doses of Compound A, full protection was achieved with Compound A. See, FIG. 5.

Example 14

Acute Toxicity Studies—Maximum Tolerated Doses

Maximum tolerated dose (MTD) determinations were made in ascending/descending dose studies in mice and rats. Compound A was administered by either i.v. bolus injection in the tail vein of mice and rats or by i.v. infusion via catheter in the femoral vein of rats. At each dose, two to three animals were administered compound and clinical signs were recorded over a 4 to 7 day period. Gross necropsy was performed at the conclusion of the study. Results are shown in Table 7.

TABLE 7

| | MTD (mg/kg) | |
|---|---|---|
| Dosage Compound A | mouse | rat |
| i.v. bolus | 30 | N.D. |
| i.v. infusion - 1 hour | N.D. | >24 |

The MTD for Compound A in the rat was >24 mg/kg when administered by i.v. infusion for 1 hour.

Example 15

Pharmacokinetics of Compound A in Rats

Crl:CD (SD) rats were administered Compound A by i.v. bolus injection at the indicated dosages. Plasma was prepared from blood samples taken at 9 time points (n=3) over 28 hours. Compound levels were determine by HPLC-MS/MS. All animals were fitted with two jugular vein cannula (JVC), one each for dose administration and blood collection. Each route of administration was dosed as N=3 Animals were supplied with a commercial rodent diet and water ad libitum. Each rat received a bolus dosed via the appropriate route of administration at time zero on the day of dosing. Blood sampling times are shown in Table 8.

Each blood sample was collected from the rats via a JVC and placed into chilled polypropylene tubes containing sodium EDTA as an anticoagulant. Samples were centrifuged at a temperature of 4° C. and at a speed of 13,000 rpm for 5 minutes. Samples were maintained chilled throughout processing. Each plasma sample was then transferred into labeled polypropylene tubes, placed on dry ice, and stored in a freezer set to maintain −60° C. to −80° C.

Plasma study samples were extracted and analyzed using a previously developed method. A single standard curve and six replicates of quality control samples at three concentrations were extracted using DMSO containing 0.1% formic acid. Plasma samples (50 µL) were added to 150 µL solvent and centrifuged. Supernatants were analyzed by LC/MSMS using a Perkin Elmer series 200 micropump and PE Sciex API4000 Electrospray mass spectrometer. Standard curves were prepared at concentrations of 10000, 5000, 1000, 500, 250, 100, 50 and 25 ng/mL. Quality control samples were prepared at concentrations of 5000, 500, and 50 ng/mL. The standard curve and quality control samples were prepared from independently prepared stock solutions. At least ⅝ of standards must have accuracy within ±15%, except at the LLOQ where ±20% is acceptable. Two thirds of the batch QCs must have accuracy within ±15% of nominal, and at least one QC must pass at each level in order for the run to be accepted.

Individual plasma concentration versus time data for Compound A was subjected to non-compartmental analysis using the pharmacokinetic program WinNonlin v4.1. Plasma concentrations below the limit of quantitation (25 ng/ml) were assigned a value of zero for pharmacokinetic analysis. Nominal dosing concentrations were used in all calculations.

Results are shown below in Table 9.

TABLE 9

| PK parameter | Compound A (5 mg/kg, i.v. bolus) |
| --- | --- |
| $C_{max}$ (µg/mL) | 89.2 |
| $T_{1/2}$ (hours) | 3 |
| $V_D$ (mL/kg) | 110 |
| $C_L$ (mL/hr/kg) | 28 |

The plasma half-life for Compound A in rat plasma was significantly long and clearance values are low.

Example 16

Formulations

The saturation solubility of Compound A in various excipients was investigated at 25° C. and the results are reported in Table 10 (saturation solubility of Compound A as the free base).

TABLE 10

| Excipient | Functional Category | Compound A (free base) saturation solubility at 25° C. (mg/mL) |
| --- | --- | --- |
| Purified Water | Control | 65 |
| Propylene Glycol | Cosolvents | 90 |
| PEG 400 | | 18.5 |
| Glycerin | | 53 |
| DMA | | 0.60 |
| Ethanol | | 1.13 |
| Benzyl alcohol | | 1.83 |
| Citric Acid/Sodium Citrate (pH3) | Buffers | 65.5 |
| Citric Acid/Sodium Citrate (pH5) | | 11.2 |
| Tris(hydroxymethyl)amino methane HCl (pH7.0) | | 61.4 |
| 0.9% Saline | Diluent | N/A |
| 1.2% Saline | | N/A |

N/A: Not available as the formulation formed a viscous yellow gel

Preliminary investigations indicated that benzyl alcohol, ethanol and DMA were poor vehicles for Compound A with a saturation solubility value of 1.83, 1.13 and 0.60 mg/mL respectively. On the other hand, good saturation solubility of 90 mg/mL, 65 mg/mL and 53 mg/mL were achieved in propylene glycol, purified water and glycerin and were conse-

TABLE 8

| Treatment Group | Test Compound | Animals (N) | Dose (mg/kg, free base) | Dosing Solution Conc. (mg/mL) | Dosing Volume (mL/kg) | Vehicle | Sampling Time Points |
| --- | --- | --- | --- | --- | --- | --- | --- |
| 1 | Compound A | 3 | 5 | 1.25 | 4 | Tris-Buffered Saline, pH 7.4 | Predose, 2, 5, 15, 30 minutes, 1, 2, 4 and 8 hours postdose | quently investigated further. Good solubility values were achieved at pH 3 and 7.4 with values of 65.5 and 61.4 mg/ml respectively. The solubility however, appeared to drop at pH5 with a value of 12.1 mg/mL. The saturation solubility of Compound A in 0.9% and 1.2% sodium chloride solution could not be detected as the formulation formed a viscous yellow gel.

The saturation solubility of Compound A in various multi-component systems was investigated at 25° C. and the results are reported in Table 11 (saturation solubility of Compound A as the free base).

TABLE 11

| Excipient | Diluent | Compound A (free base) saturation solubility at 25° C. (mg/mL) |
|---|---|---|
| 20% w/v propylene glycol | saline | N/A |
| 30% w/v propylene glycol | saline | N/A |
| 40% w/v propylene glycol | saline | N/A |
| 50% w/v propylene glycol | saline | N/A |
| 15% w/v propylene glycol | purified water | 64.9 |
| 30% w/v propylene glycol | purified water | 59.1* |
| 50% w/v propylene glycol | purified water | 74.7 |
| 30% w/v propylene glycol and 5 w/v ethanol | purified water | 43.9 |
| 15% w/v glycerin | purified water | 63.5 |
| 30% w/v glycerin | purified water | 63.1 |
| 50% w/v glycerin | purified water | 56.8 |
| 20% w/v Kleptose | purified water | 79.7 |
| 40% w/v Kleptose | purified water | 102.0 |
| 25% w/v Captisol | purified water | 64.3 |

N/A: Not available as the formulation formed a viscous yellow gel
*The formulation gelled during centrifugation but liquefied on standing.

The formulations which exhibited suitable results included 50% w/v propylene glycol and 15% w/v glycerin in purified water with a saturation solubility value at 25° C. of 74.7 mg/mL and 63.5 mg/mL respectively. Good saturation solubility was also achieved with various complexing agents with values of 79.7, 102.0 and 64.3 mg/mL for 20% w/v Kleptose, 40% w/v Kleptose and 25% w/v Captisol respectively. Results also indicated that addition of Compound A to 20-50% w/v propylene glycol in saline resulted in the formation of a viscous yellow gel and consequently could not be analyzed by UV. However, the gelling phenomenon was concentration dependent and was observed in formulations as the Compound A concentration in the formulation approached the saturation solubility value of the drug. Additionally, the gelling process could be easily reversed by adding a small volume of the excipient formulation or a few drops of ethanol. Addition of 5% w/v ethanol into the formulation did not inhibit the gelling phenomenon but it was still easily reversible and able to be analyzed by UV spectrophotometry.

Following an evaluation of preliminary excipient screening data, three suitable formulations were chosen for further formulation development. These formulations are 20% w/v Kleptose solution, 20% w/v propylene glycol in purified water, and 15% w/v glycerin in purified water.

The formulation of 50 mg/mL Compound A in 20% w/v Kleptose was selected in phase I clinical trial. In addition, solutions of Compound A in water, Kleptose, or Mannitol can be aliquoted out and lyophilized to a solid. The solid can be reconstituted with water before use.

Various modifications of the invention, in addition to those described herein, will be apparent to those skilled in the art from the foregoing description. Such modifications are also intended to fall within the scope of the appended claims.

What is claimed is:
1. A method of preparing the compound having the formula

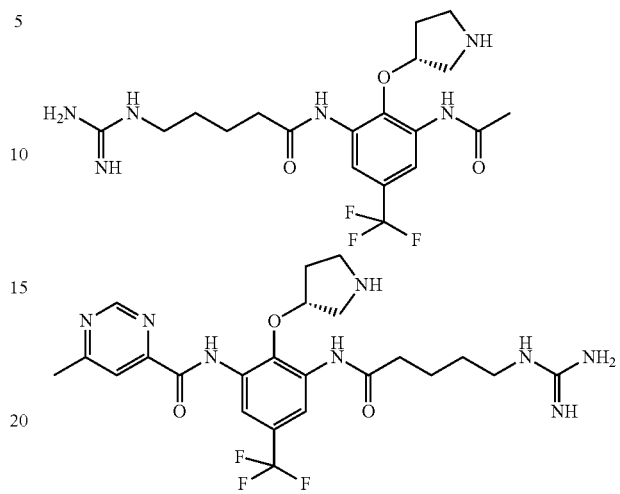

comprising:
a) reacting (R)-(−)-N-Boc-3-pyrrolidinol with a strong base to form a mixture; further reacting the mixture with 2-chloro-5-(trifluoromethyl)-1,3-dinitrobenzene to form a compound having Formula II

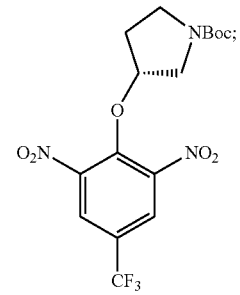

b) reacting the compound of Formula II with an alcohol and a transition metal catalyst in the presence of hydrogen to form a compound of Formula III

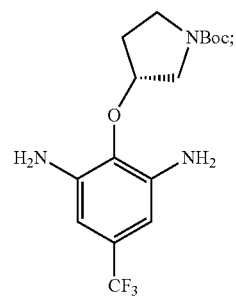

c) adding the compound of Formula III and pyrimidine-4,6-dicarboxylic acid to a mixture of 2-chloro-4,6-dimethoxy-1,3,5-triazine and N-methylmorpholine to form a compound of Formula IV

IV

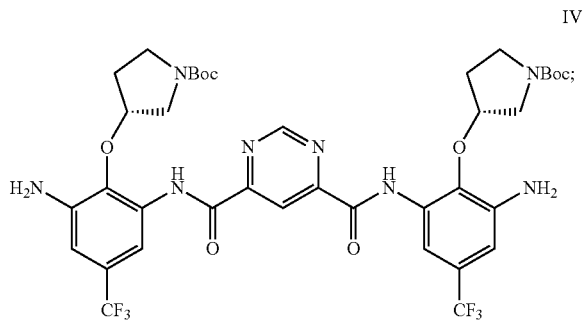 [SMILES: CC(C)(C)OC(=O)N1CC[C@@H](Oc2c(N)cc(C(F)(F)F)cc2NC(=O)c2cc(C(=O)Nc3cc(C(F)(F)F)cc(N)c3O[C@@H]3CCN(C(=O)OC(C)(C)C)C3)ncn2)C1]

d) reacting the compound of Formula IV with N-Boc-guanidine butyric acid to form a compound of Formula V

V

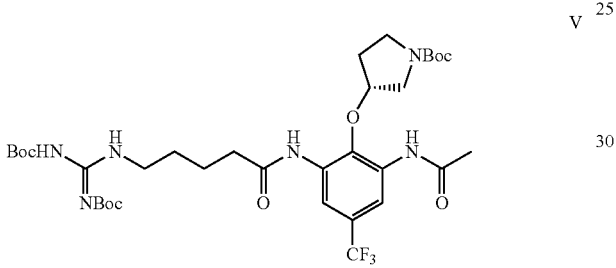

and

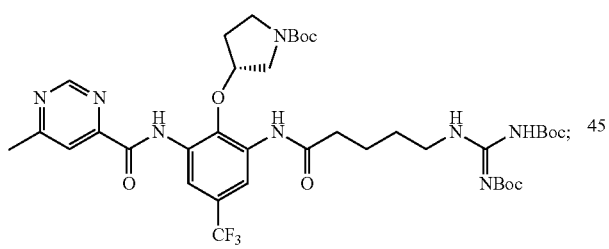

e) deprotecting the compound of Formula V to produce the compound; or a) deprotonating (R)-3-Hydroxypyrrolidine-1-carboxylic acid tert-butyl ester, and reacting the resultant compound with 2-chloro-1,3-dinitro-5-trifluoromethylbenzene to form (R)-3-(2,6-dinitro-4-trifluoromethylphenoxy)pyrrolidine-1-carboxylic acid tert-butyl ester;

b) reducing (R)-3-(2,6-dinitro-4-trifluoromethylphenoxy) pyrrolidine-1-carboxylic acid tert-butyl ester in the presence of an alcohol, a transition metal catalyst, and hydrogen to form (R)-3-(2,6-diamino-4-trifluoromethylphenoxy)-pyrrolidine-1-carboxylic acid tert-butyl ester;

c) coupling (R)-3-(2,6-diamino-4-trifluoromethylphenoxy)-pyrrolidine-1-carboxylic acid tert-butyl ester with pyrimidine-4,6-dicarboxylic acid in the presence of 1-[(3-(dimethylamino)-propyl)]-3-ethylcarbodiimide hydrochloride to form pyrimidine-4,6-dicarboxylic acid bis-{[3-amino-2-((R)-1-(tert-butoxycarbonyl)pyrrolidin-3-yloxy)-5-trifluoromethyl-phenyl]amide};

d) reacting pyrimidine-4,6-dicarboxylic acid bis-{[3-amino-2-((R)-1-(tert-butoxycarbonyl)pyrrolidin-3-yloxy)-5-trifluoromethyl-phenyl]amide} with ({[(tert-butoxycarbonyl)amino][(tert-butoxycarbonyl)imino] methyl}amino)pentanoic acid in the presence of phosphorous oxychloride to form pyrimidine-4,6-dicarboxylic acid bis-{[3-(5-({[(tert-butoxycarbonyl)amino][(tert-butoxycarbonyl)imino]methyl}amino)-pentanoylamino)-2-((R)-1-(tert-butoxycarbonyl)-pyrrolidin-3-yloxy)-5-trifluoromethyl-phenyl]-amide};

e) deprotecting pyrimidine-4,6-dicarboxylic acid bis-{[3-(5-({[(tert-butoxycarbonyl)amino][(tert-butoxycarbonyl)imino]methyl}amino)-pentanoylamino)-2-((R)-1-(tert-butoxycarbonyl)-pyrrolidin-3-yloxy)-5-trifluoromethyl-phenyl]-amide} to form crude pyrimidine-4,6-dicarboxylic acid bis-{[3-(5-guanidino-pentanoylamino)-2-((R)-pyrrolidin-3-yloxy)-5-trifluoromethyl-phenyl]-amide}tetrahydrochloride; and f) purifying crude pyrimidine-4,6-dicarboxylic acid bis-{[3-(5-guanidino-pentanoylamino)-2-((R)-pyrrolidin-3-yloxy)-5-trifluoromethyl-phenyl]-amide}tetrahydrochloride by reverse-phase chromatography; or a) deprotonating (R)-3-Hydroxypyrrolidine-1-carboxylic acid tert-butyl ester and further reacting the resultant compound with 2-chloro-1,3-dinitro-5-trifluoromethylbenzene to form (R)-3-(2,6-dinitro-4-trifluoromethylphenoxy)pyrrolidine-1-carboxylic acid tert-butyl ester;

b) reducing (R)-3-(2,6-dinitro-4-trifluoromethylphenoxy) pyrrolidine-1-carboxylic acid tert-butyl ester in the presence of an alcohol, a transition metal catalyst, and hydrogen, to form (R)-3-(2,6-diamino-4-trifluoromethylphenoxy)-pyrrolidine-1-carboxylic acid tert-butyl ester;

c) coupling (R)-3-(2,6-diamino-4-trifluoromethylphenoxy)-pyrrolidine-1-carboxylic acid tert-butyl ester with pyrimidine-4,6-dicarboxylic acid in the presence of 1-[(3-(dimethylamino)-propyl)]-3-ethylcarbodiimide hydrochloride to form pyrimidine-4,6-dicarboxylic acid bis-{[3-amino-2-((R)-1-(tert-butoxycarbonyl)pyrrolidin-3-yloxy)-5-trifluoromethyl-phenyl]amide};

d) reacting pyrimidine-4,6-dicarboxylic acid bis-{[3-amino-2-((R)-1-(tert-butoxycarbonyl)pyrrolidin-3-yloxy)-5-trifluoromethyl-phenyl]amide} with N-Cbz acid in the presence of thionyl chloride;

e) reducing the resultant compound of d) in the presence of an alcohol, a transition metal catalyst, and hydrogen;

f) reacting the resultant compound of e) with di-Boc pyrazole;

g) deprotecting the resultant compound of f) to produce the compound.

2. A method of preparing a pharmaceutically acceptable salt of the compound having the formula

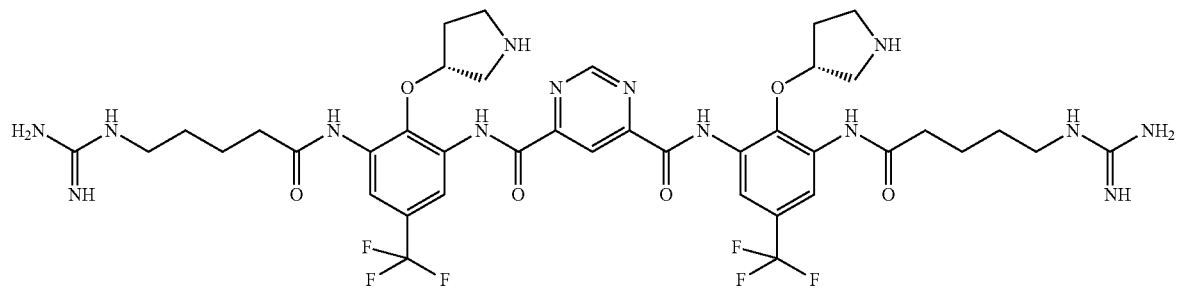 [SMILES: N=C(N)NCCCCC(=O)Nc1cc(C(F)(F)F)cc(NC(=O)c2cc(C(=O)Nc3cc(C(F)(F)F)cc(NC(=O)CCCCNC(=N)N)c3O[C@@H]3CCNC3)ncn2)c1O[C@@H]1CCNC1]

comprising:
a) reacting (R)-(−)-N-Boc-3-pyrrolidinol with a strong base to form a mixture; further reacting the mixture with 2-chloro-5-(trifluoromethyl)-1,3-dinitrobenzene to form a compound having Formula II

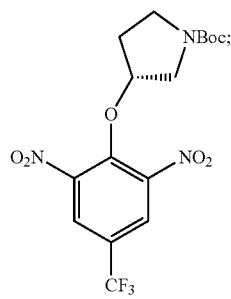

II b) reacting the compound of Formula II with an alcohol and a transition metal catalyst in the presence of hydrogen to form a compound of Formula III

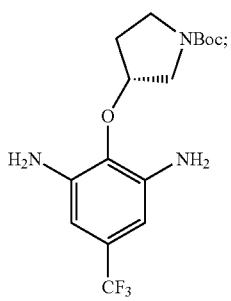

III c1) adding the compound of Formula III and pyrimidine-4,6-dicarboxylic acid to a mixture of 2-chloro-4,6-dimethoxy-1,3,5-triazine and N-methylmorpholine to form a compound of Formula IV

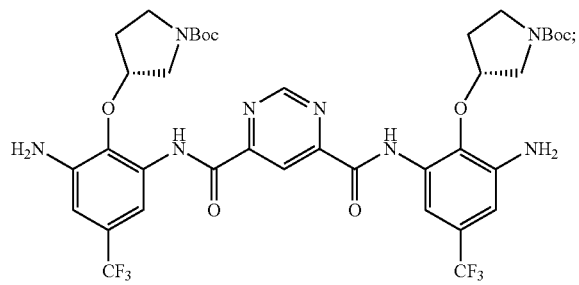

IV or
c2) adding the compound of Formula III and pyrimidine-4,6-dicarboxylic acid to a mixture of 1-ethyl-3-[3-(dimethylamino)propyl]-carbodiimide hydrochloride (EDCl) and anhydrous pyridine to form a compound of Formula IV

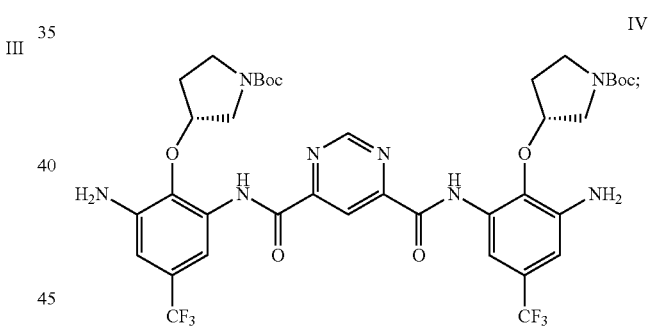

IV d) adding the compound of Formula IV with an N-Cbz acid to a solution comprising anhydrous pyridine, dimethylaminopropylamine, and any one of thionyl chloride, $POCl_3$, $(EtO)_2POCl$, or oxalyl chloride to form a compound of Formula Va

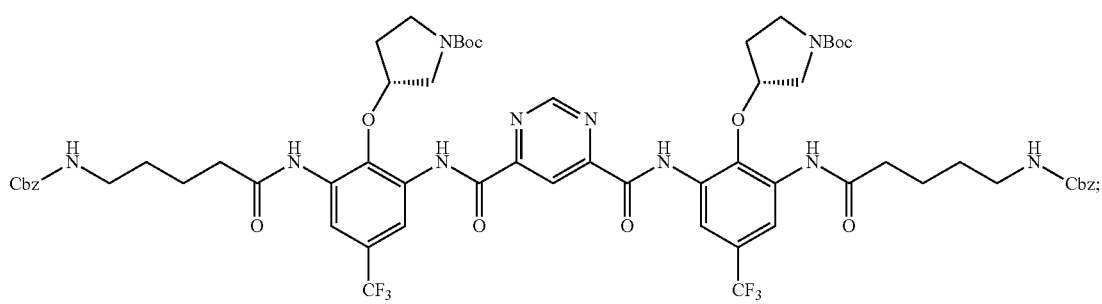

Va e) hydrogenlysis of the Cbz group of the compound of Formula Va to produce the compound of formula VI
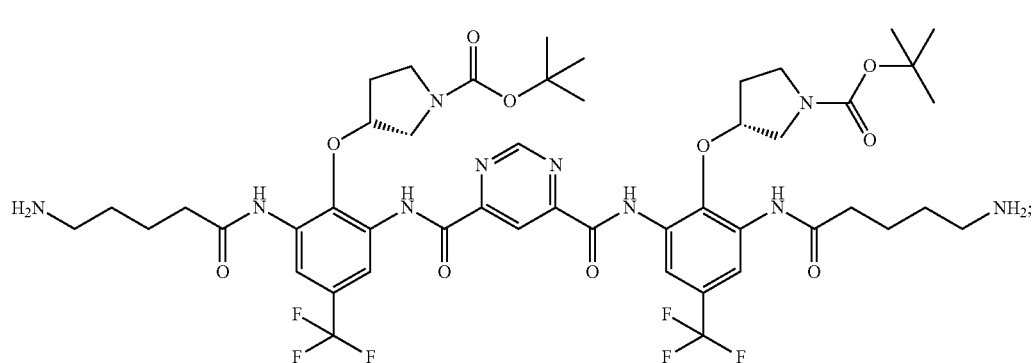
VI
f) protecting the compound of Formula VI to produce the compound of formula VII
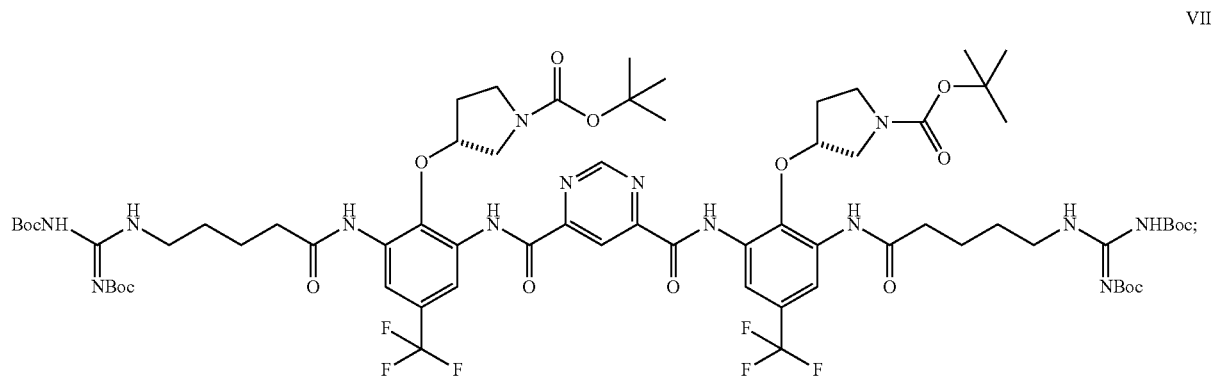
VII
and
g) deprotecting the compound of Formula VII to produce a pharmaceutically acceptable salt of the compound.
* * * * *